(12) United States Patent
Owens et al.

(10) Patent No.: US 9,932,329 B2
(45) Date of Patent: *Apr. 3, 2018

(54) BENZIMIDAZOLE DERIVATIVES AS RLK AND ITK INHIBITORS

(71) Applicant: Principia Biopharma, Inc., South San Francisco, CA (US)

(72) Inventors: Timothy Owens, San Carlos, CA (US); Ronald J. Hill, Burlingame, CA (US)

(73) Assignee: PRINCIPIA BIOPHARMA, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/121,605

(22) PCT Filed: Feb. 23, 2015

(86) PCT No.: PCT/US2015/017014
§ 371 (c)(1),
(2) Date: Aug. 25, 2016

(87) PCT Pub. No.: WO2015/134210
PCT Pub. Date: Sep. 11, 2015

(65) Prior Publication Data
US 2016/0368908 A1 Dec. 22, 2016

Related U.S. Application Data

(60) Provisional application No. 61/947,087, filed on Mar. 3, 2014.

(51) Int. Cl.
*C07D 413/14* (2006.01)
*C07D 419/14* (2006.01)
*A61K 31/405* (2006.01)

(52) U.S. Cl.
CPC ......... *C07D 413/14* (2013.01); *C07D 419/14* (2013.01)

(58) Field of Classification Search
CPC ..................... C07D 413/14; C07D 419/14
See application file for complete search history.

(56) References Cited

FOREIGN PATENT DOCUMENTS

| WO | 2005079791 | 9/2005 | | |
|---|---|---|---|---|
| WO | 2013184757 | 12/2013 | | |
| WO | WO 2013184757 A1 * | 12/2013 | ......... | A61K 31/4184 |
| WO | 2014036016 | 3/2014 | | |
| WO | WO 2014036016 A1 * | 3/2014 | ........... | C07D 401/14 |

OTHER PUBLICATIONS

Patent Cooperation Treaty, International Search Report issued for PCT/US2015/017014, dated Apr. 23, 2015, 3 pages.

* cited by examiner

*Primary Examiner* — Amanda L Aguirre
(74) *Attorney, Agent, or Firm* — Bryan Cave LLP

(57) ABSTRACT

The present disclosure is directed to certain inhibitors of RLK and ITK of formula (I), pharmaceutical compositions comprising such compounds, and method of treating diseases mediated by inhibition of RLK and ITK.

17 Claims, 2 Drawing Sheets

BENZIMIDAZOLE DERIVATIVES AS RLK AND ITK INHIBITORS

CROSS-REFERENCE TO PRIOR APPLICATIONS

This application claims the benefit of priority to U.S. Ser. No. 61/947,087 filed Mar. 3, 2014 which is hereby incorporated by reference in its entirety.

FIELD OF THE DISCLOSURE

The present disclosure is directed to certain compounds that are potent inhibitors of resting lymphocyte kinase (RLK) and IL2-inducible T-cell kinase (ITK), pharmaceutical compositions comprising such compounds, and method of treating diseases treatable by inhibition of RLK and ITK.

BACKGROUND

Th17 cells constitute a population of T helper cells that secrete the pro-inflammatory cytokine IL-17. These cells have been proposed to be key in the development of a range of human diseases including various autoimmune conditions, inflammation, allergy and development of the tumor microenvironment (see Park et al., A distinct lineage of CD4 T cells regulate tissue inflammation by producing IL-17, Nat. Immunol. 6:1133-1141, 2005; Qi et al., Correlation between Th17 cells and tumor microenvironment, Cell. Immunol. 285: 18-22, 2013).

Besides the preclinical studies, there are clinical data correlating enhanced IL-17 levels and increased frequencies of Th17 in a variety of human diseases. Elevation of IL-17 has been detected in the sera and biopsies of rheumatoid arthritis (RA) and systemic lupus erythematosus (SLE) patients (see Agarwal et al., Interleukin 17 levels are increased in juvenile idiopathic arthritis synovial fluid and induce synovial fibroblasts to produce proinflammatory cytokines and matrix metalloproteinases, J. Rhematology, 35:515-519, 2008; Wong et al., Hyperproduction of IL-23 and IL-17 in patients with systemic lupus erythematosus: implications for Th17-mediated inflammation in auto-immunity, Clin. Immunol. 127:385-393, 2008). IL-17A promotes ex vivo induction of proinflammatory cytokines by synoviocytes from RA patients (see Chabaud et. al., Enhancing effect of IL-17 on IL-1-induced IL-6 and leukemia inhibitory factor production by rheumatoid arthritis synoviocytes and its regulation by Th2 cytokines, J. Immunol. 161:409-414, 1998.) and a humanized anti-IL-17 antibody has been used for a proof-of-concept clinical trial for RA patients with positive results (see Genovese et al., LY2439821, a humanized anti-interleukin-17 monoclonal antibody, in the treatment of patients with rheumatoid arthritis: a phase I randomized, double-blind, placebo-con-trolled, proof-of-concept study, Arthr. & Rheum. 64: 929-979, 2010). In addition, RA patients treated with humanized anti-IL17 antibody showed reductions in symptoms similar to those produced by the approved anti-TNF antibody infliximab thus providing additional evidence that IL-17 is an important mediator of inflammatory autoimmune diseases.

In multiple sclerosis (MS) patients, the level of messenger RNA for IL-17 in the monocytes from cerebrospinal fluid is elevated and myelin reactive Th17 cells are enriched (see Venken et al., Memory CD4+CD127 high T cells from patients with multiple sclerosis produce IL-17 in response to myelin antigens, J. Neuroimmunol. 226: 185-191, 2010). In psoriatic skin, IL-17A, IL-22 and IL-23 are all elevated and IL-17A induces the expression of genes involved in psoriasis by human keratinocytes (see Res et al., Overrepresentation of IL-17A and IL-22 producing CD8 T cells in lesional skin suggests their involvement in the pathogenesis of psoriasis, PLOS 5: Article ID e14108, 2010; Wilson et al., Development, cytokine profile and function of human interleukin 17-producing helper T cells, Nat. Immunol. 8: 950-957, 2007). An elevation of IL-17 positive cells has also been detected in the affected areas of the gut of Crohn's disease patients compared with unaffected areas (see Annunziato et al., Phenotypic and functional features of human Th17 cells, J. Exp. Med. 204:1849-18-61, 2007). Taken together these human data support modulation of Th17 cells as a therapeutic intervention in a variety of diseases including MS, RA, SLE, psoriasis, and Crohn's disease.

Kinases play critical roles in signaling pathways controlling fundamental cellular processes such as proliferation, differentiation, and death (apoptosis). Two kinases, in particular, ITK and RLK (also referred to as TXK) have been shown to be important for T cell function. In ITK −/− (ITK deleted) CD4$^+$ cells differentiated in vitro into Th17 cells the levels of intracellular IL-17A levels were greatly reduced. It has been observed that differentiation of Th17 cells is impacted as well (see Gomez-Rodriguez et al., Differential expression of IL-17A and IL-17F is coupled to TCR signaling via ITK-mediated regulation of NFATc1, Immunity 31:587-597, 2009). In addition to the decreased differentiation and activation of Th17 cells in the absence of ITK, T cells from these ITK−/− mice show enhanced differentiation of Treg cells that modulate inflammation and prevent development of autoimmunity (see Gomez-Rodriguez et al., Itk-mediated integration of T cell receptor and cytokine signaling regulates the balance between Th17 and regulatory T cells, J. Exp. Med. 10.1084/jem.20131459. 2014). Thus in the absence of ITK, there appears to be a shift in the balance of Th17 and Treg cells that would favor suppression of autoimmune disease. Indeed, when T cells from ITK−/− mice are transferred into a model of T cell mediated colitis, the enhanced Treg capacity suppresses development of the colitis disease model. In yet another in vivo model of IL-17A associated inflammation, antigen-stimulated allergic asthma, the levels of IL-17A in the lungs of ITK−/− mice were reduced in the absence of ITK as well. It is noteworthy that this is not a developmental defect as is sometimes the case for non-induced, germline gene knockout models because the defect in IL-17A expression can be rescued by re-expression of ITK in pre-activated cells suggesting that modulation of ITK with a small molecule inhibitor could affect Th17 differentiation and therefore the inflammation that results from elevated IL-17 levels.

When the deletion of ITK is combined with deletion of RLK in double knockout mice, the effects on TCR signaling and IL-17A production are more severe than in the single knockout mice. Additionally, in the absence of both ITK and RLK, T-cell receptor signaling is impaired, with defects in mitogen-activated protein kinase activation, Ca2+ mobilization, and actin polymerization (see Berg et al., Tec family kinases in T lymphocyte development and function, J. Exp. Med, 23:549-600, 2005).

In general, the effects of knocking out both ITK and RLK in mice causes more profound changes in TCR mediated signaling, T cell functions and production of IL17A than deletion of either kinase alone (see Schaeffer et al., Requirement for Tec kinases RLK and ITK in T cell receptor signaling and immunity, Science, 284:638-641, 1999; Gomez-Rodriguez et al., Differential expression of IL-17A and IL-17F is coupled to TCR signaling via ITK-mediated regulation of NFATc1, Immunit, 31:587-597, 2009; Felices and Berg, The Tec kinases ITK and RLK regulate NKT cell maturation, cytokine production and survival, J. Immunol., 180:3007-3018, 2008). Therefore a compound that is a potent inhibitor of both ITK and RLK kinases could be expected to have different effects and enhanced efficacy on modulation of TCR-induced signaling, including effects on IL-17 mechanisms than one that blocks only one of RLK and ITK kinase.

SUMMARY

N-(1-(((R)-1-(2-Cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)-5-(difluoromethyl)thiophene-2-carboxamide, Tool Compound A, having RLK $IC_{50}$ (1 nm) and ITK $IC_{50}$ (0.5 nm) modulates the production of intracellular IL-17 by purified human Th17 cells in vitro. Furthermore, Tool Compound A modulates the secretion of IL-17 in co-cultures of B and T cells. In addition, at concentrations ~25 nM or lower, this compound blocks the expression of Th17 differentiation markers (including RORγt and IL-17A) in cultures designed to polarize murine T cells into Th17 helper T cell populations (see biological example 9 vide infra).

Accordingly, among the various aspects of the present disclosure may be noted the provision of compounds of Formula (I) that are potent inhibitors of both RLK and ITK kinase activity therefore useful to treat diseases treatable by inhibition of IL17 production.

In a first aspect, the present disclosure provides a compound of Formula (I):

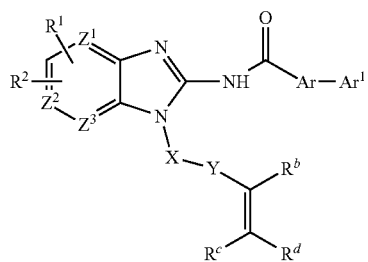

(I)

wherein:

$Z^1$, $Z^2$, and $Z^3$ are CH (or C if substituted with $R^1$ or $R^2$) or $Z^1$, $Z^2$, and $Z^3$ are independently N or CH (or C if substituted with $R^1$ or $R^2$) provided that only one of $Z^1$, $Z^2$, and $Z^3$ is N;

$R^1$ is hydrogen, hydroxyalkyl, alkoxyalkyl, heterocyclyl, heterocyclylalkyl (wherein the heterocyclyl ring in heterocyclyl and heterocyclylalkyl is optionally substituted with one, two, or three substituents independently selected from alkyl, halo, hydroxy, alkoxy, hydroxyalkyl, or alkoxyalkyl), —NR³COR⁴, —CONR³R⁵, -(alkylene)-NR³R⁵ (where each $R^3$ is hydrogen, alkyl, or cycloalkyl, $R^4$ is alkyl, haloalkyl, cycloalkyl, optionally substituted aryl or optionally substituted heteroaryl, and each $R^5$ is hydrogen, alkyl, haloalkyl, hydroxyalkyl, alkoxyalkyl, acyl, cycloalkyl, cycloalkylalkyl, optionally substituted heteroaryl, optionally substituted heteroaralkyl, heterocyclyl, or heterocyclylalkyl (wherein the heterocyclyl ring in heterocyclyl and heterocyclylalkyl is optionally substituted with one, two, or three substituents independently selected from alkyl, halo, hydroxy, alkoxy, hydroxyalkyl, or alkoxyalkyl); or $R^3$ and $R^5$ together with the nitrogen atom to which they are attached form heterocycloamino or spiroheterocycloamino wherein the heterocycloamino ring is optionally substituted with one, two, or three substituents independently selected from alkyl, halo, hydroxyl, alkoxy, hydroxyalkyl, or alkoxyalkyl), —NR⁶R⁷ (where $R^6$ is hydrogen or alkyl and $R^7$ is hydrogen, alkyl, haloalkyl, hydroxyalkyl, alkoxyalkyl, or acyl, or $R^6$ and $R^7$ together with the nitrogen atom to which they are attached form heterocycloamino optionally substituted with one, two, or three substituents independently selected from alkyl, halo, hydroxyl, hydroxyalkyl, or alkoxyalkyl), —OR⁸ (where $R^8$ is alkyl, cycloalkyl, hydroxyalkyl, alkoxyalkyl, or heterocyclylalkyl wherein the heterocyclyl ring in heterocyclylalkyl is optionally substituted with one, two, or three substituents independently selected from alkyl, halo, hydroxyalkyl, or alkoxyalkyl), or -(alkylene)-OR⁹ where $R^9$ is alkyl, cycloalkyl, hydroxyalkyl, alkoxyalkyl, or heterocyclylalkyl wherein the heterocyclyl ring in heterocyclylalkyl is optionally substituted with one, two, or three substituents independently selected from alkyl, halo, hydroxyalkyl, or alkoxyalkyl);

$R^2$ is hydrogen, alkyl, cyano, alkoxy, hydroxy, halo, haloalkyl, or haloalkoxy;

Ar is phenyl or 5-membered heteroaryl optionally substituted with one or two substituents independently selected from alkyl, alkoxy, hydroxy, cyano, alkylthio, halo, haloalkyl, haloalkoxy, or cycloalkyl;

$Ar^1$ is 5- or 6-membered optionally substituted heteroaryl;

X is a moiety of formula II (where Z is bond or alkylene, and ring A is heterocycloamino optionally substituted with one or two substituents independently selected from alkyl, hydroxy, or fluoro), -cycloalkylene-NR$^a$-, or -(alkylene)-NR$^a$— (where each $R^a$ is hydrogen, alkyl or cycloalkyl and alkylene in -(alkylene)-NR$^a$— is optionally substituted with hydroxy or alkoxy);

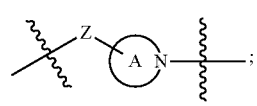

(II)

Y is —CO— or —SO₂—;

$R^b$ is hydrogen, halo, or cyano;

$R^c$ is hydrogen, alkyl, alkyl substituted with alkoxy or hydroxy, cycloalkyl optionally substituted with alkyl, or 3 to 6 membered saturated monocyclic heterocyclyl containing one or two heteroatoms selected from N, O, or S and optionally substituted with one, two, or three substituents independently selected from hydroxy, alkyl, alkoxy, oxetan-3-yl, or fluoro; and $R^d$ is hydrogen, alkyl, or alkyl substituted with amino, alkylamino, or dialkylamino; or $R^b$ and $R^d$ together form a bond;

and/or a pharmaceutically acceptable salt thereof;

provided, however, (i) —Ar—Ar¹ is not 5-(pyrazol-4-yl)-thien-2-yl and (ii) when $R^b$ is cyano, then $R^d$ is hydrogen but $R^c$ is not hydrogen.

In another embodiment there is provided a compound of Formula (I) where Ar is thiophenylene. In a subembodiment Ar is 2,5-thiophenylene.

In one embodiment, the compounds of Formula (I) and/or pharmaceutically acceptable salts thereof (and any embodiments thereof disclosed herein) where —X—Y—C(R$^b$)

=CR$^c$R$^d$ is —X—Y—C(R$^b$)=CHR$^c$ where R$^b$ is cyano, the compound of Formula (I) can be a reversible covalent inhibitor.

In another embodiment, the compounds of Formula (I) and/or pharmaceutically acceptable salts thereof (and any embodiments thereof disclosed herein) where —X—Y—C(R$^b$)=CR$^c$R$^d$ is —X—Y—C(R$^b$)=CHR$^c$ where R$^b$ is cyano, the compound of Formula (I) can be reversible a covalent inhibitor of RLK and ITK.

In yet another embodiment, the compounds of Formula (I) and/or pharmaceutically acceptable salts thereof (and any embodiments thereof disclosed herein) where —X—Y—C(R$^b$)=CR$^c$R$^d$ is —X—Y—C(R$^b$)=CHR$^c$ where R$^b$ is cyano the compound of Formula (I) can be reversible a covalent inhibitor where the reversibility of the covalent bond is determined by Mass spec method described in Biological Example 6, 7, or 8 below.

In yet another embodiment, the compounds of Formula (I) and/or pharmaceutically acceptable salts thereof (and any embodiments thereof disclosed herein) where —X—Y—C(R$^b$)=CR$^c$R$^d$ is —X—Y—C(R$^b$)=CR$^c$ where R$^b$ is cyano, the compounds of Formula (I) can form a reversible covalent bond with Cys442 of ITK and Cys351 of RLK (UniprotKB Sequence ID P42681).

In yet another embodiment, the compounds of Formula (I) and/or pharmaceutically acceptable salts thereof (and any embodiments thereof disclosed herein) where —X—Y—C(R$^b$)=CR$^c$R$^d$ is —X—Y—C(H)=CR$^c$R$^d$ where R$^c$ and R$^d$ are as defined above, the compounds of Formula (I) and/or pharmaceutically acceptable salts thereof can form an irreversible covalent bond where the reversibility of the covalent bond is determined by Mass spec method described in Biological Example 6, 7, or 8 below. In one embodiment, the irreversible bond is with Cys442 of ITK and Cys351 of RLK where the irreversibility of the covalent bond is determined by Mass spec method described in Biological Example 6, method B below.

In a second aspect, provided herein are pharmaceutical compositions comprising a compound disclosed herein, and/or a pharmaceutically acceptable salt thereof; and a pharmaceutically acceptable excipient.

In a third aspect, provided herein are methods of treating a disease treatable by inhibition of IL17 production in a mammal comprising administering to the mammal in need thereof, a pharmaceutical composition comprising a compound disclosed herein and/or a pharmaceutically acceptable salt thereof in a therapeutically effective amount and a pharmaceutically acceptable excipient. In one embodiment the mammal is a human. In another embodiment of third aspect, the diseases are psoriasis, psoriatic arthritis, rheumatoid arthritis, multiple sclerosis, inflammatory bowel disease (Crohn's disease, ulcerative colitis), Behcet's disease, uveitis, keratitis, asthma, testitis, SLE, lupus nephritis, nephritis, chronis (active) hepatitis, Graft-versus-host disease, acute and chronic and prophylaxis, primary biliary cirrhosis, scleroderma, atopic dermatitis, nephrotic syndrome, pediatric autoimmune enteropathy, primary sclerosing cholangitis, pyoderma gangrenosum, or alopecia universalis, or large granular lymphocyte leukemia (e.g. T cell or NK cell phenotype). In another embodiment of third aspect, the diseases are psoriasis, psoriatic arthritis, rheumatoid arthritis, inflammatory bowel disease (Crohn's disease, ulcerative colitis), Behcet's disease, asthma, SLE, lupus nephritis, primary biliary cirrhosis, primary sclerosing cholangitis, multiple sclerosis, or Graft-versus-host disease.

In yet another embodiment of third aspect, the diseases are diseases are psoriatic arthritis, multiple sclerosis, inflammatory bowel disease (Crohn's disease, ulcerative colitis), uveitis, keratitis, testitis, nephritis, chronis (active) hepatitis, primary biliary cirrhosis, scleroderma, nephrotic syndrome, pediatric autoimmune enteropathy, primary sclerosing cholangitis, pyoderma gangrenosum, or alopecia universalis.

Figure 1:
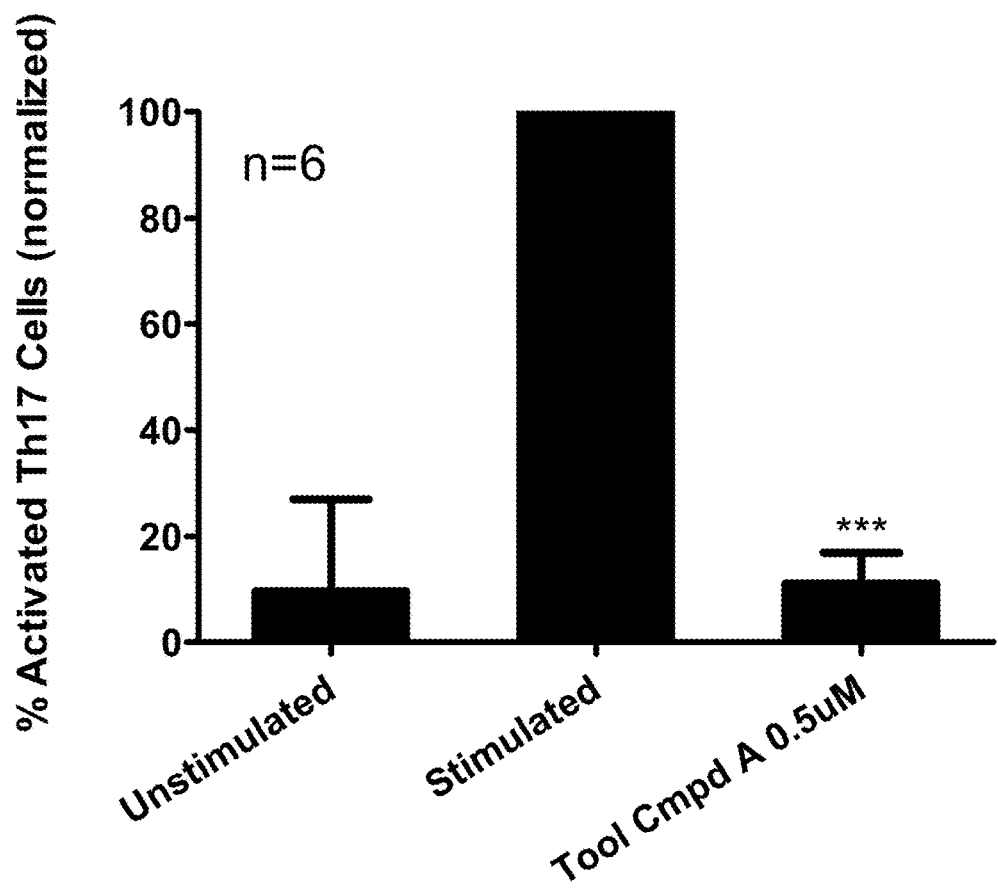
FIG. 1 depicts the inhibition of intracellular expression of IL-17 in the presence of an ITK/RLK inhibitor (Tool Compound A) by a population of T-cells activated by anti-CD3/anti-CD-28.

Compound A inhibits release of soluble proinflammatory cytokines IL17A (sIl-17A), IL17F (sIl-17F), and TNFα by activated T cells which then further modulate the release of immunoglobins (sI$_g$G). High levels of these cytokines are associated with several chronic inflammatory diseases including rheumatoid arthritis, psoriasis and multiple sclerosis.

DESCRIPTION

Definitions:

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Alkoxy" means a —OR radical where R is alkyl as defined above, e.g., methoxy, ethoxy, propoxy, or 2-propoxy, n-, iso-, or tert-butoxy, and the like.

"Alkylamino" means a —NHR radical where R is alkyl as defined above, e.g., methylamino, ethylamino, and the like.

"Acyl" means a —COR radical where R is alkyl, haloalkyl, optionally substituted aryl, or optionally substituted heteroaryl as defined herein, e.g., acetyl, trifluoroacetyl, benzoyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Aminoalkyl" means a linear monovalent hydrocarbon radical of one to six carbon atoms or a branched monovalent hydrocarbon radical of three to six carbons substituted with at least one —$NR^aR^b$ group, preferably one or two $NR^aR^b$ groups, where $R^a$ and $R^b$ are independently hydrogen or alkyl, e.g., aminomethyl, methylaminomethyl, dimethylaminomethyl, 2-aminoethyl, 1-, 2-, or 3-methylaminopropyl, and the like.

"Aryl" means a monovalent monocyclic or bicyclic aromatic hydrocarbon radical of 6 to 10 ring atoms e.g., phenyl or naphthyl. "Cycloalkyl" means a cyclic saturated monovalent hydrocarbon radical of three to ten carbon atoms, e.g., cyclopropyl, cyclobutyl, cyclopentyl, or cyclohexyl, and the like.

"Cycloalkylalkyl" means an -(alkylene)-R where R is cycloalkyl as defined above, e.g., cyclopropylmethyl, cyclobutylmethyl, cyclopentylethyl, or cyclohexylethyl, and the like.

"Cycloalkylene" means a divalent cyclic saturated monovalent hydrocarbon radical of three to ten carbon atoms, e.g., cyclopropylene, cyclobutylene, cyclopentylene, or cyclohexylene, and the like.

"Dialkylamino" means a —$NR_2$ radical where each R is independently alkyl as defined above, e.g., dimethylamino, methylethylamino, and the like.

"Halo" means fluoro, chloro, bromo, or iodo, preferably fluoro or chloro.

"Haloalkyl" means alkyl radical as defined above, which is substituted with one or more halogen atoms, preferably one to five halogen atoms, preferably fluorine or chlorine, including those substituted with different halogens, e.g., —$CH_2Cl$, —$CF_3$, —$CHF_2$, —$CH_2CF_3$, —$CF_2CF_3$, —$CF(CH_3)_2$, and the like. When the alkyl is substituted with only fluoro, it is referred to in this Application as fluoroalkyl.

"Haloalkoxy" means a —OR radical where R is haloalkyl as defined above e.g., —$OCF_3$, —$OCHF_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, or S(O)n, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group is a saturated ring and is not fused to aryl or heteroaryl ring as stated above, it is also referred to herein as saturated monocyclic heterocyclyl.

"Heterocyclylalkyl" means -(alkylene)-R where R is heterocyclyl which is a saturated or unsaturated monovalent monocyclic group of 4 to 8 ring atoms in which one or two ring atoms are heteroatom selected from N, O, or S(O)n, where n is an integer from 0 to 2, the remaining ring atoms being C. Additionally, one or two ring carbon atoms in the heterocyclyl ring can optionally be replaced by a —CO— group. More specifically the term heterocyclylalkyl includes, but is not limited to, pyrrolidin-1-ylmethyl, pyrrolidinylethyl, piperidinylmethyl, piperidinylethyl, morpholinylethyl, piperazinylethyl, tetrahydropyranylethyl, thiomorpholinoethyl, and the like.

"Heterocycloamino" means a saturated or unsaturated monovalent monocyclic group of 4 to 8 ring atoms in which one or two ring atoms are heteroatom selected from N, O, or S(O)n, where n is an integer from 0 to 2, the remaining ring atoms being C provided that at least one of the ring atoms is N. Additionally, one or two ring carbon atoms in the heterocycloamino ring can optionally be replaced by a —CO— group. Unless otherwise stated, the heterocycloamino ring can optionally be substituted with one, two, or three substituents independently selected from alkyl, hydroxyl, halo, alkoxy, amino, alkylamino, or dialkylamino.

"Heteroaryl" means a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, pyrazolyl, thienyl, thiazolyl, imidazolyl, furanyl, indolyl, isoindolyl, oxazolyl, isoxazolyl, benzothiazolyl, benzoxazolyl, benzimidazolyl, quinolinyl, isoquinolinyl, pyridinyl, pyrimidinyl, pyrazinyl, pyridazinyl, triazolyl, tetrazolyl, and the like.

The present disclosure also includes the prodrugs of compounds of Formula (I) and/or a pharmaceutically acceptable salt thereof. The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylamino-carbonyl) of hydroxy or amino functional groups in compounds of Formula (I)), amides (e.g., trifluoroacetylamino, acetylamino, and the like), and the like. Prodrugs of compounds of Formula (I) are also within the scope of this disclosure.

The present disclosure also includes protected derivatives of compounds of Formula (I) and/or a pharmaceutically acceptable salt thereof. For example, when compounds of Formula (I) contain groups such as hydroxy, carboxy, thiol or any group containing a nitrogen atom(s), these groups can be protected with a suitable protecting groups. A comprehensive list of suitable protective groups can be found in T.W. Greene, Protective Groups in Organic Synthesis, John Wiley & Sons, Inc. (1999), the disclosure of which is incorporated herein by reference in its entirety. The protected derivatives of compounds of Formula (I) can be prepared by methods well known in the art.

"Thiophenylene" refers to a disubstituted moiety of formula (a) and 2,5-thiophenylene refers to a disubstituted moiety of formula (a1):

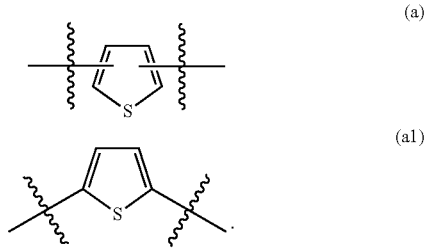

The present disclosure also includes amorphous or polymorphic forms (crystalline) and deuterated forms of compounds of Formula (I) and/or a pharmaceutically acceptable salt thereof.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, racemic forms are within the scope of this disclosure, unless the specific stereochemistry is specifically indicated.

Compounds of Formula (I) can exist as the tautomers shown below:

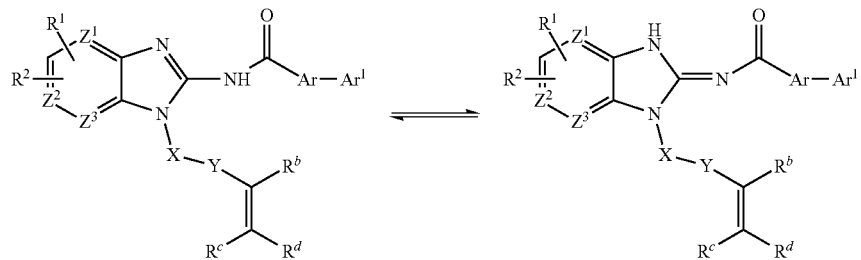

All possible tautomers are within the scope of the present disclosure. Additional, the —$CR^b$=$CR^cR^d$ group in the compound of Formula (I) can exist as cis and trans isomers. The individual cis or trans forms and mixtures thereof are within the scope of the present disclosure unless a specific isomeric form is specifically indicated. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (I) and/or a pharmaceutically acceptable salt thereof are within the scope of this disclosure.

"Mammal" as used herein means domesticated animals (such as dogs, cats, and horses), and humans. In one embodiment, mammal is a human.

"Oxo" and "carbonyl" mean =(O) and C=O, group respectively.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

"Optionally substituted aryl" means aryl as defined above which is substituted with one, two, or three substituents independently selected from alkyl, alkoxy, halo, haloalkyl, haloalkoxy, hydroxy, carboxy, alkoxycarbonyl, cyano, alkylsulfonyl, amino, alkylamino, dialkylamino, aminoalkyl or cycloalkyl.

"Optionally substituted heteroaryl" means heteroaryl as defined above which is substituted with one, two, or three substituents independently selected from alkyl, alkoxy, halo, haloalkyl, haloalkoxy, hydroxy, carboxy, alkoxycarbonyl, cyano, alkylsulfonyl, amino, alkylamino, dialkylamino, aminoalkyl or cycloalkyl.

"Optionally substituted heteroaralkyl" means -(alkylene)-R where R is optionally substituted heteroaryl as defined above.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use.

"A pharmaceutically acceptable carrier/excipient" as used in the specification and claims includes both one and more than one such excipient.

"Spiroheterocycloamino" means a bicyclic ring of 7 to 12 ring atoms and joined through one ring atom in which one or two ring atoms are heteroatom selected from N, O, or $S(O)_n$, where n is an integer from 0 to 2, the remaining ring atoms being C provided that at least one of the ring atoms is N. Additionally, one or two ring carbon atoms in the heterocycloamino ring can optionally be replaced by a —CO— group.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease;
(2) inhibiting the disease, i.e., arresting or reducing the development of the disease or its clinical symptoms; or
(3) relieving the disease, i.e., causing regression of the disease or its clinical symptoms.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated.

Representative compounds of the disclosure are provided in Table I below.

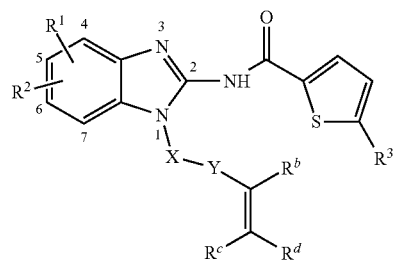

| Cpd # | $R^1$ | $R^2$ | $R^3$ | —X—Y— | $R^b$ | $R^d$ | $R^c$ | Salt | $MS^1$ |
|---|---|---|---|---|---|---|---|---|---|
| 1 | HO-CH2CH2- | H | oxazolyl-O- | pyrrolidinyl-C(O)- | CN | t-Bu | H | | 559.0 |
| 2 | cyclopropyl-CH2-NH-CH2- | H | oxazolyl-O- | pyrrolidinyl-C(O)- | CN | t-Bu | H | formate | 612.0 |
| 3 | (CH2OH)(tBu)CH-NH-CH2- | H | oxazolyl-O- | pyrrolidinyl-C(O)- | CN | t-Bu | H | formate | 658 |

-continued

| Cpd # | R¹ | R² | R³ | —X—Y— | $R^b$ | $R^d$ | $R^c$ | Salt | MS¹ |
|---|---|---|---|---|---|---|---|---|---|
| 4 | (S)-tBuCH(CH₂OH)NH– (CH₂OH with wedge, tBu) | H | 5-oxazolyl | pyrrolidin-2-yl-C(O)– | CN | t-Bu | H | | 658 |
| 5 | (S)-HOCH₂CH(Me)NH– | H | 5-oxazolyl | pyrrolidin-2-yl-C(O)– | CN | t-Bu | H | | 616 |
| 6 | (R)-HOCH₂CH(Me)NH– | H | 5-oxazolyl | pyrrolidin-2-yl-C(O)– | CN | t-Bu | H | | 616 |
| 7 | (S)-MeOCH₂CH(Me)NH– | H | 5-oxazolyl | pyrrolidin-2-yl-C(O)– | CN | t-Bu | H | | 630 |
| 8 | (R)-MeOCH₂CH(Me)NH– | H | 5-oxazolyl | pyrrolidin-2-yl-C(O)– | CN | t-Bu | H | formate | 630 |
| 9 | cyclopropyl-CH₂-NH– | H | 5-oxazolyl | pyrrolidin-2-yl-C(O)– | H | H | H | | 531 |
| 10 | (S)-HOCH₂-CH(tBu)-NH– | H | 5-oxazolyl | pyrrolidin-2-yl-C(O)– | H | H | H | | 577 |
| 11 | (R)-HOCH₂-CH(tBu)-NH– | H | 5-oxazolyl | pyrrolidin-2-yl-C(O)– | H | H | H | | 577 |

-continued

| Cpd # | R¹ | R² | R³ | —X—Y— | R$^b$ | R$^d$ | R$^c$ | Salt | MS¹ |
|---|---|---|---|---|---|---|---|---|---|
| 12 | (S)-HOCH₂-CH(NH-)-CH₃ (with wedge) | H | oxazol-5-yl | pyrrolidine-C(=O)- | H | H | H | | 535 |
| 13 | (R)-HOCH₂-CH(NH-)-CH₃ | H | oxazol-5-yl | pyrrolidine-C(=O)- | H | H | H | | 535 |
| 14 | HOC(CH₃)₂CH₂NH- | H | oxazol-5-yl | pyrrolidine-C(=O)- | H | H | H | | 535 |
| 15 | tBu-CH(Me)(NH-)- | H | oxazol-5-yl | pyrrolidine-C(=O)- | CN | t-Bu | H | | 642 |
| 16 | HOC(CH₃)₂CH₂NH- | H | oxazol-5-yl | pyrrolidine-C(=O)- | CN | t-Bu | H | formate | 630.1 |
| 17 | tetrahydropyran-4-yl-NH- | H | oxazol-5-yl | pyrrolidine-C(=O)- | CN | t-Bu | H | formate | 642.1 |
| 18 | CHF₂CH₂NH- | H | oxazol-5-yl | pyrrolidine-C(=O)- | CN | t-Bu | H | formate | 621.9 |
| 19 | 2-(methoxymethyl)pyrrolidin-1-yl-CH₂CH₂- | H | oxazol-5-yl | pyrrolidine-C(=O)- | CN | t-Bu | H | formate | 656.1 |

-continued

| Cpd # | R¹ | R² | R³ | —X—Y— | R^b | R^d | R^c | Salt | MS¹ |
|---|---|---|---|---|---|---|---|---|---|
| 20 | tetrahydrofuran-3-ylaminoethyl | H | oxazol-5-yl | pyrrolidine-2-carbonyl | CN | t-Bu | H | formate | 627.8 |
| 21 | morpholinomethyl | H | oxazol-5-yl | pyrrolidine-2-carbonyl | CN | t-Bu | H | formate | 627.8 |
| 22 | (2-(methoxymethyl)pyrrolidin-1-yl)methyl | H | oxazol-5-yl | pyrrolidine-2-carbonyl | CN | t-Bu | H | | 655.8 |
| 23 | 4-methyl-2-hydroxypentyl | H | oxazol-5-yl | pyrrolidine-2-carbonyl | CN | t-Bu | H | | 614.7 |
| 24 | isobutylaminomethyl | H | oxazol-5-yl | pyrrolidine-2-carbonyl | CN | t-Bu | H | | 613.8 |
| 25 | cyclopropylmethylaminomethyl | H | oxazol-5-yl | pyrrolidine-2-carbonyl | CN | c-Pr | H | | 595.8 |
| 26 | cyclopropylmethylaminomethyl | H | oxazol-5-yl | pyrrolidine-2-carbonyl | CN | i-Pr | H | | 597.7 |
| 27 | tBu-CH₂-NH-C(CH₃)₂- | H | oxazol-5-yl | pyrrolidine-2-carbonyl | CN | t-Bu | H | | 627.8 |

-continued

| Cpd # | R¹ | R² | R³ | —X—Y— | Rᵇ | Rᵈ | Rᶜ | Salt | MS¹ |
|---|---|---|---|---|---|---|---|---|---|
| 28 | tBu-CH(Me)-NH-C(Me)₂- | H | 5-oxazolyl | (S)-pyrrolidine-2-yl-C(O)- | H | H | H | | 560.8 |
| 29 | HO-CH₂-CH< | H | 2-fluoropyridin-4-yl | (S)-pyrrolidine-2-yl-C(O)- | CN | t-Bu | H | | 586.7 |
| 30 | HO-CH₂-CH< | H | 5-oxazolyl | (S)-pyrrolidine-2-yl-C(O)- | CN | c-Pr | H | | 542.6 |
| 31 | cyclopropyl-CH₂-NH-CH< | H | 2-fluoropyridin-4-yl | (S)-pyrrolidine-2-yl-C(O)- | CN | t-Bu | H | formate | 639.8 |
| 32 | HO-CH₂-CH< | H | 2-methyloxazol-5-yl | (S)-pyrrolidine-2-yl-C(O)- | CN | t-Bu | H | | 572.7 |
| 33 | HO-CH₂-CH< | H | 5-oxazolyl | (S)-pyrrolidine-2-yl-C(O)- | CN | i-Pr | H | | 544.7 |
| 34 | MeO-CH₂-CH(*)-NH- | H | 5-oxazolyl | (S)-pyrrolidine-2-yl-C(O)- | CN | i-Pr | H | formate | 615.7 |
| 35 | cyclopropyl-CH₂-NH-CH< | H | 2-methyloxazol-5-yl | (S)-pyrrolidine-2-yl-C(O)- | CN | t-Bu | H | formate | 625.8 |

| Cpd # | R¹ | R² | R³ | —X—Y— | Rᵇ | Rᵈ | Rᶜ | Salt | MS¹ |
|---|---|---|---|---|---|---|---|---|---|
| 36 | 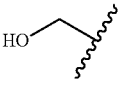 | H | 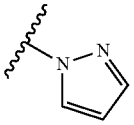 [SMILES: *n1cccn1] | 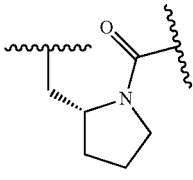 [SMILES: *C[C@H]1CCCN1C(*)=O] | CN | t-Bu | H | | 555.7 |
| 37 | 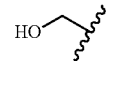 | H | 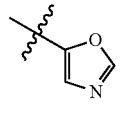 | 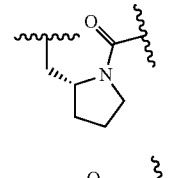 | CN | 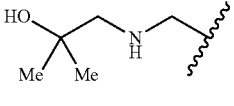 | H | | 556.7 |
| 38 | 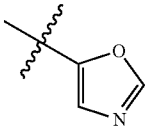 [SMILES: *c1cnco1] | H | 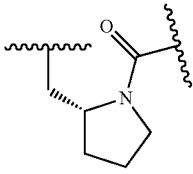 [SMILES: *C[C@H]1CCCN1C(*)=O] | 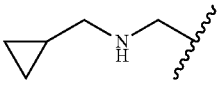 | CN | c-Pr | H | formate | 613.7 |
| 39 | 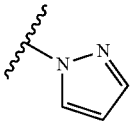 [SMILES: *n1cccn1] | H | 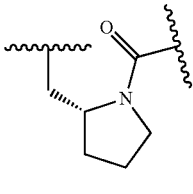 [SMILES: *C[C@H]1CCCN1C(*)=O] | 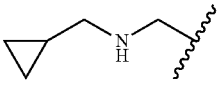 | CN | t-Bu | H | formate | 610.7 |
| 40 | 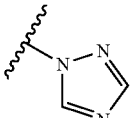 | H | 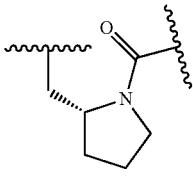 [SMILES: *C[C@H]1CCCN1C(*)=O] | 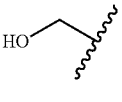 | CN | t-Bu | H | formate | 611.7 |
| 41 | 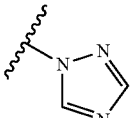 | H | 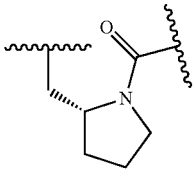 [SMILES: *C[C@H]1CCCN1C(*)=O] | 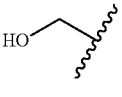 | CN | t-Bu | H | | 555.8 |
| 42 | 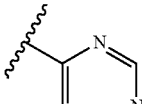 | H | 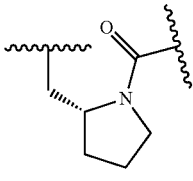 [SMILES: *C[C@H]1CCCN1C(*)=O] | 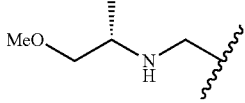 | CN | t-Bu | H | | 569.7 |
| 43 | 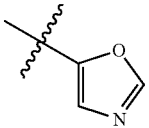 [SMILES: *c1cnco1] | H | 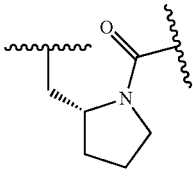 [SMILES: *C[C@H]1CCCN1C(*)=O] | 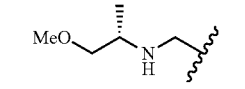 [SMILES: *CN[C@@H](C)COC] | CN | c-Pr | H | | 613.7 |
| 44 | 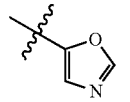 | H | | 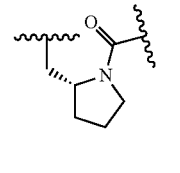 [SMILES: *C[C@H]1CCCN1C(*)=O] | CN | Me | H | formate | 627.8 |

-continued
| Cpd # | R¹ | R² | R³ | —X—Y— | $R^b$ | $R^d$ | $R^c$ | Salt | MS¹ |
|---|---|---|---|---|---|---|---|---|---|
| 45 | 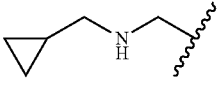 | H | 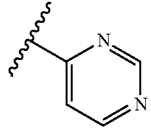 [SMILES: *c1ccncn1] | 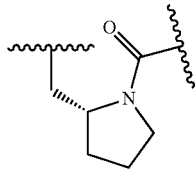 [SMILES: *C[C@H]1CCCN1C(*)=O] | CN | t-Bu | H | formate | 622.8 |
| 46 | 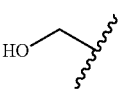 | H | 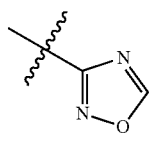 [SMILES: *c1ncon1] | 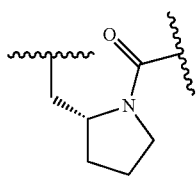 [SMILES: *C[C@H]1CCCN1C(*)=O] | CN | t-Bu | H | | 559.7 |
| 47 | 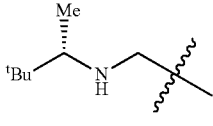 | H | 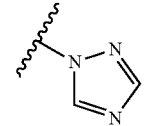 | 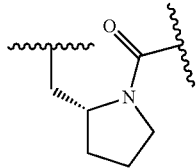 [SMILES: *C[C@H]1CCCN1C(*)=O] | CN | t-Bu | H | | 641.8 |
| 48 | 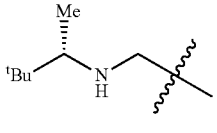 | H | 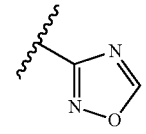 [SMILES: *c1ncon1] | 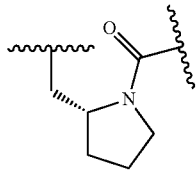 [SMILES: *C[C@H]1CCCN1C(*)=O] | CN | t-Bu | H | | 642.8 |
| 49 | 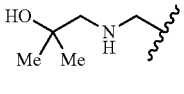 | H | 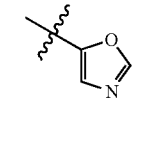 | 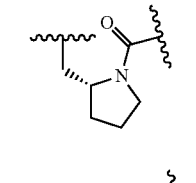 | CN | 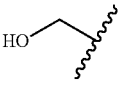 | H | formate | 627.8 |
| 50 | 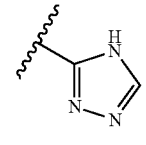 [SMILES: *c1nnc[nH]1] | H | 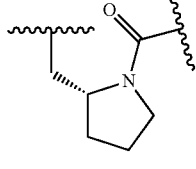 | 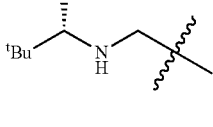 | CN | t-Bu | H | | 558.8 |
| 51 | 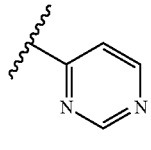 [SMILES: *c1ccncn1] | H | 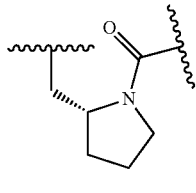 [SMILES: *C[C@H]1CCCN1C(*)=O] | 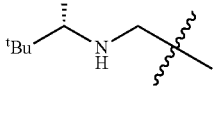 | CN | t-Bu | H | | 652.9 |
| 52 | 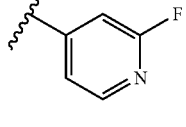 | H | 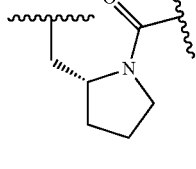 | | CN | t-Bu | H | | 669.9. |

| Cpd # | R¹ | R² | R³ | —X—Y— | R^b | R^d | R^c | Salt | MS¹ |
|---|---|---|---|---|---|---|---|---|---|
| 53 | (S)-tBu-CH(Me)-NH-CH2- | H | pyrazin-2-yl | -CH2-(pyrrolidin-2-yl)-C(O)- | CN | t-Bu | H | | 653.0 |
| 54 | (S)-tBu-CH(Me)-NH-CH2- | H | oxazol-5-yl | -CH2-C(Me)2-CH2-N(Me)-C(O)- | CN | t-Bu | H | | 658.8 |
| 55 | (S)-tBu-CH(Me)-NH-CH2- | H | oxazol-5-yl | -CH2-C(Me)2-CH2-N(Me)-C(O)- | H | H | H | | 577.5 |
| 56 | HO-C(Me)2-CH2-NH-CH2- | H | oxazol-5-yl | -CH2-(pyrrolidin-2-yl)-C(O)- | CN | i-Pr | H | formate | 615.6 |
| 57 | (S)-tBu-CH(Me)-NH-CH2- | H | oxazol-5-yl | -C(Me)2-NH-C(O)- | CN | t-Bu | H | | 630.3 |
| 58 | (S)-tBu-CH(Me)-NH-CH2- | H | oxazol-5-yl | -C(Me)2-NH-C(O)- | H | H | H | | 549.2 |
| 59 | (S)-tBu-CH(Me)-NH-CH2- | H | oxazol-5-yl | -CH2-(piperidin-3-yl)-C(O)- | CN | t-Bu | H | | 656 |

¹MS + mass spectrum [M]⁺

Other compounds within the scope of the invention are in the following table.

| Cpd # | R¹ | R² | R³ | —X—Y— | R^b | R^d | R^c |
|---|---|---|---|---|---|---|---|
| 60 | oxazol-2-yl-CH2-NH-CH2- | H | oxazol-5-yl | -CH2-(pyrrolidin-2-yl)-C(O)- | CN | t-Bu | H |

-continued
| Cpd # | R¹ | R² | R³ | —X—Y— | R^b | R^d | R^c |
|---|---|---|---|---|---|---|---|
| 61 | 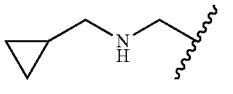 [SMILES: *CNCC1CC1] | H | 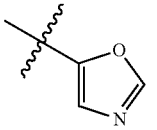 | 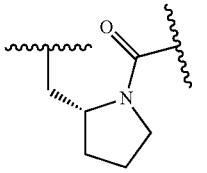 [SMILES: *C[C@H]1CCCN1C(*)=O] | CN |  | H |
| 62 | 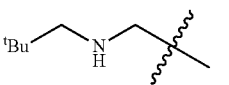 | H | 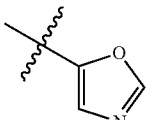 | 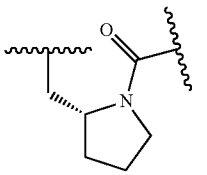 [SMILES: *C[C@H]1CCCN1C(*)=O] | CN | i-Pr | H |
| 63 | 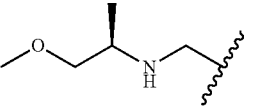 [SMILES: *CN[C@H](C)COC] | H | 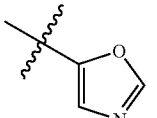 | 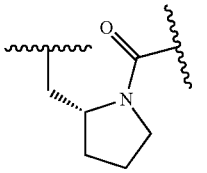 [SMILES: *C[C@H]1CCCN1C(*)=O] | H | H | H |
| 64 | 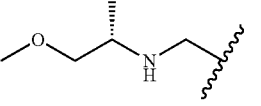 | H | 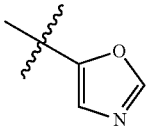 [SMILES: *c1cnco1] | 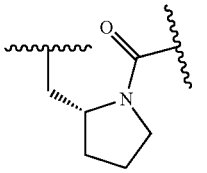 | H | H | H |
| 65 | 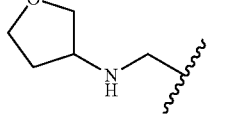 | H | 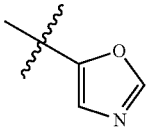 | 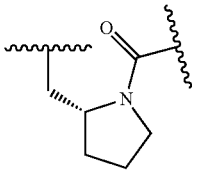 [SMILES: *C[C@H]1CCCN1C(*)=O] | H | H | H |
| 66 | 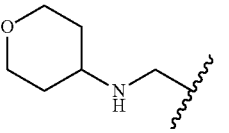 [SMILES: *CNC1CCOCC1] | H | 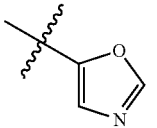 [SMILES: *c1cnco1] | 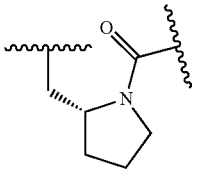 [SMILES: *C[C@H]1CCCN1C(*)=O] | H | H | H |
| 67 | 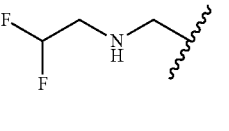 [SMILES: *CNCC(F)F] | H | 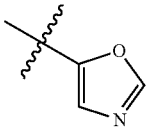 [SMILES: *c1cnco1] | 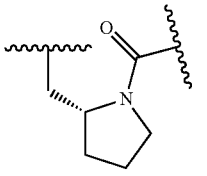 [SMILES: *C[C@H]1CCCN1C(*)=O] | H | H | H |
| 68 | 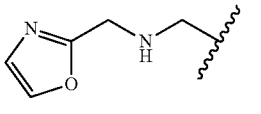 [SMILES: *CNCc1ncco1] | H | 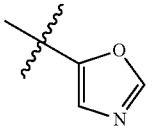 [SMILES: *c1cnco1] | 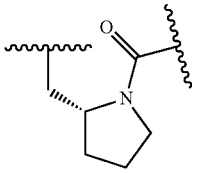 [SMILES: *C[C@H]1CCCN1C(*)=O] | H | H | H |

| Cpd # | R¹ | R² | R³ | —X—Y— | $R^b$ | $R^d$ | $R^c$ |
|---|---|---|---|---|---|---|---|
| 69 | morpholinoethyl | H | oxazol-5-yl | pyrrolidinyl carbonyl | H | H | H |
| 70 | (methoxymethyl)pyrrolidinylmethyl | H | oxazol-5-yl | pyrrolidinyl carbonyl | H | H | H |
| 71 | (methoxymethyl)pyrrolidinylmethyl | H | oxazol-5-yl | pyrrolidinyl carbonyl | H | H | H |

Compounds are named as:
1. (R)-N-(1-((1-(2-cyano-4,4-dimethylpent-2-enoyl)pyrrolidin-2-yl)methyl)-5-(hydroxymethyl)-1H-benzo[d]imidazol-2-yl)-5-(oxazol-5-yl)thiophene-2-carboxamide;
2. (R)-N-(1-((1-(2-cyano-4,4-dimethylpent-2-enoyl)pyrrolidin-2-yl)methyl)-5-(((cyclopropyl-methyl)amino)methyl)-1H-benzo[d]imidazol-2-yl)-5-(oxazol-5-yl)thiophene-2-carboxamide;
3. N-(1-(((R)-1-(2-cyano-4,4-dimethylpent-2-enoyl)pyrrolidin-2-yl)methyl)-5-((((S)-1-hydroxy-3,3-dimethylbutan-2-yl)amino)methyl)-1H-benzo[d]imidazol-2-yl)-5-(oxazol-5-yl)thiophene-2-carboxamide;
4. N-(1-(((R)-1-(2-cyano-4,4-dimethylpent-2-enoyl)pyrrolidin-2-yl)methyl)-5-((((R)-1-hydroxy-3,3-dimethylbutan-2-yl)amino)methyl)-1H-benzo[d]imidazol-2-yl)-5-(oxazol-5-yl)thiophene-2-carboxamide;
5. N-(1-(((R)-1-(2-cyano-4,4-dimethylpent-2-enoyl)pyrrolidin-2-yl)methyl)-5-((((S)-1-hydroxypropan-2-yl)amino)methyl)-1H-benzo[d]imidazol-2-yl)-5-(oxazol-5-yl)thiophene-2-carboxamide;
6. N-(1-(((R)-1-(2-cyano-4,4-dimethylpent-2-enoyl)pyrrolidin-2-yl)methyl)-5-((((R)-1-hydroxypropan-2-yl)amino)methyl)-1H-benzo[d]imidazol-2-yl)-5-(oxazol-5-yl)thiophene-2-carboxamide;
7. N-(1-(((R)-1-(2-cyano-4,4-dimethylpent-2-enoyl)pyrrolidin-2-yl)methyl)-5-((((R)-1-methoxypropan-2-yl)amino)methyl)-1H-benzo[d]imidazol-2-yl)-5-(oxazol-5-yl)thiophene-2-carboxamide;
8. N-(1-(((R)-1-(2-cyano-4,4-dimethylpent-2-enoyl)pyrrolidin-2-yl)methyl)-5-((((S)-1-methoxypropan-2-yl)amino)methyl)-1H-benzo[d]imidazol-2-yl)-5-(oxazol-5-yl)thiophene-2-carboxamide;
9. (R)-N-(1-((1-acryloylpyrrolidin-2-yl)methyl)-5-(((cyclopropylmethyl)amino)methyl)-1H-benzo[d]imidazol-2-yl)-5-(oxazol-5-yl)thiophene-2-carboxamide;
10. N-(1-(((R)-1-acryloylpyrrolidin-2-yl)methyl)-5-((((S)-1-hydroxy-3,3-dimethylbutan-2-yl)amino)methyl)-1H-benzo[d]imidazol-2-yl)-5-(oxazol-5-yl)thiophene-2-carboxamide;
11. N-(1-(((R)-1-acryloylpyrrolidin-2-yl)methyl)-5-((((R)-1-hydroxy-3,3-dimethylbutan-2-yl)amino)methyl)-1H-benzo[d]imidazol-2-yl)-5-(oxazol-5-yl)thiophene-2-carboxamide;
12. N-(1-(((R)-1-acryloylpyrrolidin-2-yl)methyl)-5-((((S)-1-hydroxypropan-2-yl)amino)methyl)-1H-benzo[d]imidazol-2-yl)-5-(oxazol-5-yl)thiophene-2-carboxamide;
13. N-(1-(((R)-1-acryloylpyrrolidin-2-yl)methyl)-5-((((R)-1-hydroxypropan-2-yl)amino)methyl)-1H-benzo[d]imidazol-2-yl)-5-(oxazol-5-yl)thiophene-2-carboxamide;
14. (R)-N-(1-((1-acryloylpyrrolidin-2-yl)methyl)-5-(((2-hydroxy-2-methylpropyl)amino)methyl)-1H-benzo[d]imidazol-2-yl)-5-(oxazol-5-yl)thiophene-2-carboxamide;
15. N-(1-(((R)-1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)-5-(oxazol-5-yl)thiophene-2-carboxamide;
16. (R)-N-(1-((1-(2-cyano-4,4-dimethylpent-2-enoyl)pyrrolidin-2-yl)methyl)-5-(((2-hydroxy-2-methylpropyl)amino)methyl)-1H-benzo[d]imidazol-2-yl)-5-(oxazol-5-yl)thiophene-2-carboxamide;
17. (R)-N-(1-((1-(2-cyano-4,4-dimethylpent-2-enoyl)pyrrolidin-2-yl)methyl)-5-(((tetrahydro-2H-pyran-4-yl)amino)methyl)-1H-benzo[d]imidazol-2-yl)-5-(oxazol-5-yl)thiophene-2-carboxamide;
18. (R)-N-(1-((1-(2-cyano-4,4-dimethylpent-2-enoyl)pyrrolidin-2-yl)methyl)-5-(((2,2-difluoroethyl)amino)methyl)-1H-benzo[d]imidazol-2-yl)-5-(oxazol-5-yl)thiophene-2-carboxamide;
19. N-(1-(((R)-1-(2-cyano-4,4-dimethylpent-2-enoyl)pyrrolidin-2-yl)methyl)-5-(((S)-2-(methoxymethyl)pyrrolidin-1-yl)methyl)-1H-benzo[d]imidazol-2-yl)-5-(oxazol-5-yl)thiophene-2-carboxamide;
20. N-(1-(((R)-1-(2-cyano-4,4-dimethylpent-2-enoyl)pyrrolidin-2-yl)methyl)-5-(((tetrahydrofuran-3-yl)amino)methyl)-1H-benzo[d]imidazol-2-yl)-5-(oxazol-5-yl)thiophene-2-carboxamide;
21. (R)-N-(1-((1-(2-cyano-4,4-dimethylpent-2-enoyl)pyrrolidin-2-yl)methyl)-5-(morpholinomethyl)-1H-benzo[d]imidazol-2-yl)-5-(oxazol-5-yl)thiophene-2-carboxamide;

22. N-(1-(((R)-1-(2-cyano-4,4-dimethylpent-2-enoyl)pyrrolidin-2-yl)methyl)-5-(((R)-2-(methoxymethyl)pyrrolidin-1-yl)methyl)-1H-benzo[d]imidazol-2-yl)-5-(oxazol-5-yl)thiophene-2-carboxamide;
23. N-(1-(((R)-1-(2-cyano-4,4-dimethylpent-2-enoyl)pyrrolidin-2-yl)methyl)-5-(1-hydroxy-3-methylbutyl)-1H-benzo[d]imidazol-2-yl)-5-(oxazol-5-yl)thiophene-2-carboxamide;
24. (R)-N-(1-((1-(2-cyano-4,4-dimethylpent-2-enoyl)pyrrolidin-2-yl)methyl)-5-((isobutyl-amino)methyl)-1H-benzo[d]imidazol-2-yl)-5-(oxazol-5-yl)thiophene-2-carboxamide;
25. (R)-N-(1-(((1-(2-cyano-3-cyclopropylacryloyl)pyrrolidin-2-yl)methyl)-5-(((cyclopropyl-methyl)amino)methyl)-1H-benzo[d]imidazol-2-yl)-5-(oxazol-5-yl)thiophene-2-carboxamide;
26. (R)-N-(1-((1-(2-cyano-4-methylpent-2-enoyl)pyrrolidin-2-yl)methyl)-5-(((cyclopropyl-methyl)amino)methyl)-1H-benzo[d]imidazol-2-yl)-5-(oxazol-5-yl)thiophene-2-carboxamide;
27. (R)-N-(1-((1-(2-cyano-4,4-dimethylpent-2-enoyl)pyrrolidin-2-yl)methyl)-5-((neopentylamino)methyl)-1H-benzo[d]imidazol-2-yl)-5-(oxazol-5-yl)thiophene-2-carboxamide;
28. N-(1-(((R)-1-acryloylpyrrolidin-2-yl)methyl)-5-((((S)-3,3-dimethylbutan-2-yl)amino)methyl)-1H-benzo[d]imidazol-2-yl)-5-(oxazol-5-yl)thiophene-2-carboxamide;
29. N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(2-fluoropyridin-4-yl)thiophene-2-carboxamide;
30. N-((E)-1-(((R)-1-((E)-2-cyano-3-cyclopropylacryloyl)pyrrolidin-2-yl)methyl)-5-(hydroxymethyl)-1,3-dihydro-2H-benzo[d]imidazol-2-ylidene)-5-(oxazol-5-yl)thiophene-2-carboxamide;
31. N-((E)-1-(((R)-1-((E)-2-cyano-4,4-dimethylpent-2-enoyl)pyrrolidin-2-yl)methyl)-5-(((cyclopropylmethyl)amino)methyl)-1,3-dihydro-2H-benzo[d]imidazol-2-ylidene)-5-(2-fluoropyridin-4-yl)thiophene-2-carboxamide;
32. N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(2-methyloxazol-5-yl)thiophene-2-carboxamide;
33. N-((E)-1-(((R)-1-((E)-2-cyano-4-methylpent-2-enoyl)pyrrolidin-2-yl)methyl)-5-(hydroxymethyl)-1,3-dihydro-2H-benzo[d]imidazol-2-ylidene)-5-(oxazol-5-yl)thiophene-2-carboxamide;
34. N-((E)-1-(((R)-1-((E)-2-cyano-4-methylpent-2-enoyl)pyrrolidin-2-yl)methyl)-5-((((S)-1-methoxypropan-2-yl)amino)methyl)-1,3-dihydro-2H-benzo[d]imidazol-2-ylidene)-5-(oxazol-5-yl)thiophene-2-carboxamide;
35. N-((E)-1-(((R)-1-((E)-2-cyano-4,4-dimethylpent-2-enoyl)pyrrolidin-2-yl)methyl)-5-(((cyclopropylmethyl)amino)methyl)-1,3-dihydro-2H-benzo[d]imidazol-2-ylidene)-5-(2-methyloxazol-5-yl)thiophene-2-carboxamide;
36. N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(1H-pyrazol-1-yl)thiophene-2-carboxamide;
37. N-((E)-1-(((R)-1-((E)-2-cyano-3-(1-methylcyclopropyl)acryloyl)pyrrolidin-2-yl)methyl)-5-(hydroxymethyl)-1,3-dihydro-2H-benzo[d]imidazol-2-ylidene)-5-(oxazol-5-yl)thiophene-2-carboxamide;
38. N-((E)-1-(((R)-1-((E)-2-cyano-3-cyclopropylacryloyl)pyrrolidin-2-yl)methyl)-5-(((2-hydroxy-2-methylpropyl)amino)methyl)-1,3-dihydro-2H-benzo[d]imidazol-2-ylidene)-5-(oxazol-5-yl)thiophene-2-carboxamide;
39. N-((E)-1-(((R)-1-((E)-2-cyano-4,4-dimethylpent-2-enoyl)pyrrolidin-2-yl)methyl)-5-(((cyclopropylmethyl)amino)methyl)-1,3-dihydro-2H-benzo[d]imidazol-2-ylidene)-5-(1H-pyrazol-1-yl)thiophene-2-carboxamide;
40. N-((E)-1-(((R)-1-((E)-2-cyano-4,4-dimethylpent-2-enoyl)pyrrolidin-2-yl)methyl)-5-(((cyclopropylmethyl)amino)methyl)-1,3-dihydro-2H-benzo[d]imidazol-2-ylidene)-5-(1H-1,2,4-triazol-1-yl)thiophene-2-carboxamide;
41. N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(1H-1,2,4-triazol-1-yl)thiophene-2-carboxamide;
42. N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(pyrimidin-4-yl)thiophene-2-carboxamide;
43. N-((E)-1-(((R)-1-((E)-2-cyano-3-cyclopropylacryloyl)pyrrolidin-2-yl)methyl)-5-(((((S)-1-methoxypropan-2-yl)amino)methyl)-1,3-dihydro-2H-benzo[d]imidazol-2-ylidene)-5-(oxazol-5-yl)thiophene-2-carboxamide;
44. N-((E)-1-(((R)-1-((E)-2-cyano-3-(1-methylcyclopropyl)acryloyl)pyrrolidin-2-yl)methyl)-5-(((((S)-1-methoxypropan-2-yl)amino)methyl)-1,3-dihydro-2H-benzo[d]imidazol-2-ylidene)-5-(oxazol-5-yl)thiophene-2-carboxamide;
45. N-((E)-1-(((R)-1-((E)-2-cyano-4,4-dimethylpent-2-enoyl)pyrrolidin-2-yl)methyl)-5-(((cyclopropylmethyl)amino)methyl)-1,3-dihydro-2H-benzo[d]imidazol-2-ylidene)-5-(pyrimidin-4-yl)thiophene-2-carboxamide;
46. N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(1,2,4-oxadiazol-3-yl)thiophene-2-carboxamide;
47. N-((E)-1-(((R)-1-((E)-2-cyano-4,4-dimethylpent-2-enoyl)pyrrolidin-2-yl)methyl)-5-(((((S)-3,3-dimethylbutan-2-yl)amino)methyl)-1,3-dihydro-2H-benzo[d]imidazol-2-ylidene)-5-(1H-1,2,4-triazol-1-yl)thiophene-2-carboxamide;
48. N-((E)-1-(((R)-1-((E)-2-cyano-4,4-dimethylpent-2-enoyl)pyrrolidin-2-yl)methyl)-5-(((((S)-3,3-dimethylbutan-2-yl)amino)methyl)-1,3-dihydro-2H-benzo[d]imidazol-2-ylidene)-5-(1,2,4-oxadiazol-3-yl)thiophene-2-carboxamide;
49. N-((E)-1-(((R)-1-((E)-2-cyano-3-(1-methylcyclopropyl)acryloyl)pyrrolidin-2-yl)methyl)-5-(((2-hydroxy-2-methylpropyl)amino)methyl)-1,3-dihydro-2H-benzo[d]imidazol-2-ylidene)-5-(oxazol-5-yl)thiophene-2-carboxamide;
50. N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(4H-1,2,4-triazol-3-yl)thiophene-2-carboxamide;
51. N-((E)-1-(((R)-1-((E)-2-cyano-4,4-dimethylpent-2-enoyl)pyrrolidin-2-yl)methyl)-5-(((3,3-dimethylbutan-2-yl)amino)methyl)-1,3-dihydro-2H-benzo[d]imidazol-2-ylidene)-5-(pyrimidin-4-yl)thiophene-2-carboxamide;
52. N-((E)-1-(((R)-1-((E)-2-cyano-4,4-dimethylpent-2-enoyl)pyrrolidin-2-yl)methyl)-5-(((((S)-3,3-dimethylbutan-2-yl)amino)methyl)-1,3-dihydro-2H-benzo[d]imidazol-2-ylidene)-5-(2-fluoropyridin-4-yl)thiophene-2-carboxamide;
53. N-((E)-1-(((R)-1-((E)-2-cyano-4,4-dimethylpent-2-enoyl)pyrrolidin-2-yl)methyl)-5-(((((S)-3,3-dimethylbutan-2-yl)amino)methyl)-1,3-dihydro-2H-benzo[d]imidazol-2-ylidene)-5-(pyrazin-2-yl)thiophene-2-carboxamide;

54. N-((E)-1-(2-((E)-2-cyano-N,4,4-trimethylpent-2-enamido)-2-methylpropyl)-5-((((S)-3,3-dimethylbutan-2-yl)amino)methyl)-1,3-dihydro-2H-benzo[d]imidazol-2-ylidene)-5-(oxazol-5-yl)thiophene-2-carboxamide;
55. (S,E)-N-(1-(2-(2-cyano-N-methylacrylamido)-2-methylpropyl)-5-(((3,3-dimethylbutan-2-yl)amino)methyl)-1,3-dihydro-2H-benzo[d]imidazol-2-ylidene)-5-(oxazol-5-yl)thiophene-2-carboxamide;
56. N-((E)-1-(2-((E)-2-cyano-N,4-dimethylpent-2-enamido)-2-methylpropyl)-5-(((2-hydroxy-2-methylpropyl)amino)methyl)-1,3-dihydro-2H-benzo[d]imidazol-2-ylidene)-5-(oxazol-5-yl)thiophene-2-carboxamide;
57. N-((E)-1-(2-((E)-2-cyano-4,4-dimethylpent-2-enamido)-2-methylpropyl)-5-((((S)-3,3-dimethylbutan-2-yl)amino)methyl)-1,3-dihydro-2H-benzo[d]imidazol-2-ylidene)-5-(oxazol-5-yl)thiophene-2-carboxamide;
58. (S,E)-N-(1-(2-acrylamido-2-methylpropyl)-5-(((3,3-dimethylbutan-2-yl)amino)methyl)-1,3-dihydro-2H-benzo[d]imidazol-2-ylidene)-5-(oxazol-5-yl)thiophene-2-carboxamide; or,
59. N-((E)-1-(((R)-1-((Z)-2-cyano-4,4-dimethylpent-2-enoyl)piperidin-3-yl)methyl)-5-((((S)-3,3-dimethylbutan-2-yl)amino)methyl)-1,3-dihydro-2H-benzo[d]imidazol-2-ylidene)-5-(oxazol-5-yl)thiophene-2-carboxamide;
or, an E or Z isomer thereof; or a pharmaceutically acceptable salt of any of the foregoing compounds.

Other representative compounds of the disclosure are:
60. (R)-N-(1-((1-(2-cyano-4,4-dimethylpent-2-enoyl)pyrrolidin-2-yl)methyl)-5-(((oxazol-2-ylmethyl)amino)methyl)-1H-benzo[d]imidazol-2-yl)-5-(oxazol-5-yl)thiophene-2-carboxamide;
61. (R)-N-(1-((1-(2-cyano-3-(1-methylcyclopropyl)acryloyl)pyrrolidin-2-yl)methyl)-5-(((cyclopropylmethyl)amino)methyl)-1H-benzo[d]imidazol-2-yl)-5-(oxazol-5-yl)thiophene-2-carboxamide;
62. (R)-N-(1-((1-(2-cyano-3-(1-methylcyclopropyl)acryloyl)pyrrolidin-2-yl)methyl)-5-(((cyclopropylmethyl)amino)methyl)-1H-benzo[d]imidazol-2-yl)-5-(oxazol-5-yl)thiophene-2-carboxamide
63. N-(1-(((R)-1-acryloylpyrrolidin-2-yl)methyl)-5-((((R)-1-methoxypropan-2-yl)amino)methyl)-1H-benzo[d]imidazol-2-yl)-5-(oxazol-5-yl)thiophene-2-carboxamide;
64. N-(1-(((R)-1-acryloylpyrrolidin-2-yl)methyl)-5-((((S)-1-methoxypropan-2-yl)amino)methyl)-1H-benzo[d]imidazol-2-yl)-5-(oxazol-5-yl)thiophene-2-carboxamide;
65. N-(1-(((R)-1-acryloylpyrrolidin-2-yl)methyl)-5-(((tetrahydrofuran-3-yl)amino)methyl)-1H-benzo[d]imidazol-2-yl)-5-(oxazol-5-yl)thiophene-2-carboxamide;
66. (R)-N-(1-((1-acryloylpyrrolidin-2-yl)methyl)-5-(((tetrahydro-2H-pyran-4-yl)amino)methyl)-1H-benzo[d]imidazol-2-yl)-5-(oxazol-5-yl)thiophene-2-carboxamide;
67. (R)-N-(1-((1-acryloylpyrrolidin-2-yl)methyl)-5-(((2,2-difluoroethyl)amino)methyl)-1H-benzo[d]imidazol-2-yl)-5-(oxazol-5-yl)thiophene-2-carboxamide;
68. (R)-N-(1-((1-acryloylpyrrolidin-2-yl)methyl)-5-(((oxazol-2-ylmethyl)amino)methyl)-1H-benzo[d]imidazol-2-yl)-5-(oxazol-5-yl)thiophene-2-carboxamide;
69. (R)-N-(1-((1-acryloylpyrrolidin-2-yl)methyl)-5-(morpholinomethyl)-1H-benzo[d]imidazol-2-yl)-5-(oxazol-5-yl)thiophene-2-carboxamide;
70. N-(1-(((R)-1-acryloylpyrrolidin-2-yl)methyl)-5-(((S)-2-(methoxymethyl)pyrrolidin-1-yl)methyl)-1H-benzo[d]imidazol-2-yl)-5-(oxazol-5-yl)thiophene-2-carboxamide;
71. N-(1-(((R)-1-acryloylpyrrolidin-2-yl)methyl)-5-(((R)-2-(methoxymethyl)pyrrolidin-1-yl)methyl)-1H-benzo[d]imidazol-2-yl)-5-(oxazol-5-yl)thiophene-2-carboxamide;

or an E or Z isomer thereof; or a pharmaceutically acceptable salt of any of the forgoing compounds.

Other representative compounds of the disclosure are:
72. N-(1-(((R)-1-(2-cyano-4,4-dimethylpent-2-enoyl)pyrrolidin-2-yl)methyl)-5-(1-hydroxy-3-methylbutyl)-1H-benzo[d]imidazol-2-yl)-5-(1H-pyrazol-1-yl)thiophene-2-carboxamide;
73. N-(1-(((R)-1-(2-cyano-4,4-dimethylpent-2-enoyl)pyrrolidin-2-yl)methyl)-5-(1-hydroxy-3-methylbutyl)-1H-benzo[d]imidazol-2-yl)-5-(2-fluoropyridin-4-yl)thiophene-2-carboxamide;
74. (R)-N-(1-((1-(2-cyano-4,4-dimethylpent-2-enoyl)pyrrolidin-2-yl)methyl)-5-(hydroxymethyl)-1H-benzo[d]imidazol-2-yl)-5-(1H-pyrazol-1-yl)thiophene-2-carboxamide;
75. (R)-N-(1-((1-(2-cyano-4,4-dimethylpent-2-enoyl)pyrrolidin-2-yl)methyl)-5-(hydroxymethyl)-1H-benzo[d]imidazol-2-yl)-5-(2-fluoropyridin-4-yl)thiophene-2-carboxamide;
76. (R)-N-(1-((1-(2-cyano-4,4-dimethylpent-2-enoyl)pyrrolidin-2-yl)methyl)-5-(2-hydroxypropan-2-yl)-1H-benzo[d]imidazol-2-yl)-5-(1H-pyrazol-1-yl)thiophene-2-carboxamide;
77. (R)-N-(1-((1-(2-cyano-4,4-dimethylpent-2-enoyl)pyrrolidin-2-yl)methyl)-5-(2-hydroxypropan-2-yl)-1H-benzo[d]imidazol-2-yl)-5-(2-fluoropyridin-4-yl)thiophene-2-carboxamide;
78. (R)-N-(1-((1-(2-cyano-4,4-dimethylpent-2-enoyl)pyrrolidin-2-yl)methyl)-5-((isobutylamino)methyl)-1H-benzo[d]imidazol-2-yl)-5-(pyridazin-3-yl)thiophene-2-carboxamide;
79. (R)-N-(1-((1-(2-cyano-4,4-dimethylpent-2-enoyl)pyrrolidin-2-yl)methyl)-5-((isobutylamino)methyl)-1H-benzo[d]imidazol-2-yl)-5-(2-methyloxazol-5-yl)thiophene-2-carboxamide;
80. (R)-N-(1-((1-(2-cyano-4,4-dimethylpent-2-enoyl)pyrrolidin-2-yl)methyl)-5-((isobutylamino)-methyl)-1H-benzo[d]imidazol-2-yl)-5-(1H-pyrazol-1-yl)thiophene-2-carboxamide;
81. (R)-N-(1-((1-(2-cyano-4,4-dimethylpent-2-enoyl)pyrrolidin-2-yl)methyl)-5-((isobutylamino)methyl)-1H-benzo[d]imidazol-2-yl)-5-(2-fluoropyridin-4-yl)thiophene-2-carboxamide;
82. (R)-N-(1-((1-(2-cyano-4,4-dimethylpent-2-enoyl)pyrrolidin-2-yl)methyl)-5-(((cyclopropylmethyl)amino)methyl)-1H-benzo[d]imidazol-2-yl)-5-(pyridazin-3-yl)thiophene-2-carboxamide;
83. (R)-N-(1-((1-(2-cyano-4,4-dimethylpent-2-enoyl)pyrrolidin-2-yl)methyl)-5-((neopentylamino)methyl)-1H-benzo[d]imidazol-2-yl)-5-(2-methyloxazol-5-yl)thiophene-2-carboxamide;
84. (R)-N-(1-((1-(2-cyano-4,4-dimethylpent-2-enoyl)pyrrolidin-2-yl)methyl)-5-((neopentylamino)methyl)-1H-benzo[d]imidazol-2-yl)-5-(1H-pyrazol-1-yl)thiophene-2-carboxamide;
85. (R)-N-(1-((1-(2-cyano-4,4-dimethylpent-2-enoyl)pyrrolidin-2-yl)methyl)-5-(((2,2-difluoroethyl)amino)methyl)-1H-benzo[d]imidazol-2-yl)-5-(pyridazin-3-yl)thiophene-2-carboxamide;
86. (R)-N-(1-((1-(2-cyano-4,4-dimethylpent-2-enoyl)pyrrolidin-2-yl)methyl)-5-(((2,2-difluoroethyl)amino)methyl)-1H-benzo[d]imidazol-2-yl)-5-(2-methyloxazol-5-yl)thiophene-2-carboxamide;
87. (R)-N-(1-((1-(2-cyano-4,4-dimethylpent-2-enoyl)pyrrolidin-2-yl)methyl)-5-(((2,2-difluoroethyl)amino)methyl)-1H-benzo[d]imidazol-2-yl)-5-(1H-pyrazol-1-yl)thiophene-2-carboxamide;

88. (R)-N-(1-((1-(2-cyano-4,4-dimethylpent-2-enoyl)pyrrolidin-2-yl)methyl)-5-(((2,2-difluoroethyl)amino)methyl)-1H-benzo[d]imidazol-2-yl)-5-(2-fluoropyridin-4-yl)thiophene-2-carboxamide;
89. N-(1-(((R)-1-acryloylpyrrolidin-2-yl)methyl)-5-(1-hydroxy-3-methylbutyl)-1H-benzo[d]imidazol-2-yl)-5-(pyridazin-3-yl)thiophene-2-carboxamide;
90. (R)-N-(1-((1-acryloylpyrrolidin-2-yl)methyl)-5-(hydroxymethyl)-1H-benzo[d]imidazol-2-yl)-5-(oxazol-5-yl)thiophene-2-carboxamide;
91. (R)-N-(1-((1-acryloylpyrrolidin-2-yl)methyl)-5-(hydroxymethyl)-1H-benzo[d]imidazol-2-yl)-5-(1H-1,2,4-triazol-1-yl)thiophene-2-carboxamide;
92. (R)-N-(1-((1-acryloylpyrrolidin-2-yl)methyl)-5-(hydroxymethyl)-1H-benzo[d]imidazol-2-yl)-5-(2-methyloxazol-5-yl)thiophene-2-carboxamide;
93. (R)-N-(1-((1-acryloylpyrrolidin-2-yl)methyl)-5-(hydroxymethyl)-1H-benzo[d]imidazol-2-yl)-5-(1H-pyrazol-1-yl)thiophene-2-carboxamide;
94. (R)-N-(1-((1-acryloylpyrrolidin-2-yl)methyl)-5-(hydroxymethyl)-1H-benzo[d]imidazol-2-yl)-5-(2-fluoropyridin-4-yl)thiophene-2-carboxamide;
95. (R)-N-(1-((1-acryloylpyrrolidin-2-yl)methyl)-5-(2-hydroxypropan-2-yl)-1H-benzo[d]imidazol-2-yl)-5-(pyridazin-3-yl)thiophene-2-carboxamide;
96. (R)-N-(1-((1-acryloylpyrrolidin-2-yl)methyl)-5-(2-hydroxypropan-2-yl)-1H-benzo[d]imidazol-2-yl)-5-(oxazol-5-yl)thiophene-2-carboxamide;
97. (R)-N-(1-((1-acryloylpyrrolidin-2-yl)methyl)-5-(2-hydroxypropan-2-yl)-1H-benzo[d]imidazol-2-yl)-5-(1H-1,2,4-triazol-1-yl)thiophene-2-carboxamide;
98. (R)-N-(1-((1-acryloylpyrrolidin-2-yl)methyl)-5-(2-hydroxypropan-2-yl)-1H-benzo[d]imidazol-2-yl)-5-(2-methyloxazol-5-yl)thiophene-2-carboxamide;
99. (R)-N-(1-((1-acryloylpyrrolidin-2-yl)methyl)-5-(2-hydroxypropan-2-yl)-1H-benzo[d]imidazol-2-yl)-5-(1H-pyrazol-1-yl)thiophene-2-carboxamide;
100. (R)-N-(1-((1-acryloylpyrrolidin-2-yl)methyl)-5-(2-hydroxypropan-2-yl)-1H-benzo[d]imidazol-2-yl)-5-(2-fluoropyridin-4-yl)thiophene-2-carboxamide;
101. (R)-N-(1-((1-acryloylpyrrolidin-2-yl)methyl)-5-((isobutylamino)methyl)-1H-benzo[d]imidazol-2-yl)-5-(pyridazin-3-yl)thiophene-2-carboxamide;
102. (R)-N-(1-((1-acryloylpyrrolidin-2-yl)methyl)-5-((isobutylamino)methyl)-1H-benzo[d]imidazol-2-yl)-5-(oxazol-5-yl)thiophene-2-carboxamide;
103. (R)-N-(1-((1-acryloylpyrrolidin-2-yl)methyl)-5-((isobutylamino)methyl)-1H-benzo[d]imidazol-2-yl)-5-(1H-1,2,4-triazol-1-yl)thiophene-2-carboxamide;
104. (R)-N-(1-((1-acryloylpyrrolidin-2-yl)methyl)-5-((isobutylamino)methyl)-1H-benzo[d]imidazol-2-yl)-5-(2-methyloxazol-5-yl)thiophene-2-carboxamide;
105. (R)-N-(1-((1-acryloylpyrrolidin-2-yl)methyl)-5-((isobutylamino)methyl)-1H-benzo[d]imidazol-2-yl)-5-(1H-pyrazol-1-yl)thiophene-2-carboxamide;
106. (R)-N-(1-((1-acryloylpyrrolidin-2-yl)methyl)-5-((isobutylamino)methyl)-1H-benzo[d]imidazol-2-yl)-5-(2-fluoropyridin-4-yl)thiophene-2-carboxamide;
107. (R)-N-(1-((1-acryloylpyrrolidin-2-yl)methyl)-5-(((cyclopropylmethyl)amino)methyl)-1H-benzo[d]imidazol-2-yl)-5-(pyridazin-3-yl)thiophene-2-carboxamide;
108. (R)-N-(1-((1-acryloylpyrrolidin-2-yl)methyl)-5-((neopentylamino)methyl)-1H-benzo[d]imidazol-2-yl)-5-(oxazol-5-yl)thiophene-2-carboxamide;
109. (R)-N-(1-((1-acryloylpyrrolidin-2-yl)methyl)-5-((neopentylamino)methyl)-1H-benzo[d]imidazol-2-yl)-5-(1H-1,2,4-triazol-1-yl)thiophene-2-carboxamide;
110. (R)-N-(1-((1-acryloylpyrrolidin-2-yl)methyl)-5-((neopentylamino)methyl)-1H-benzo[d]imidazol-2-yl)-5-(2-methyloxazol-5-yl)thiophene-2-carboxamide;
111. (R)-N-(1-((1-acryloylpyrrolidin-2-yl)methyl)-5-((neopentylamino)methyl)-1H-benzo[d]imidazol-2-yl)-5-(1H-pyrazol-1-yl)thiophene-2-carboxamide;
112. (R)-N-(1-((1-acryloylpyrrolidin-2-yl)methyl)-5-((neopentylamino)methyl)-1H-benzo[d]imidazol-2-yl)-5-(2-fluoropyridin-4-yl)thiophene-2-carboxamide;
113. (R)-N-(1-((1-acryloylpyrrolidin-2-yl)methyl)-5-(((2,2-difluoroethyl)amino)methyl)-1H-benzo[d]imidazol-2-yl)-5-(pyridazin-3-yl)thiophene-2-carboxamide;
114. (R)-N-(1-((1-(2-cyano-4-methylpent-2-enoyl)pyrrolidin-2-yl)methyl)-5-(hydroxymethyl)-1H-benzo[d]imidazol-2-yl)-5-(2-fluoropyridin-4-yl)thiophene-2-carboxamide;
115. (R)-N-(1-((1-(2-cyano-4-methylpent-2-enoyl)pyrrolidin-2-yl)methyl)-5-(2-hydroxypropan-2-yl)-1H-benzo[d]imidazol-2-yl)-5-(1H-pyrazol-1-yl)thiophene-2-carboxamide;
116. (R)-N-(1-((1-(2-cyano-4-methylpent-2-enoyl)pyrrolidin-2-yl)methyl)-5-(2-hydroxypropan-2-yl)-1H-benzo[d]imidazol-2-yl)-5-(2-fluoropyridin-4-yl)thiophene-2-carboxamide;
117. (R)-N-(1-((1-(2-cyano-4-methylpent-2-enoyl)pyrrolidin-2-yl)methyl)-5-((isobutylamino)methyl)-1H-benzo[d]imidazol-2-yl)-5-(pyridazin-3-yl)thiophene-2-carboxamide;
118. (R)-N-(1-((1-(2-cyano-4-methylpent-2-enoyl)pyrrolidin-2-yl)methyl)-5-((neopentylamino)methyl)-1H-benzo[d]imidazol-2-yl)-5-(2-methyloxazol-5-yl)thiophene-2-carboxamide;
119. (R)-N-(1-((1-(2-cyano-4-methylpent-2-enoyl)pyrrolidin-2-yl)methyl)-5-((neopentylamino)methyl)-1H-benzo[d]imidazol-2-yl)-5-(1H-pyrazol-1-yl)thiophene-2-carboxamide;
120. (R)-N-(1-((1-(2-cyano-4-methylpent-2-enoyl)pyrrolidin-2-yl)methyl)-5-((neopentylamino)methyl)-1H-benzo[d]imidazol-2-yl)-5-(2-fluoropyridin-4-yl)thiophene-2-carboxamide;
121. (R)-N-(1-((1-(2-cyano-4-methylpent-2-enoyl)pyrrolidin-2-yl)methyl)-5-(((2,2-difluoroethyl)amino)methyl)-1H-benzo[d]imidazol-2-yl)-5-(pyridazin-3-yl)thiophene-2-carboxamide;
122. N-(1-(((R)-1-(2-cyano-3-cyclopropylacryloyl)pyrrolidin-2-yl)methyl)-5-(1-hydroxy-3-methylbutyl)-1H-benzo[d]imidazol-2-yl)-5-(1H-pyrazol-1-yl)thiophene-2-carboxamide;
123. (R)-N-(1-((1-(2-cyano-4,4-dimethylpent-2-enoyl)pyrrolidin-2-yl)methyl)-5-(((2-hydroxy-2-methylpropyl)amino)methyl)-1H-benzo[d]imidazol-2-yl)-5-(2-fluoropyridin-4-yl)thiophene-2-carboxamide;
124. N-(1-(((R)-1-(2-cyano-4,4-dimethylpent-2-enoyl)pyrrolidin-2-yl)methyl)-5-((((R)-1-hydroxypropan-2-yl)amino)methyl)-1H-benzo[d]imidazol-2-yl)-5-(1H-pyrazol-1-yl)thiophene-2-carboxamide;
125. N-(1-(((R)-1-(2-cyano-4,4-dimethylpent-2-enoyl)pyrrolidin-2-yl)methyl)-5-((((S)-1-hydroxypropan-2-yl)amino)methyl)-1H-benzo[d]imidazol-2-yl)-5-(2-fluoropyridin-4-yl)thiophene-2-carboxamide;
126. (R)-N-(1-((1-acryloylpyrrolidin-2-yl)methyl)-5-(((2-hydroxy-2-methylpropyl)amino)methyl)-1H-benzo[d]imidazol-2-yl)-5-(pyridazin-3-yl)thiophene-2-carboxamide;

127. (R)-N-(1-((1-acryloylpyrrolidin-2-yl)methyl)-5-(((2-hydroxy-2-methylpropyl)amino)methyl)-1H-benzo[d]imidazol-2-yl)-5-(1H-1,2,4-triazol-1-yl)thiophene-2-carboxamide;
128. (R)-N-(1-((1-acryloylpyrrolidin-2-yl)methyl)-5-(((2-hydroxy-2-methylpropyl)amino)methyl)-1H-benzo[d]imidazol-2-yl)-5-(2-methyloxazol-5-yl)thiophene-2-carboxamide;
129. (R)-N-(1-((1-acryloylpyrrolidin-2-yl)methyl)-5-(((2-hydroxy-2-methylpropyl)amino)methyl)-1H-benzo[d]imidazol-2-yl)-5-(1H-pyrazol-1-yl)thiophene-2-carboxamide;
130. (R)-N-(1-((1-acryloylpyrrolidin-2-yl)methyl)-5-(((2-hydroxy-2-methylpropyl)amino)methyl)-1H-benzo[d]imidazol-2-yl)-5-(2-fluoropyridin-4-yl)thiophene-2-carboxamide;
131. N-(1-(((R)-1-acryloylpyrrolidin-2-yl)methyl)-5-((((R)-1-hydroxypropan-2-yl)amino)methyl)-1H-benzo[d]imidazol-2-yl)-5-(pyridazin-3-yl)thiophene-2-carboxamide;
132. N-(1-(((R)-1-acryloylpyrrolidin-2-yl)methyl)-5-((((S)-1-hydroxypropan-2-yl)amino)methyl)-1H-benzo[d]imidazol-2-yl)-5-(pyridazin-3-yl)thiophene-2-carboxamide;
133. N-(1-(((R)-1-acryloylpyrrolidin-2-yl)methyl)-5-((((S)-1-hydroxypropan-2-yl)amino)methyl)-1H-benzo[d]imidazol-2-yl)-5-(1H-1,2,4-triazol-1-yl)thiophene-2-carboxamide;
134. N-(1-(((R)-1-acryloylpyrrolidin-2-yl)methyl)-5-((((S)-1-hydroxypropan-2-yl)amino)methyl)-1H-benzo[d]imidazol-2-yl)-5-(2-methyloxazol-5-yl)thiophene-2-carboxamide;
135. N-(1-(((R)-1-acryloylpyrrolidin-2-yl)methyl)-5-((((S)-1-hydroxypropan-2-yl)amino)methyl)-1H-benzo[d]imidazol-2-yl)-5-(1H-pyrazol-1-yl)thiophene-2-carboxamide;
136. N-(1-(((R)-1-acryloylpyrrolidin-2-yl)methyl)-5-((((S)-1-hydroxypropan-2-yl)amino)methyl)-1H-benzo[d]imidazol-2-yl)-5-(2-fluoropyridin-4-yl)thiophene-2-carboxamide;
137. (R)-N-(1-((1-(2-cyano-4-methylpent-2-enoyl)pyrrolidin-2-yl)methyl)-5-(((2-hydroxy-2-methylpropyl)amino)methyl)-1H-benzo[d]imidazol-2-yl)-5-(1H-pyrazol-1-yl)thiophene-2-carboxamide;
138. (R)-N-(1-((1-(2-cyano-4-methylpent-2-enoyl)pyrrolidin-2-yl)methyl)-5-(((2-hydroxy-2-methylpropyl)amino)methyl)-1H-benzo[d]imidazol-2-yl)-5-(2-fluoropyridin-4-yl)thiophene-2-carboxamide;
139. N-(1-(((R)-1-(2-cyano-4-methylpent-2-enoyl)pyrrolidin-2-yl)methyl)-5-((((R)-1-hydroxypropan-2-yl)amino)methyl)-1H-benzo[d]imidazol-2-yl)-5-(1H-pyrazol-1-yl)thiophene-2-carboxamide;
140. (R)-N-(1-((1-(2-cyano-3-(1-methylcyclopropyl)acryloyl)pyrrolidin-2-yl)methyl)-5-(((2-hydroxy-2-methylpropyl)amino)methyl)-1H-benzo[d]imidazol-2-yl)-5-(2-fluoropyridin-4-yl)thiophene-2-carboxamide;
141. N-(1-(((R)-1-(2-cyano-3-(1-methylcyclopropyl)acryloyl)pyrrolidin-2-yl)methyl)-5-((((R)-1-hydroxypropan-2-yl)amino)methyl)-1H-benzo[d]imidazol-2-yl)-5-(1H-pyrazol-1-yl)thiophene-2-carboxamide;
142. N-(1-(((R)-1-(2-cyano-3-(1-methylcyclopropyl)acryloyl)pyrrolidin-2-yl)methyl)-5-((((R)-1-hydroxypropan-2-yl)amino)methyl)-1H-benzo[d]imidazol-2-yl)-5-(2-fluoropyridin-4-yl)thiophene-2-carboxamide;
143. N-(1-(((R)-1-(2-cyano-3-(1-methylcyclopropyl)acryloyl)pyrrolidin-2-yl)methyl)-5-((((S)-1-hydroxypropan-2-yl)amino)methyl)-1H-benzo[d]imidazol-2-yl)-5-(1H-pyrazol-1-yl)thiophene-2-carboxamide;
144. N-(1-(((R)-1-(2-cyano-3-(1-methylcyclopropyl)acryloyl)pyrrolidin-2-yl)methyl)-5-((((S)-1-hydroxypropan-2-yl)amino)methyl)-1H-benzo[d]imidazol-2-yl)-5-(2-fluoropyridin-4-yl)thiophene-2-carboxamide;
145. (R)-N-(1-((1-(2-cyano-3-cyclopropylacryloyl)pyrrolidin-2-yl)methyl)-5-(((2-hydroxy-2-methylpropyl)amino)methyl)-1H-benzo[d]imidazol-2-yl)-5-(1H-pyrazol-1-yl)thiophene-2-carboxamide;
146. (R)-N-(1-((1-(2-cyano-3-cyclopropylacryloyl)pyrrolidin-2-yl)methyl)-5-(((2-hydroxy-2-methylpropyl)amino)methyl)-1H-benzo[d]imidazol-2-yl)-5-(2-fluoropyridin-4-yl)thiophene-2-carboxamide;
147. N-(1-(((R)-1-(2-cyano-3-cyclopropylacryloyl)pyrrolidin-2-yl)methyl)-5-((((R)-1-hydroxypropan-2-yl)amino)methyl)-1H-benzo[d]imidazol-2-yl)-5-(1H-pyrazol-1-yl)thiophene-2-carboxamide
148. N-(1-(((R)-1-(2-cyano-3-cyclopropylacryloyl)pyrrolidin-2-yl)methyl)-5-((((R)-1-hydroxypropan-2-yl)amino)methyl)-1H-benzo[d]imidazol-2-yl)-5-(2-fluoropyridin-4-yl)thiophene-2-carboxamide;
149. N-(1-(((R)-1-(2-cyano-3-cyclopropylacryloyl)pyrrolidin-2-yl)methyl)-5-((((S)-1-hydroxypropan-2-yl)amino)methyl)-1H-benzo[d]imidazol-2-yl)-5-(1H-pyrazol-1-yl)thiophene-2-carboxamide;
150. N-(1-(((R)-1-(2-cyano-3-cyclopropylacryloyl)pyrrolidin-2-yl)methyl)-5-((((S)-1-hydroxypropan-2-yl)amino)methyl)-1H-benzo[d]imidazol-2-yl)-5-(2-fluoropyridin-4-yl)thiophene-2-carboxamide;

or, an E or Z isomer thereof; or a pharmaceutically acceptable salt of any of the foregoing compounds.

Embodiments:

Embodiment 1

In embodiment 1, the compound of Formula (I), or first and second subembodiments wherein Ar is thiophenylene or 2,5-thiophenylene respectively, or a salt thereof has the structure (Ia):

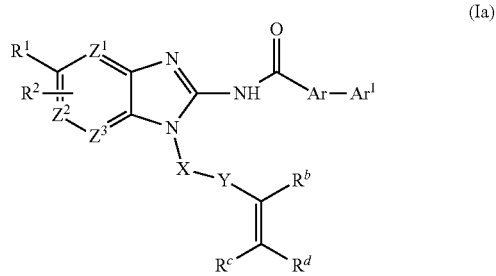

(Ia)

and wherein the groups are as defined for Formula (I) in the Summary. Within embodiment 1, in one group of compounds $Z^1$, $Z^2$, and $Z^3$ are CH (or C if substituted with $R^2$).

Within embodiment 1 there is a group wherein Ar is thiophenylene or 2,5-thiophenylene and in each case;

$Ar^1$ is 5- or 6-membered heteroaryl optionally substituted with one or two substituents independently selected from alkyl, alkoxy, hydroxy, cyano, alkylthio, halo, haloalkyl, haloalkoxy, or cycloalkyl;

X is moiety of formula II (where Z is bond or alkylene, and ring A is heterocycloamino), -cycloalkylene-NR$^a$-, or -(alkylene)-NR$^a$— (where each R$^a$ is hydrogen, alkyl or cycloalkyl and alkylene in -(alkylene)-NR$^a$— is optionally substituted with hydroxy or alkoxy);

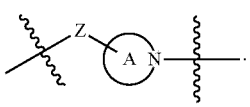
(II)

Embodiment 2

In embodiment 2, the compound of Formula (I) or first and second subembodiments wherein Ar is thiophenylene or 2,5-thiophenylene respectively, or a salt thereof has the structure (Ib):

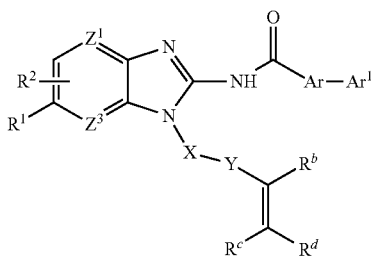

wherein the groups are as defined for Formula (I) in the Summary. Within embodiment 2, in one group of compounds $Z^2$ and $Z^3$ are CH (or C if substituted with $R^2$).

Within embodiment 2 there is a group wherein Ar is thiophenylene or 2,5-thiophenylene and in each case;

$Ar^1$ is 5- or 6-membered heteroaryl optionally substituted with one or two substituents independently selected from alkyl, alkoxy, hydroxy, cyano, alkylthio, halo, haloalkyl, haloalkoxy, or cycloalkyl;

X is moiety of formula II (where Z is bond or alkylene, and ring A is heterocycloamino), -cycloalkylene-$NR^a$—, or -(alkylene)-$NR^a$— (where each $R^a$ is hydrogen, alkyl or cycloalkyl and alkylene in -(alkylene)-$NR^a$— is optionally substituted with hydroxy or alkoxy);

Embodiment 3

In embodiment 3, the compounds or salt thereof as defined in Formula (I) in the Summary and embodiments 1 and 2 and groups contained therein, are those wherein $R^b$ and $R^c$ are hydrogen or $R^b$ and $R^d$ together form a bond. Within this embodiment, in one group of compounds or a salt thereof $R^d$ is hydrogen. Within this embodiment, in another group of compounds or a salt thereof $R^b$ and $R^d$ together form a bond (i.e., —YC≡$CR^c$).

Embodiment 4

In embodiment 4, the compounds or a salt thereof as defined in Formula (I) in the Summary and embodiments 1 and 2, and groups contained therein, are those wherein $R^b$ is cyano and $R^c$ is alkyl, alkyl substituted with alkoxy or hydroxy, cyclolalkyl substituted with alkyl, or 3 to 6 membered saturated monocyclic heterocyclyl containing one or two heteroatoms selected from N, O, or S and optionally substituted with one, two, or three substituents independently selected from hydroxy, alkyl, alkoxy, oxetan-3-yl, or fluoro.

(4a) Within embodiment 4, in one group of compounds or a salt thereof $R^c$ is alkyl. Within this group (4a), in one group of compounds $R^c$ is isopropyl or tert-butyl.

(4b) Within embodiment 4, in another group of compounds or a salt thereof $R^c$ is cycloalkyl. Within group (4b), in one group of compounds $R^c$ is cyclopropyl, cyclobutyl, cyclopentyl, or cyclohexyl. Within s group (4b), in another group of compounds $R^c$ is cyclopropyl.

(4c) Within embodiment 4, in another group of compounds or a salt thereof $R^c$ is cycloalkyl substituted with alkyl. Within group (4c), in one group of compounds or a salt thereof $R^c$ is 1-methyl-cyclopropanyl.

(4d) Within embodiment 4, in yet another group of compounds or a salt thereof $R^c$ is alkyl substituted with alkoxy or hydroxy. Within group (4d), in one group of compounds or a salt thereof $R^c$ is —$C(CH_3)_2NH(CH_2)_2OCH_3$, —$C(CH_3)_2OCH_2CH_3$, or —$C(CH_3)_2OH$.

(4e) Within embodiment 4, in yet another group of compounds or a salt thereof $R^c$ is 3 to 6 membered saturated monocyclic heterocyclyl containing one or two heteroatoms selected from N, O, or S and optionally substituted with one, two, or three substituents independently selected from hydroxy, alkyl, alkoxy, oxetan-3-yl, or fluoro. Within group (4e), in one group of compounds or a salt thereof $R^c$ is 2-pyrrolidinyl, 3- or 4-piperidinyl, 1-methylpiperidin-4-yl, 1-methylpiperidin-3-yl, azetidin-3-yl, oxetan-3-yl, 3-methyloxetan-3-yl, piperazin-1-yl, 4-methylpiperazin-1-yl, or 4-oxetan-3-ylpiperazin-1-yl.

Embodiment 5

In embodiment 5, the compounds or a salt thereof as defined in Formula (I) or a salt thereof as defined in the Summary and embodiments 1 and 2 and groups contained therein, are those wherein $R^b$ is fluoro and $R^c$ is hydrogen; and $R^d$ is hydrogen, alkyl or alkyl substituted with amino, alkylamino, or dialkylamino, or $R^b$ and $R^d$ together form a bond.

(5a) Within embodiment 5, in one group of compounds or a salt thereof $R^d$ is hydrogen.

(5b) Within embodiment 5, in another group of compounds or a salt thereof $R^b$ and $R^d$ together form a bond.

Embodiment 6

In embodiment 6, the compounds or a salt thereof as defined in Formula (I) in the Summary and embodiments 1 through 6 and groups contained therein, the compounds or a salt thereof, are those wherein X is a moiety of formula II (where Z is bond or alkylene, and ring A is heterocycloamino optionally substituted with one or two substituents independently selected from alkyl, hydroxy, or fluoro).

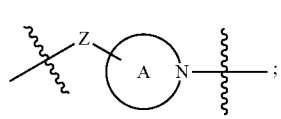
(II)

(6a) Within embodiment 6, in one group of compounds or a salt thereof, X is IIIa or IIIb. In one group, X is IIIa. In another group X is IIIc.

(6b) Within embodiment 6, in another group of compounds or a salt thereof, X is: IIId or IIIf. Within group (6b), in one group of compounds or a salt thereof —X— is IIIe. Within group (6b), in another group of compounds or a salt thereof —X— is IIIg.

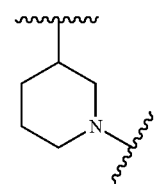
IIIa

-continued

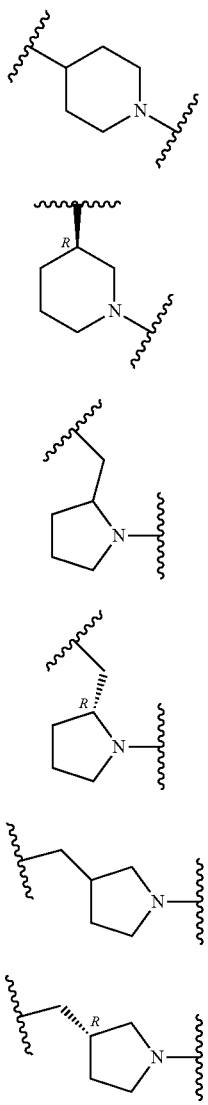

IIIb

IIIc

IIId

IIIe

IIIf

IIIg (6c) Within embodiment 6, in another group of compounds or a salt thereof, X is: -alkylene-NR$^a$—. Within group (6c), in one group of compounds or a salt thereof —X— is —(CH$_2$)$_2$NH— or —(CH$_2$)$_2$N(CH$_3$)—.

Embodiment 7

In embodiment 7, the compounds or a salt thereof as defined in Formula (I) in the Summary and embodiments 1, 2, 3, 4, 5, and 6 and groups contained therein, are those wherein R$^1$ is hydroxyalkyl, alkoxyalkyl, heterocyclyl, heterocyclylalkyl (wherein the heterocyclyl ring in heterocyclyl and heterocyclylalkyl is optionally substituted with one, two, or three substituents independently selected from alkyl, halo, hydroxy, alkoxy, hydroxyalkyl, or alkoxyalkyl), or -(alkylene)-NR$^3$R$^5$ (where R$^3$ is hydrogen or alkyl and R$^5$ is alkyl, haloalkyl, hydroxyalkyl, alkoxyalkyl, cycloalkyl, cycloalkylalkyl, heterocyclyl, or heterocyclylalkyl wherein the heterocyclyl ring in heterocyclyl and heterocyclylalkyl is optionally substituted with one, two, or three substituents independently selected from alkyl, halo, hydroxy, alkoxy, hydroxyalkyl, or alkoxyalkyl; or R$^3$ and R$^5$ together with the nitrogen atom to which they are attached form heterocycloamino or spiroheterocycloamino wherein the heterocycloamino ring is optionally substituted with one, two, or three substituents independently selected from alkyl, halo, hydroxyl, alkoxy, hydroxyalkyl, or alkoxyalkyl).

(7a) Within embodiment 7, in one group of compounds or a salt thereof R$^1$ is hydroxyalkyl. Within group (7a), in one group of compounds or a salt thereof, R$^1$ is hydroxymethyl, 2-hydroxyethyl, 2-hydroxy-2-propyl, or —CH(OH)CH$_2$CH(CH$_3$)$_2$.

(7b) Within embodiment 7, in another group of compounds or a salt thereof R$^1$ is heterocyclyl wherein the heterocyclyl ring is optionally substituted with one, two, or three substituents independently selected from alkyl, halo, hydroxy, alkoxy, hydroxyalkyl, or alkoxyalkyl). Within group (7b), in one group of compounds or a salt thereof, R$^1$ is tetrahydropyran-2-yl or 2-tetrahydrofuran-4-yl.

(7c) Within embodiment 7, in another group of compounds or a salt thereof R$^1$ is heterocyclylalkyl wherein the heterocyclyl ring in heterocyclylalkyl is optionally substituted with one, two, or three substituents independently selected from alkyl, halo, hydroxy, alkoxy, hydroxyalkyl, or alkoxyalkyl. Within group (7c), in one group of compounds or a salt thereof, R$^1$ is 2R- or 2S-(methoxymethylpyrrolidin-1-yl)methyl, morpholin-4-ylmethyl, 2,6-dimethylmorpholin-4-yl., pyrrolidin-1-yl, piperazin-1-ylmethyl, or piperidin-1-ylmethyl.

(7d) Within embodiment 7, in one group of compounds or a salt thereof R$^1$ is -(alkylene)-NR$^3$R$^5$ where R$^3$ is hydrogen or alkyl and R$^5$ is alkyl, haloalkyl, hydroxyalkyl, alkoxyalkyl, cycloalkyl, cycloalkylalkyl, optionally substituted heteroaryl, optionally substituted heteroarylalkyl, heterocyclyl, or heterocyclylalkyl (wherein the heterocyclic ring in heterocyclyl and heterocyclylalkyl is optionally substituted with one, two, or three substituents independently selected from alkyl, halo, hydroxy, alkoxy, hydroxyalkyl, or alkoxyalkyl). Within group (7c), in one group of compounds or a salt thereof, R$^1$ is —(CH$_2$)—NHR$^5$ where R$^5$ is 2,2-dimethylpropyl, 2-methylpropyl, cyclopropylmethyl, —CH$_2$C(CH$_3$)$_2$OH, (R)-CH(CH$_2$OH)C(CH$_3$)$_3$, (S)-CH(CH$_2$OH)C(CH$_3$)$_3$, (R)-CH(CH$_2$OH)CH$_3$, (S)-CH(CH$_2$OH)CH$_3$, (R)-CH(CH$_2$OCH$_3$)CH$_3$, (S)-CH(CH$_2$OCH$_3$)CH$_3$, (S)-CH(CH$_3$)C(CH$_3$)$_3$, (R)-CH(CH$_3$)C(CH$_3$)$_3$, tetrahydrofuran-4-yl, 2,2-difluoroethyl, tetrahydropyran-3-yl, oxazol-2-ylmethyl, thiazol-2-ylmethyl, tetrahydrofuran-2-ylmethyl, morpholin-4-ylmethyl, (R)-CH(CH$_3$)C(CH$_3$)$_3$, or (S)-CH(CH$_3$)C(CH$_3$)$_3$. Within group (7c), in another group of compounds or a salt thereof R$^1$ is —(CH$_2$)—NHR$^5$ where is 2-methylpropyl, cyclopropylmethyl, 2,2-dimethylpropyl, 2,2-difluoroethyl, (R)-CH(CH$_3$)C(CH$_3$)$_3$, (R)-CH(CH$_2$OH)CH$_3$, (S)-CH(CH$_2$OH)CH$_3$, or —CH$_2$C(CH$_3$)$_2$OH (7e) Within embodiment 7, in another one group of compounds R$^1$ is -(alkylene)-NR$^3$R$^5$ where R$^3$ and R$^5$ together with the nitrogen atom to which they are attached from heterocycloamino optionally substituted with one or two substituents independently selected from alkyl, halo, hydroxyalkyl, or alkoxyalkyl. Within this group (7e) in one group of compounds or a salt thereof R$^1$ is —CH$_2$-2,6-dimethylmorpholin-4-yl, —CH$_2$-morpholin-4-yl, or —CH$_2$-4-methylpiperazin-yl.

(7f) Within embodiment 7, in another one group of compounds or a salt thereof R$^1$ is:

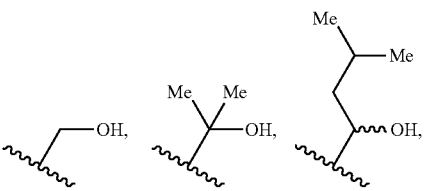

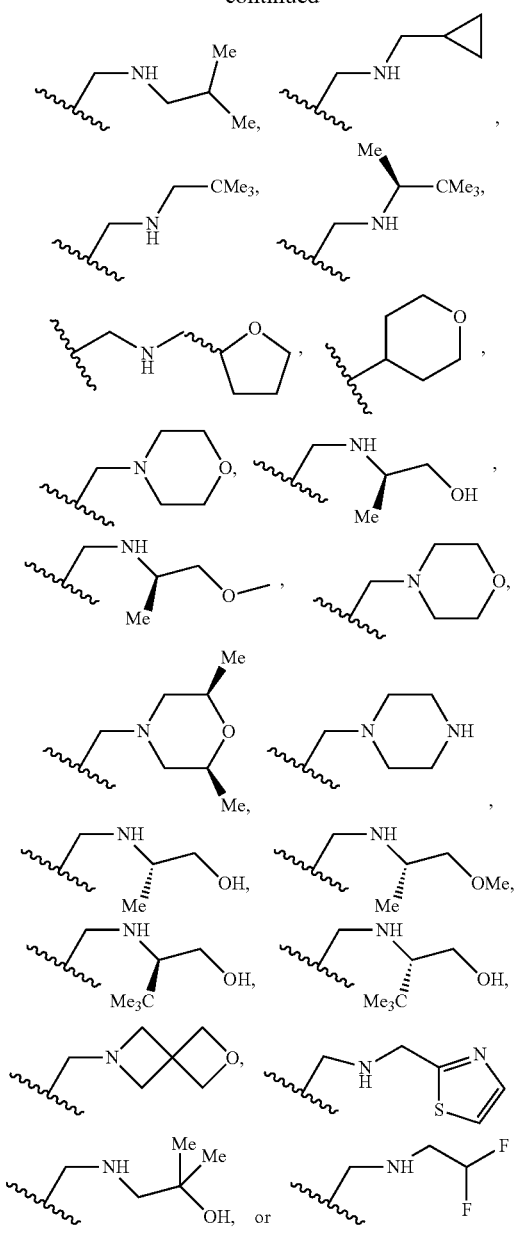
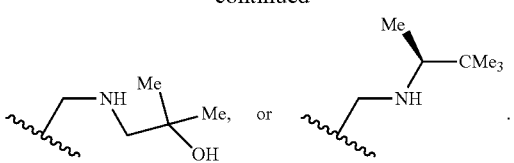
Embodiment 8
In embodiment 8, the compounds or a salt thereof as defined in Formula (I) in the Summary and embodiments 1, 2, 3, 4, 5, 6, and 7 and groups contained therein, are those wherein
—Ar$^1$—Ar$^2$ is:
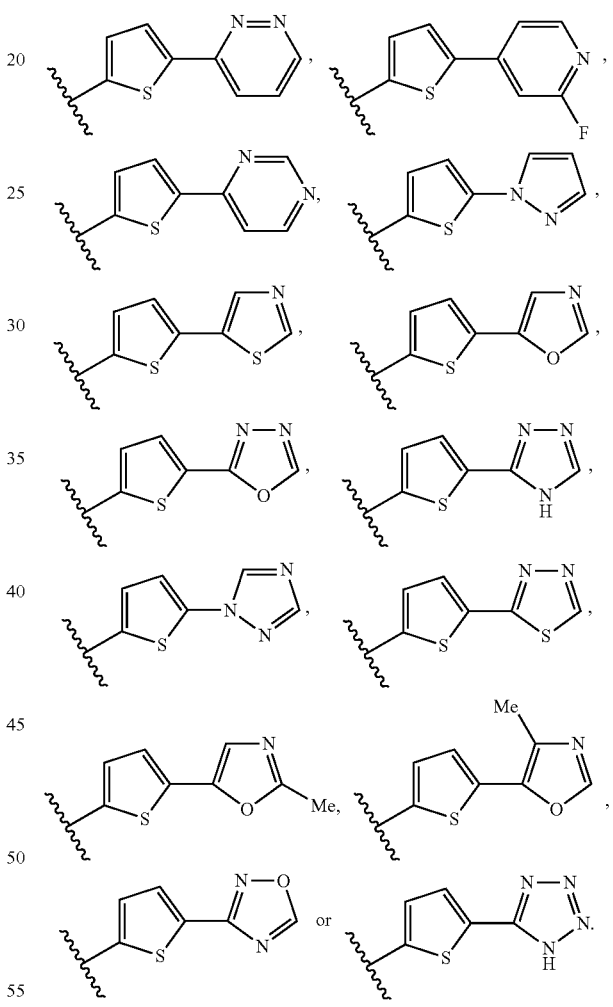
Within group (7f), in one group of compounds or a salt thereof, R$^1$ is:
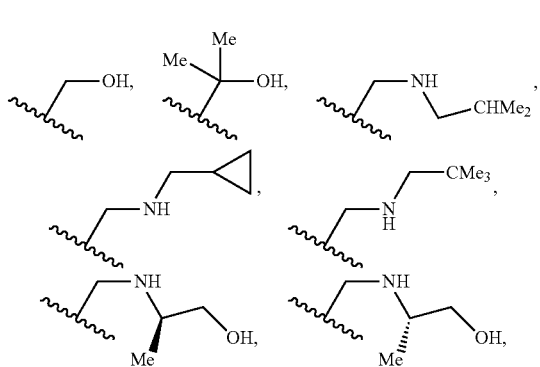
Within embodiment 8, in one group of compounds or a salt thereof —Ar$^1$—Ar$^2$ is:
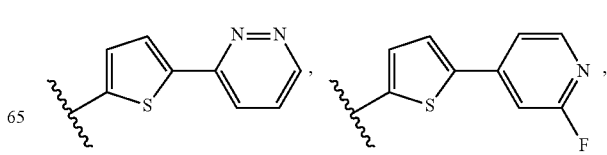

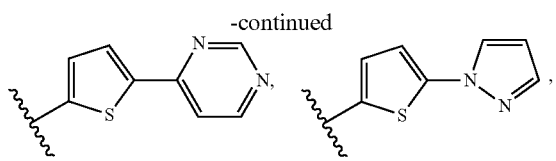
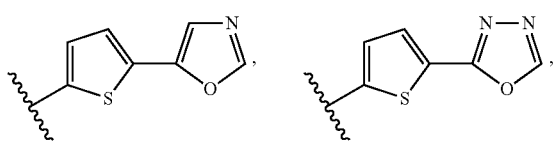
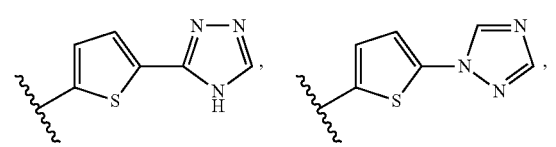
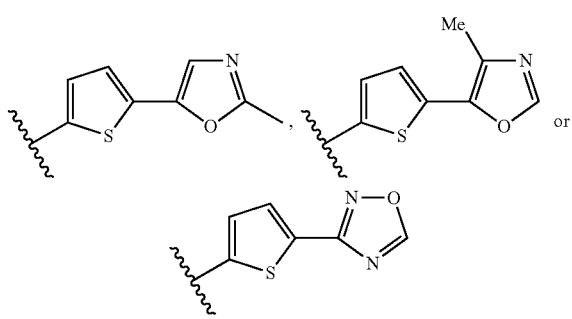

Within embodiment 8, in another group of compounds or a salt thereof —Ar¹—Ar² is:

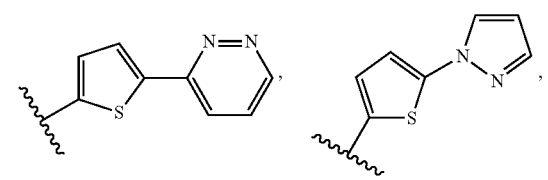
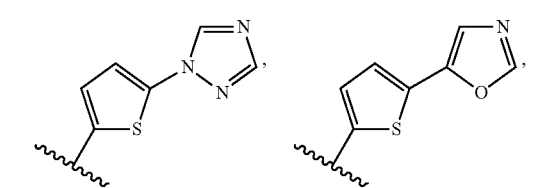
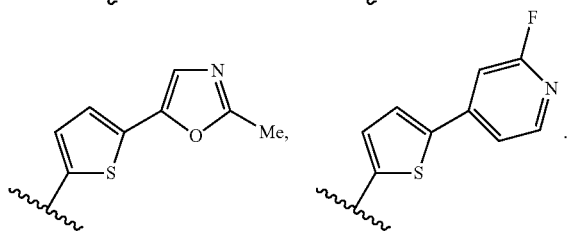

Embodiment 9

In embodiment 9, the compounds or a salt thereof as defined in Formula (I) in the Summary and embodiments 1, 2, 3, 4, 5, 6, 7, and 8 and groups contained therein, are those wherein Y is —CO— and $R^2$ is hydrogen.

Embodiment 10

In embodiment 10, the compounds or a salt thereof as defined in Formula (I) in the Summary and embodiments 1, 2, 3, 4, 5, 6, 7, and Band groups contained therein, are those wherein Y is —SO$_2$— and $R^2$ is hydrogen.

General Synthetic Schemes

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C. Compounds of Formula (I) can be prepared as illustrated and described in Schemes 1 through 5 below.

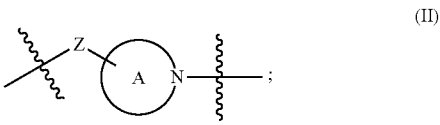

(II)

Compounds of Formula (I) where $Z^1$ is CH, X is moiety of formula Ha, $R^b$ is cyano, and other groups are as defined in the Summary can be prepared as illustrated and described in Scheme 1 below.

Scheme 1

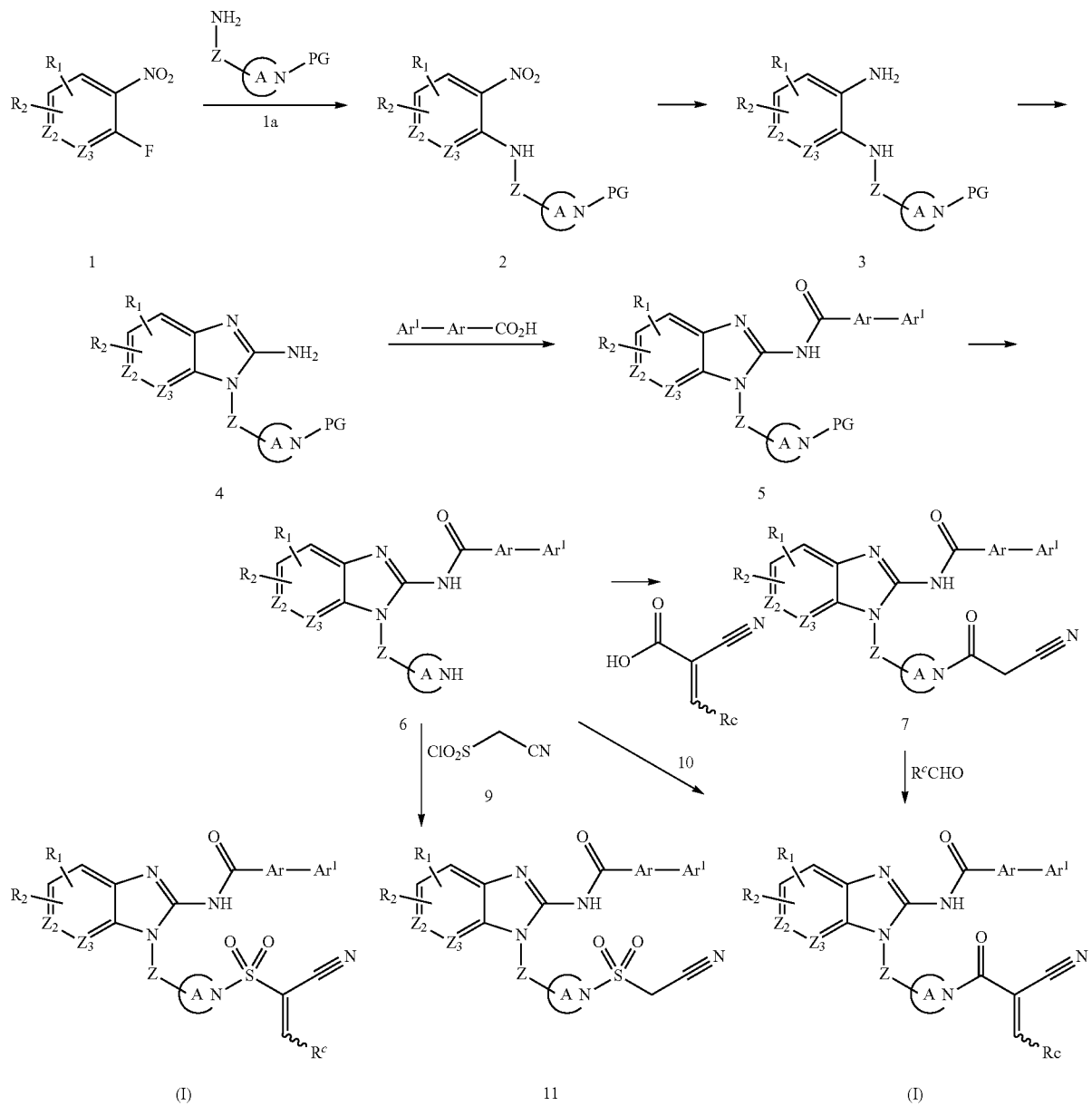

Displacement of the fluorine or other halogen group in a compound of formula 1 where $Z^2$, $Z^3$, $R^1$, and $R^2$ are as defined in the Summary, by a monoprotected diamine of formula 1a where ring A and Z are as defined in the Summary and PG is a suitable nitrogen protecting group, in a solvent such as acetonitrile provides a compound of formula 2. Compounds of formula 1 and 1a, e.g., 1-fluoro-2-nitrobenzene, (R)-tert-butyl 2-(aminomethyl)pyrrolidine-1-carboxylate, (S)-tert-butyl 2-(aminomethyl)pyrrolidine-1-carboxylate, tert-butyl 3-aminopiperidine-1-carboxylate, tert-butyl 4-aminopiperidine-1-carboxylate, tert-butyl 3-(aminomethyl)azetidine-1-carboxylate, are commercially available or they can be prepared by methods well known in the art. Reduction of the nitro group in 2 can be accomplished by various reduction methods such as hydrogenation with Pd catalysis or by reduction with elemental Zn. The resulting diamino compound 3 can be cyclized to the aminobenzimidazole compound of formula 4 by treatment with cyanogen bromide in a solvent such as ethanol. Coupling of 4 with a carboxylic acid of formula $Ar^1$—Ar—COOH where Ar and $Ar^1$ are as defined in the Summary occurs under standard amide coupling conditions or with an acid derivative such as a carboxylic acid chloride to provide compound of formula 5. Removal of the amino protecting group PG, followed by coupling of the resulting compound 6 with cyanoacetic acid provides a compound of formula 7. Compound 7 can be then converted to a compound of Formula (I) by methods well known in the art. For example, compounds of Formula (I) where X is —CO— can be prepared by condensing compound 7 with an aldehyde of formula $R^cCHO$, where $R^c$ is as defined in the Summary, under standard condensation conditions such as using a base such as piperidine and the like, in the presence or absence of acetic acid and the like in solvents such as ethanol at temperatures ranging from room temperature (RT) to reflux to afford compounds of Formula (I). Compounds of formula R$^c$CHO are commercially available or they can be prepared by methods well known in the art such as, e.g., acetaldehyde, cyclopropylcarbaldehyde, isobutyraldehyde, 2-(dimethyl amino)-2-methylpropanal, and 2-methyl-2-(morpholin-4-yl) propanal are commercially available. Ethoxy-2-methylpropanal was prepared from isobutyraldehyde as described in PCT Int. Appl., 2007142576. Likewise the condensation can be performed by adding the desired aldehyde, base such as pyrrolidine or piperidine with or without chlorotrimethylsilane in dichloromethane or other suitable solvent (e.g. dioxane or ethanol).

Alternatively, compounds of Formula (I) where X is —CO— can be prepared by reacting compound 6 with an acid of formula 10 where R$^c$ is as defined in the Summary under amide coupling conditions. Compounds of Formula (I) where X is —SO$_2$— can be prepared by reacting amine 6 with a sulfonyl chloride of formula 9, followed by condensation of resulting compound 11 with an aldehyde of formula R$^c$CHO as described.

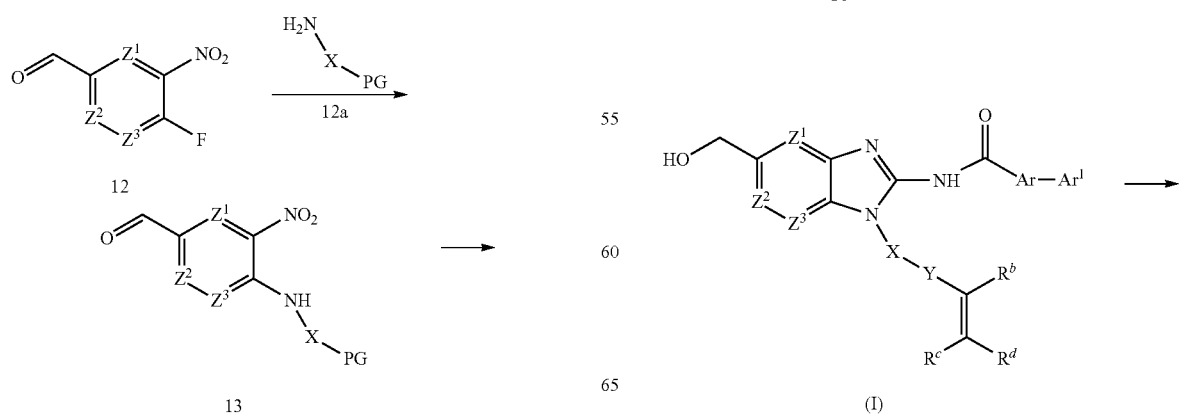

(II)

It will be apparent to a person of ordinary skilled in the art, that replacing the formula II fragment with amines of formula NH$_2$-alkylene —NHPG where PG is a suitable amino protecting group e.g., tert-butyl N-(2-aminoethyl) carbamate, followed by steps described above would give compounds of Formula (I) where X is -alkyleneNH, and Y is CO or SO$_2$. Compounds of Formula (I) where R$^b$ and R$^c$ are hydrogen, can be prepared by the addition of acryloyl chloride to amines such as 6 in a solvent such as toluene or THF.

Alternatively compounds of Formula (I) where R$^1$ is hydroxymethyl, or —(CH$_2$)—NR$^3$R$^5$ where R$^3$ and R$^5$ and Z$^1$, Z$^2$, Z$^3$, X, Y, Ar, Ar$^1$, R$^b$, R$^c$ and R$^d$ are as defined in the Summary can also be prepared as illustrated and described in Scheme 2 below.

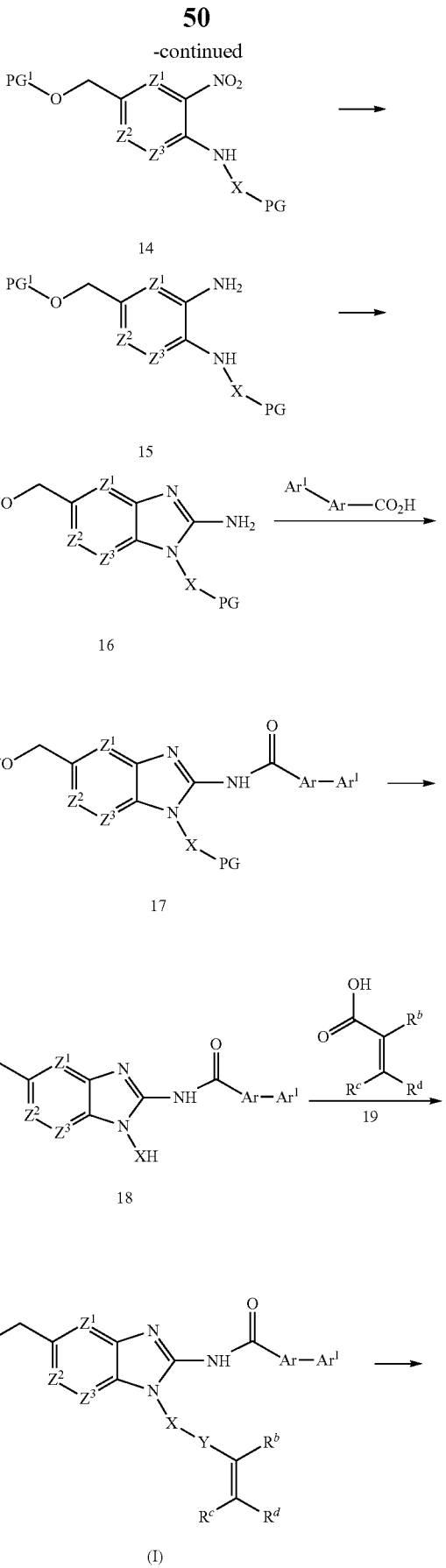

-continued

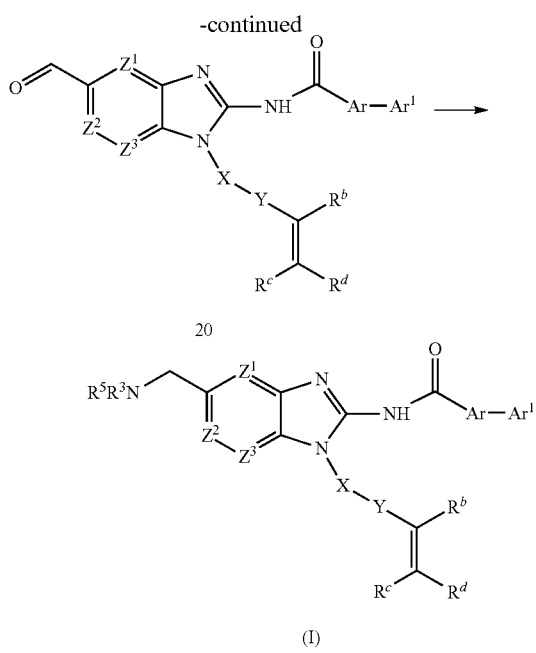

Displacement of the fluorine or other halogen group in a compound of formula 12 by a monoprotected diamine 12a where X is as defined in the Summary and PG is a suitable nitrogen protecting group such as tert-butoxycarbonyl, in a solvent such as acetonitrile provides a compound of formula 13. Compounds of formula 12 and 12a, e.g., 4-fluoro-3-nitrobenzaldehyde, tert-butyl (2-aminoethyl)carbamate, tert-butyl (2-aminoethyl)(methyl)carbamate, (R)-tert-butyl 2-(aminomethyl)pyrrolidine-1-carboxylate, (S)-tert-butyl 2-(aminomethyl)pyrrolidine-1-carboxylate, are commercially available or they can be prepared by methods well known in the art. Reduction of the aldehyde group with a suitable reducing reagent such as lithium borohydride and subsequently protected with a suitable hydroxy protecting group such as TBS by reaction with TBSCl and a base such as imidazole in DMF to afford compounds of formula 14.

Reduction of the nitro group in 14 can be accomplished by various reduction methods such as hydrogenation with Pd catalysis or by the action of elemental Zn. The resulting diamino compound 15 can be cyclized to the aminobenzimidazole compound of formula 16 by treatment with cyanogen bromide in a solvent such as ethanol. Coupling of 16 with a carboxylic acid of formula Ar¹—Ar—COOH where Ar and Ar' as defined in the Summary occurs under standard amide coupling conditions or with an acid derivative such as a carboxylic acid chloride to provide compound of formula 17. Simultaneous or sequential removal of the amino and hydroxy protecting groups affords compounds of formula 18. For example, when PG and PG¹ are Boc and TBS groups they can be removed simultaneously with an acid such as HCl or TFA.

Coupling of the resulting compound 18 with acid derivative 19 provides a compound of formula (I) where R¹ is hydroxymethyl. Compound (I) can be then oxidized to the corresponding aldehyde 20 with an agent such as the Dess-Martin Periodinane and then converted to a compound of Formula (I) where R¹ is —(CH₂)—NR³R⁵ by reacting compound 20 with an amine of formula NR³R⁵ where R³ and R⁵ are as defined in the Summary reductive amination reaction conditions such as in the presence of sodium triacetoxyborohydride in dichloroethane as a solvent.

Alternatively, compounds of Formula (I) where Z¹ is CH (or C if substituted with R¹ or R²), R¹ is —(CH₂)—NR³R⁵ where R³ and R⁵ are as defined in the Summary, X is a ring of formula II, R^b is cyano, and other groups are as defined in the Summary can also be prepared as illustrated and described in Scheme 3 below.

Scheme 3

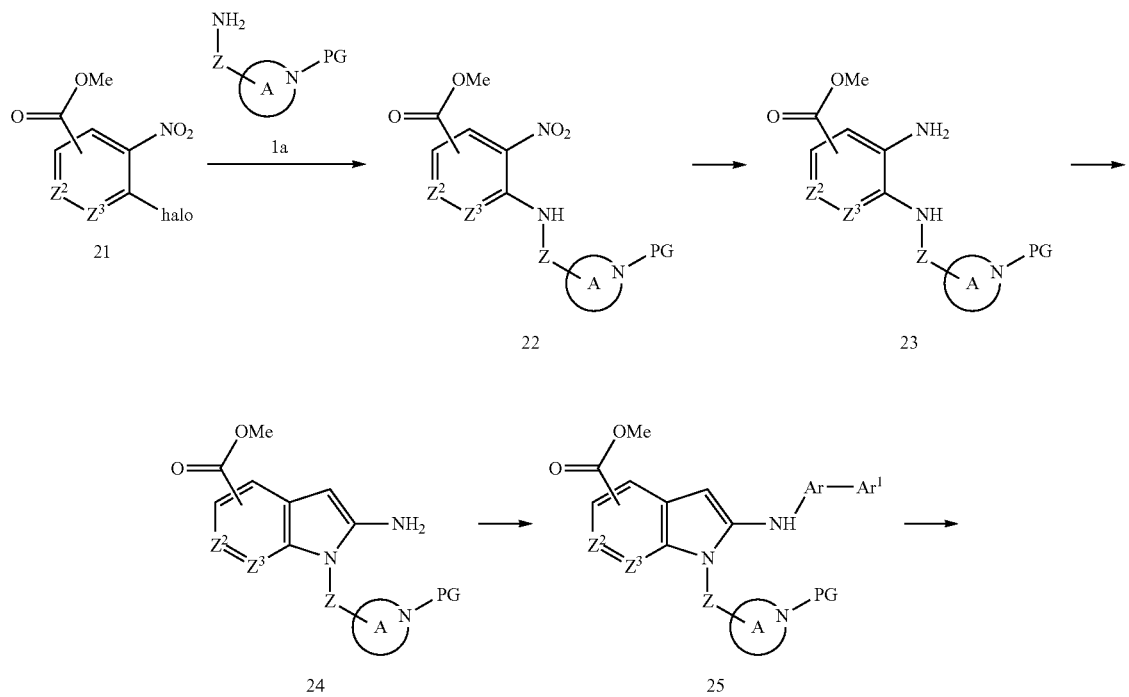

-continued
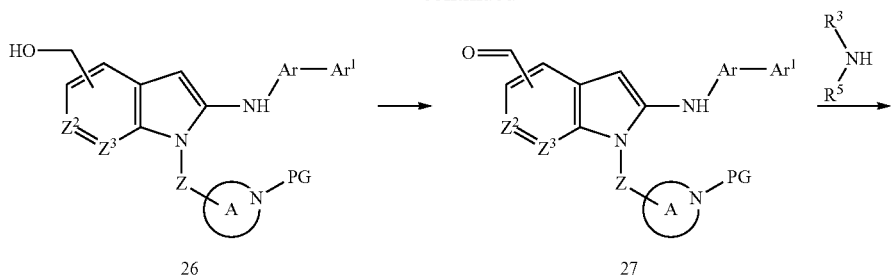
26 → 27
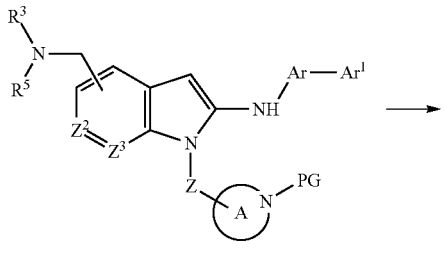
28
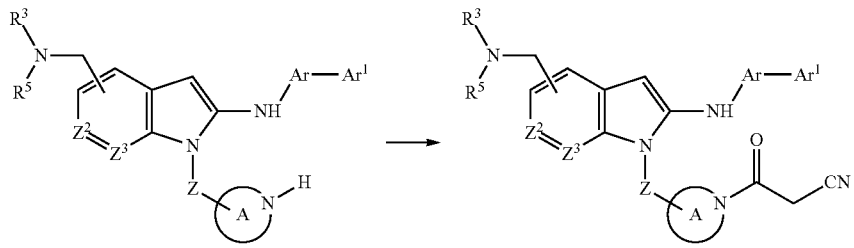
29 → 30
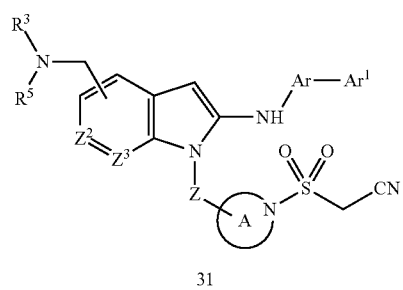
31
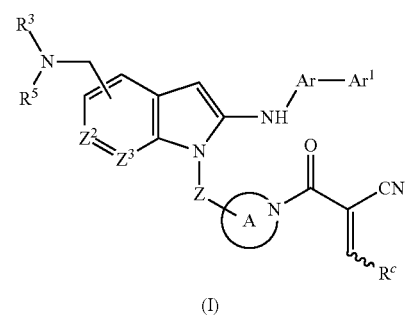
(I)
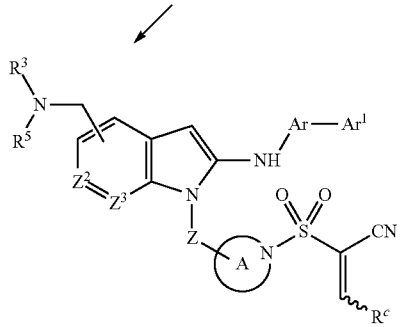
(I)

Displacement of a halogen atom in a compound of formula 21 where $Z^2$ and $Z^3$ are as defined in the Summary by a monoprotected diamine 1a where Ring A and Z are as defined in the Summary, and PG is a suitable nitrogen protecting group, in a solvent such as acetonitrile provides a compound of formula 22. Compounds of formula 21 and 1a, e.g., methyl 4-fluoro-3-nitrobenzoate, methyl 3-fluoro-4-nitrobenzenecarboxylate, tert-butyl (2-aminoethyl)carbamate, tert-butyl (2-aminoethyl)(methyl)-carbamate, (R)-tert-butyl 2-(aminomethyl)pyrrolidine-1-carboxylate, (S)-tert-butyl 2-(aminomethyl)pyrrolidine-1-carboxylate, tert-butyl 3-amino-piperidine-1-carboxylate, tert-butyl 4-aminopiperidine-1-carboxylate, tert-butyl 3-(aminomethyl)azetidine-1-carboxylate, are commercially available or they can be prepared by methods well known in the art.

Reduction of the nitro group in 22 can be accomplished by various reduction methods such as hydrogenation with Pd catalysis or by the action of elemental Zn. The resulting diamino compound 23 can be cyclized to the aminobenzimidazole compound of formula 24 by treatment with cyanogen bromide in a solvent such as ethanol. Coupling of 24 with a carboxylic acid of formula $Ar^1Ar$—COOH where $Ar^1$—Ar is as defined in the Summary under standard amide coupling conditions or with an acid derivative such as a carboxylic acid chloride provides a compound of formula 25.

Reduction of the ester group in compound 25 with a suitable reducing agent such as lithium aluminum hydride affords alcohol 26 which can be oxidized with an oxidizing agent such as Dess-Martin Periodinane or PCC other standard oxidizing protocols such as the Swern oxidation and the like to afford aldehyde 27. Compound 27 can undergo reductive amination with amines of formula 31 where $R^3$ and $R^5$ are as described in the Summary to afford compound 28. Removal of the amino protecting group PG provides compound 29 which can be converted to a compound of Formula (I) as described in Scheme I above.

Compounds of Formula (I) where $R^1$ is —CH(OH)alkyl, —C(OH)(alkyl)$_2$ can be prepared by addition of an alkylmagnesium halide (RMgX, Grignard reagent) to compound 25 to give a tertiary alcohol [$R^1$=—C(OH)(alkyl)$_2$]. Addition of an alkylmagnesium halide (RMgX, Grignard reagent) to compound 27 affords a secondary alcohol [$R^1$=—CH(OH)alkyl]. Deprotection of the protecting group affords a compound which can be converted to a compound of Formula (I) as described in Scheme I above.

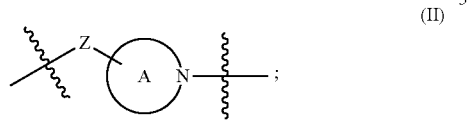

(II)

Alternatively, compounds of Formula (I) where $Z^1$ is CH (or C if substituted with $R^1$ or $R^2$), $R^1$ is —(CH$_2$)—NR$^3$R$^5$ where $R^3$ and $R^5$ are as defined in the Summary, X is a ring of formula (II), $R^b$ is cyano, and other groups are as defined in the Summary can also be prepared as illustrated and described in Scheme 4 below.

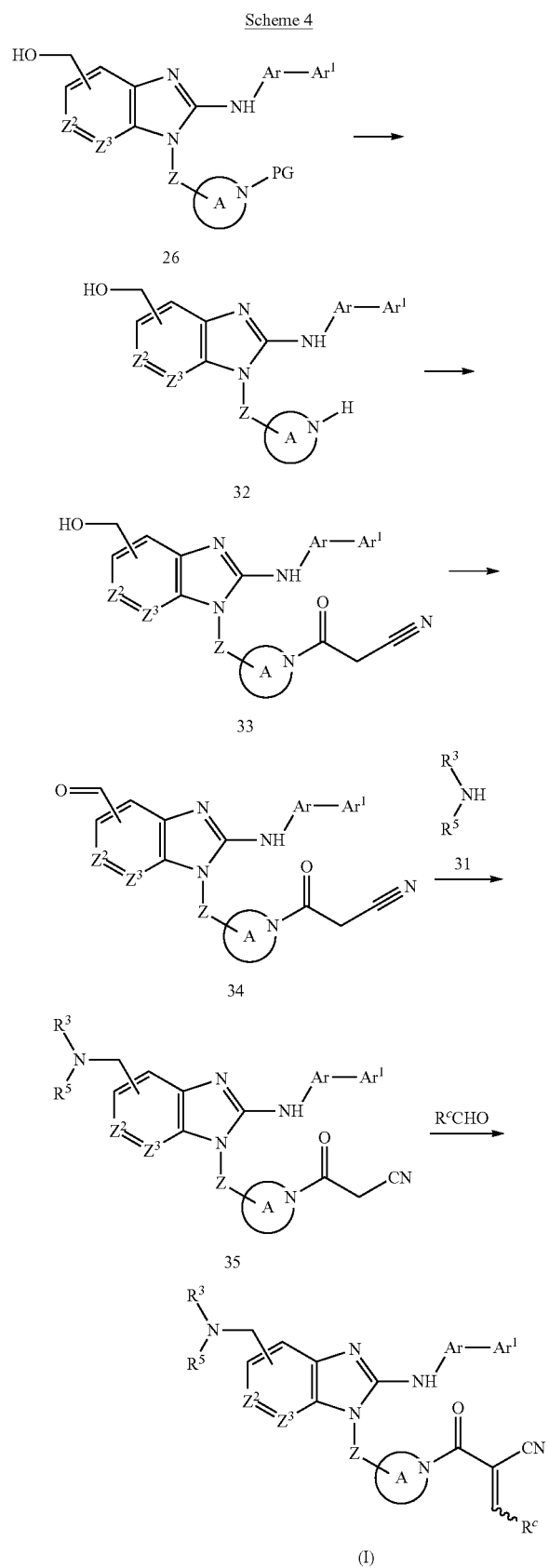

Removal of the amino protecting group PG in compound 26, followed by coupling of the resulting compound 32 with cyanoacetic acid provides a compound of formula 33. Compound 33 can be oxidized with reagents such as Dess-Martin Periodinane or PCC other standard oxidizing protocols such as the Swern oxidation and the like to afford aldehyde 34. Compound 34 can undergo reductive amination with amines 31, where $R^3$ and $R^5$ are as described in the Summary to afford compound 35. Compound 35 can be then converted to a compound of Formula (I) as described in Scheme 1 above.

Alternatively compounds of Formula (I) where $Z^1$ is CH (or C if substituted with $R^1$ or $R^2$), $R^1$ is —(CH$_2$)—NHR$^5$ where $R^5$ are as defined in the Summary, X is a ring of formula (II), $R^b$ is cyano, and other groups are as defined in the Summary can also be prepared as illustrated and described in Scheme 5 below.

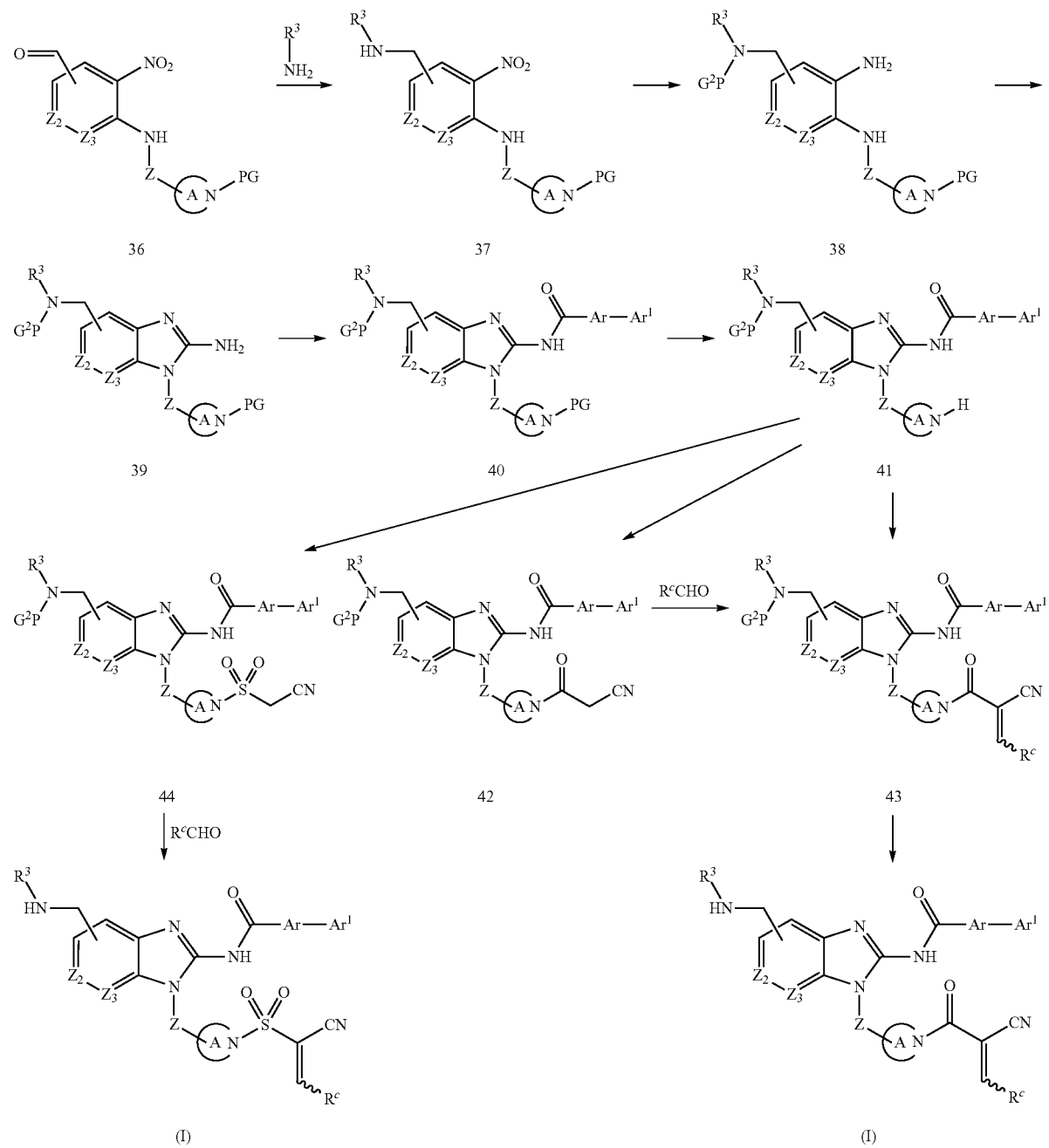

Scheme 5

Treatment of a compound of formula 36 with an amine of formula $R^3NH_2$ where $R^3$ is as defined in the Summary, provides a compound of formula 37. Protection of the resultant amine 37 with a suitable orthogonal protecting group PG$^2$ such as Alloc or Cbz, can be accomplished under standard conditions as described in T.W. Greene, Protective Groups in Organic Synthesis, John Wiley & Sons, Inc.

(1999) to afford a compound of formula 38 which can be converted to a compound of formula 42, 43, or 44 as described in Scheme 1 above. Removal of the amino protecting group then provides a compound of Formula (I).

It will be apparent to a person of ordinary skilled in the art, that substituting with amines of formula NH$_2$-alkylene-NHPG where PG is a suitable amino protecting group e.g., tert-butyl N-(2-aminoethyl)carbamate for formula (II) followed by steps described above would give compounds of Formula (I) where X is -alkyleneNH- and Y is CO or SO$_2$. Compounds of Formula (I) where R$^b$ and R$^c$ are hydrogen, can be prepared by the addition of acryloyl chloride to amines such as 41 in a solvent such as toluene or THF. Scheme 6 depicts the preparation a compound with a 2,2-dimethyl-propyl linker between the 1,3-dihydro-2H-benzo[d]imidazole ring and the Michael acceptor. Condensation of 2,2-dimethylpropane-1,3-diamine and tert-butyl (S)-(3,3-dimethylbutan-2-yl)(4-fluoro-3-nitrobenzyl)carbamate affords 45a. After protection of the primary amine as a formamide, the 2-amino-benzimidazole ring is elaborated as previously described, the formate is removed and an acrylic acid derivative is coupled and finally the Boc group is removed to afford 49b.

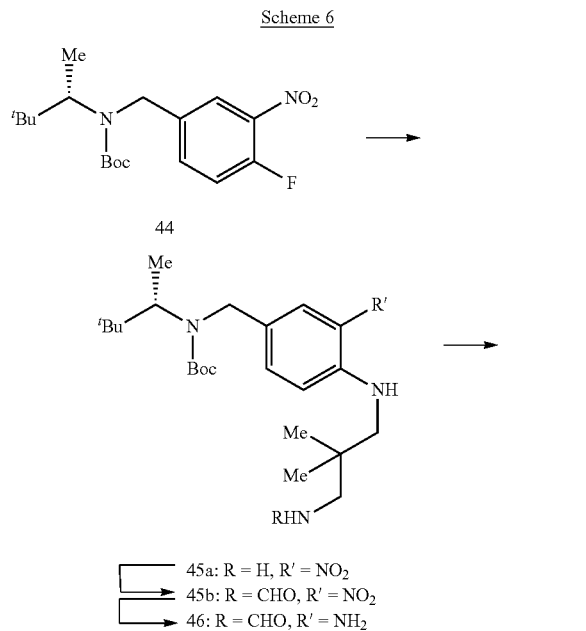

Scheme 6

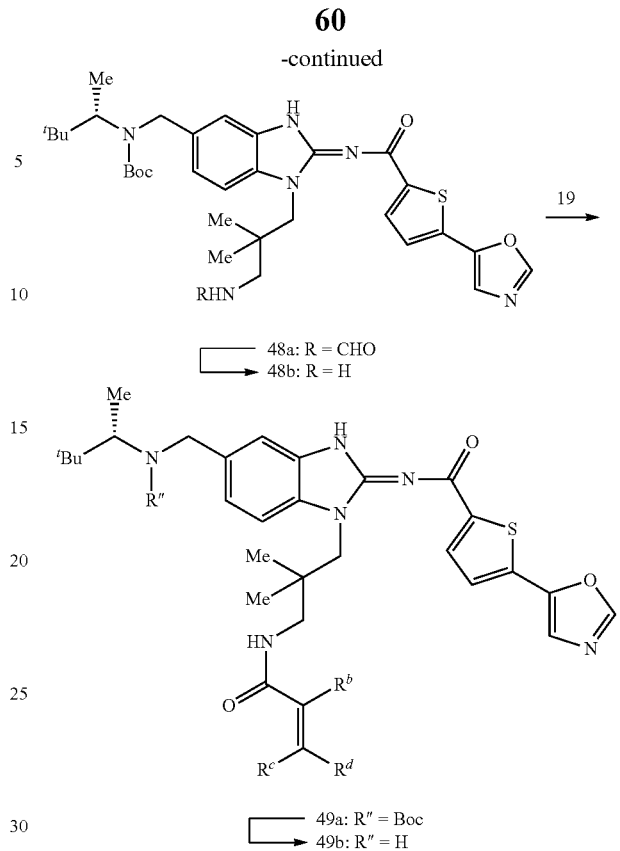

The development of Th17 cells is driven by a specific set of cytokines including TGF-β, IL-23, IL-6, IL-1β, and IL-21 all of which activate STAT3 resulting in the terminal differentiation of these IL-17 producing cells. The involvement of Th17 cells in pathogenesis was initially revealed in studies of pre-clinical models of autoimmunity including experimental autoimmune encephalopathy (EAE) and collagen-induced arthritis (see Weaver et al., Th17: an effector CD4 T cell lineage with regulatory T cell ties, Immunity 24:677-688, 2006.). Further work on pre-clinical models has linked Th17 cells and their secreted products including IL-17 to models of inflammatory bowel disease and Crohn's disease (see Ito et al., Involvement of IL-17A in the pathogenesis of DSS-induced colitis in mice, BBRC, 377:12-16, 2008) as well as models of psoriasis (see van der Fits, Imiquimod-induced psoriasis-like inflammation in mice, J. Immunol. 182:5836-5845, 2009). Additional evidence that Th17 cells and IL-17 contribute to autoimmunity is found in K/BxN transgenic mice that express autoreactive T cells and demonstrate spontaneous development of arthritis. These mice show significant reduction in Th17 gene signatures under conditions that inhibit the development of disease and blocking IL-17 with neutralizing antibodies at the time of onset of arthritis completely abrogates disease (see Wu et al., Gut-residing segmented filamentous bacteria drive autoimmune arthritis via T helper 17 cells, Immunity 32:815-827, 2010). Therefore based on a variety of pre-clinical models the link between Th17 cells and autoimmunity has been established and suggests a point of intervention in these various pathologies could be blockade of Th17 function.

In addition to diseases mediated specifically by IL17, ITK and RLK are individually implicated in a variety of disease states as described below. Accordingly, inhibition of ITK and/or RLK activity is expected therefore to be useful in treatment of these diseases.

ITK dysfunction (e.g., overexpression) has been implicated in lung inflammation, recruitment of eosinophils, production of mucus (see Mueller, et al., Attenuation of immunological symptoms of allergic asthma in mice lacking the tyrosine kinase ITK, *Journal of Immunology*, 170:5056-5063) as well as reduced airway hyperresponsiveness (see Ferrara, et al., Reduced airway hyperresponsiveness and tracheal responses during allergic asthma in mice lacking tyrosine kinase inducible T-cell kinase, *Journal of Allergy and Clinical Immunology*, 117:780-786). In addition, using knock-out mice, RNAi and chemical inhibitors, ITK has been implicated in T cell-driven inflammatory diseases of the skin (see von Bonin et al. Inhibition of the IL-2-inducible tyrosine kinase (ITK) activity: a new concept for the therapy of inflammatory skin diseases, *Exp Dermatol*, 20:41-47, 2010). ITK was found to be expressed in lymphoid tissue and upregulated in lesional skin from patients with allergic dermatitis, atopic dermatitis and psoriasis. ITK also plays a role in the pathophysiology of T cell malignancies (see Guo W. et. al., Molecular characteristics of CTA056, a novel ITK inhibitor which selectively targets malignant T cell and modulates oncomirs, Molecular Pharmacology, doi:10.1124/mol.112.079889).

Due to its role in the production of cytokines and T cells, inhibiting ITK function can reduce or inhibit the development and/or progression of multiple inflammatory disorders, autoimmune disorders, and lymphoproliferative disorders. Several drug therapies target ITK in order to treat inflammatory disorders, autoimmune disorders, and lymphoproliferative disorders. These drugs include, but are not limited to, BMS-488516 and BMS-509744 (see Lin, et al., Selective ITK inhibitors block T-cell activation and murine lung inflammation, *Biochemistry*, 43(34):11056-62), 2-amino-5-(thioaryl)thiazoles (Das, Discovery and SAR of 2-amino-5-(thioaryl)thiazoles as potent and selective ITK inhibitors, *Bioorganic and Medicinal Chemistry Letters*, 16(14):3706-12); 3-Aminopyrid-2-ones (see Charrier, et al., Discovery and Structure-Activity Relationship of 3-Aminopyrid-2-ones as Potent and Selective Interleukin-2 Inducible T-Cell Kinase (ITK) Inhibitors, *Journal of Medicinal Chemistry*, 54(7):2341-50).

There is evidence that ITK dysfunction plays a role in multiple inflammatory disorders that are affected by cytokine production, e.g., lung inflammation and pneumonia (see Lin, et al., Selective ITK inhibitors block T-cell activation and murine lung inflammation, *Biochemistry*, 43(34): 11056-62; Das, Discovery and SAR of 2-amino-5-(thioaryl)thiazoles as potent and selective ITK inhibitors, *Bioorganic and Medicinal Chemistry Letters*, 16(14):3706-12); allergic asthma (see Mueller, et al., Attenuation of immunological symptoms of allergic asthma in mice lacking the tyrosine kinase ITK, *Journal of Immunology*, 170:5056-5063; Das, Discovery and SAR of 2-amino-5-(thioaryl)thiazoles as potent and selective ITK inhibitors, *Bioorganic and Medicinal Chemistry Letters*, 16(14):3706-12); psoriasis (see Eur. J. Pharm. Sci. 2012 Oct. 9; 47(3):574-88. doi: 10.1016/j.ejps.2012.07.013. Epub 2012 Jul. 20. Inhibitors of interleukin-2 inducible T-cell kinase as potential therapeutic candidates for the treatment of various inflammatory disease conditions. Kaur M, Bahia M S, Silakari O. and Cold Spring Harb Perspect Biol. 2010 July; 2(7):a002287. Epub 2010 Jun. 2 T-cell signaling regulated by the Tec family kinase, ITK. Andreotti A. H, Schwartzberg P. L, Joseph R. E, Berg L. J.) and atopic dermatitis (see Exp Dermatol. 2011 January; 20 (1):41-7. doi: 10.1111/j.1600-0625.2010.01198.x. Inhibition of the IL-2-inducible tyrosine kinase (ITK) activity: a new concept for the therapy of inflammatory skin diseases. von Bonin A, Rausch A, Mengel A, Hitchcock M, Krüger M, von Ahsen O, Merz C, Rose L, Stock C, Martin S F, Leder G, Döcke W D, Asadullah K, Zügel U.

In one embodiment, a compound disclosed herein is administered to a mammal in need or recognized need thereof to treat an inflammatory disorder. In another embodiment, a compound disclosed herein is administered to a mammal in need or recognized need thereof to treat an inflammatory disorder characterized by excessive or undesired cytokine production or activity. In yet another embodiment, a compound disclosed herein is administered to a mammal in need or recognized need thereof to treat lung inflammation, pneumonia, allergic asthma, psoriasis, atopic dermatitis, or a combination thereof. In yet another embodiment, a compound disclosed herein is administered to a mammal in need or recognized need thereof to treat dry eye disease or uveitis.

Additionally, it is thought that ITK dysfunction affects the development and progression of autoimmune disorders (see Charrier, et al., Discovery and Structure-Activity Relationship of 3-Aminopyrid-2-ones as Potent and Selective Interleukin-2 Inducible T-Cell Kinase (ITK) Inhibitors, *Journal of Medicinal Chemistry*, 54(7):2341-50). In some embodiments, a compound disclosed herein is administered to a mammal in need or recognized need thereof to treat an autoimmune disorder.

There is also evidence that ITK overexpression results in the development and progression of T cell malignancies (e.g., T cell lymphomas and T cell leukemia) (see Guo W. et. al., Molecular characteristics of CTA056, a novel ITK inhibitor which selectively targets malignant T cell and modulates oncomirs, Molecular Pharmacology, doi:10.1124/mol.112.079889). CTA056 was found to modulate the growth of cell lines with high ITK levels, but not those with low levels or not expressing ITK at all. In addition, normal T cell growth was not affected. The effect of ITK inhibitor was via induction of apoptosis indicating a potential therapeutic mechanism for elimination of tumor cells. In addition, inhibition of ITK modulates genes that are associated with survival pathways and oncogenesis, which also supports a mechanism to inhibit tumor cell growth. In some embodiments, a compound disclosed herein is administered to a mammal in need or recognized need thereof to treat T cell malignancies, such as T cell lymphomas and T cell leukemia. In one embodiment, a compound disclosed herein is administered to a mammal in need or recognized need thereof to treat PTCL, acute lymphoblastic leukemia (T-ALL), adult T cell leukemia/lymphoma (ATL), and Seazry syndrome/cutaneous T cell lymphoma (CTCL).

The effects of ITK inhibition on Th2 responses (Andreotti et al., T-cell signaling regulated by the TEC family kinase, ITK, *Cold Spring Harb Perspect Biol*, 2(7):1-21) suggest that blockade of ITK function in T cells could lead to a shift in the relative proportions (or skewing) of the Th1 and Th2 populations in mammals treated with an ITK inhibitor. In animal models, this Th1/2 skewing affects the susceptibility to infectious agents such as *Listeria monocytogenes* and allergic asthma in animal models (see Mizuki et al., Interference between host resistance to *Listeria monocytogenes* infection and ovalbumin-induced allergic responses in mice, *Infection and Immunity*, 69(3): 1883-1888). Such T helper cell skewing has been suggested to play a role in the responses of chronic lymphocytic leukemia (CLL) patients to ibrutinib therapy through effects of ibrutinib on ITK (see Dubovsky et al., Ibrutinib is an irreversible molecular inhibitor ITK driving a Th1 selective pressure in T-lymphocytes, *Blood*, 2013, pre-published on line).). It was also suggested that the ITK activity of Ibrutinib was responsible for the suppression of Leishmaniasis in susceptible mice again through the Th1 skewing activity. In addition, it has been suggested that Th1 skewing may add to the therapeutic benefit of EGFR targeting in cancer patients by boosting local inflammatory response to the tumor (see Zaiss et al., Amphiregulin enhances regulatory T cell-suppressive function via epidermal growth factor receptor, *Immunity*, 38:1-10). Taken together, these data supports that inhibition of ITK in patients with CLL or other cancers, with the resultant skewing of the T helper cell population towards Th1 cells, could play a role in therapy both through anti-tumor activity as well as an adjuvant therapy to boost immune responses to pathogens that contribute to infections in these settings. In one embodiment, a compound disclosed herein is administered to a mammals in need or recognized need thereof to treat CLL or other cancers or infections such as Leishmaniasis that are associated with immune function suppression through skewing of T helper cell populations.

The kinase known as RLK contains several protein domains, including, a COOH-terminal kinase catalytic domain, a Src homology 2 (SH2) protein interaction domain, an SH3 domain, a palmitoylated cysteine-string motif that is required for membrane localization and a proline-rich region (see Readinger, et al., Tec kinases regulate T-lymphocyte development and function: new insights into the roles of ITK and RLK/Txk, Immunol Rev, 228(1):93-114, 2009). RLK is expressed in Th1/Th0 cells and is an important modulator of lymphocyte development and function. In some embodiments, a compound disclosed herein inhibits or decreases or enhances the activity of RLK.

RLK is a signal-transducing molecule, which consists of the tyrosine kinase cascade downstream from the T cell receptor when an antigen is presented to the T cell through the T cell receptor. RLK is phosphorylated and activated by Fyn, one of the Srk family kinases, and it phosphorylates downstream signal molecules (see Suzuki, et al., Skewed Th1 responses caused by excessive expression of RLK, a member of the Tec family of tyrosine kinases, in patients with Behcet's disease, Clin Med Res, 4(2):147-51, 2006). Upon activation, RLK translocates from cytoplasm into nucleus and regulates specifically interferon-gamma gene transcription. RLK, poly(ADP-ribose) polymerase 1, and elongation factor 1alpha make a complex to bind to interferon-gamma gene promoter region-53/-39 (RLK responsive element) to exert positive effects on transcription as a Th1 cell-associated transcription factor (see Mihara, et al., Role of TXK, a member of the Tec family of tyrosine kinases, in immune-inflammatory diseases, Int Rev Immunol, 26(5-6):333-48, 2007). In some embodiments, a compound disclosed herein modulates the activity of RLK.

Aberrant overexpression of RLK has been implicated in several immunopathologies, including, but not limited to, rheumatoid arthritis (see Mihara, et al., Role of Txk, a member of the Tec family of tyrosine kinases, in immune-inflammatory diseases, Int Rev Immunol, 26(5-6):333-48, 2007) and Behcet's disease (see Suzuki, et al., Skewed Th1 responses caused by excessive expression of Txk, a member of the Tec family of tyrosine kinases, in patients with Behcet's disease, Clin Med Res, 4(2):147-51, 2006). In some embodiments, a compound disclosed herein is administered to an individual in need thereof to treat an inflammatory disorder characterized by dysfunction of lymphocyte development and function. In some embodiments, a compound disclosed herein is administered to a mammal in need or recognized need thereof to rheumatoid arthritis, Behcet's disease, or a combination thereof.

Additionally, a reduction in RLK expression has been implicated in bronchial asthma (see Sahu, et al., Selective expression rather than specific function of RLK and ITK regulate Th1 and Th2 responses, J. Immunol, 181(9):6125-31, 2008) and atopic dermatitis (see Arakawa, et al., Differential expression of mRNA for Th1 and Th2 cytokine-associated transcription factors and suppressors of cytokine signaling in peripheral blood mononuclear cells of patients with atopic dermatitis, Clin Exp Immunol, 135(3):505-10, 2004). In some embodiments, a compound disclosed herein is administered to a mammal in need or recognized need thereof to treat an inflammatory disorder characterized by dysfunction of lymphocyte development and function. In some embodiments, a compound disclosed herein is administered to a mammal in need or recognized need thereof to asthma, atopic dermatitis, or a combination thereof.

Modulation of RLK expression should lead to the correction of aberrant immunity and, consequently, disease treatment. Accordingly, there is a need for drug therapies that modulate RLK and are therefore useful in the treatment of RLK-mediated disorders, such as those associated with inflammatory immune disorders. The compounds described herein can be used to treat RLK-related conditions, included those described herein.

The compounds of Formula (I) and/or pharmaceutically acceptable salts thereof (and embodiments thereof described herein) are useful in the treatment of ITK and RLK-mediated disorders described above, including disorders such as those associated with T cell and cytokine-mediated disorders. The compounds described herein can also inhibit other kinases such as TEC and hence can also be used for treating diseases or conditions associated with the activity of TEC.

In T cells, three members of this family, ITK, RLK, and TEC, are expressed. TEC kinase is an integral component of T cell signaling and has a distinct role in T cell activation. In some embodiments, a compound disclosed herein modulates the activity of Tec in T cell signaling and activation. Aberrant expression of Tec has been implicated in various diseases, including, but not limited to, heart disease (Zhang, et al., Stress signaling by Tec tyrosine kinase in the ischemic myocardium, Am J Physiol Heart Circ Physiol, 2993(3) H713-22, 2010), myelodysplastic syndrome (see Sato, et al., Molecular cloning and analysis of the human Tec protein-tyrosine kinase, Leukemia, 8(10):1663-72, 1994), and osteoporosis (see Shinohara, et al., Tyrosine kinases Btk and Tec regulate osteoclast differentiation by linking RANK and ITAM signals, Cell, 132(5):794-806, 2008). In some embodiments, a compound disclosed herein is administered to a mammal in need or recognized need thereof to treat an immune disorder. In some embodiments, a compound disclosed herein is administered to a mammal in need or recognized need thereof to treat cardiovascular disease, osteoporosis, or a combination thereof. In some embodiments, a compound disclosed herein is administered to a mammal in need or recognized need thereof to treat myelodysplastic syndrome thereof. The compounds described herein can be used to treat TEC-related conditions, included those described herein.

In one aspect, the present disclosure is directed to use of compound of Formula (I) and/or a pharmaceutically acceptable salt thereof (and any embodiments thereof described herein) for use as a medicament. In one embodiment, the use of compounds of Formula (I) and/or a pharmaceutically acceptable salt thereof is for treating proliferative disease (e.g., cancers). In another aspect, the present disclosure is directed to the use of a compounds of Formula (I) and/or a pharmaceutically acceptable salt thereof (and any embodiments thereof described herein) for treatment of diseases associated with axonal regeneration, or spinal cord injury. In another embodiment, the disease is an inflammatory disorder chosen from asthma, allergic dermatitis, atopic dermatitis and psoriasis.

In further aspects, the present disclosure is directed to the use of a compounds of Formula (I) and/or a pharmaceutically acceptable salt thereof (and any embodiments thereof described herein) for treatment of psoriasis, alleviation of inflammation during organ transplant, treatment of asthma, rheumatoid arthritis, osteoporosis, cardiovascular disease, or any other disease described above. In any of the aforementioned aspects involving the treatment of proliferative disorders, including cancer, are further embodiments comprising administering the compound of Formula (I) and/or a pharmaceutically acceptable salt thereof in combination with at least one additional agent selected from an anticancer agent or an agent that modulates growth or regeneration of axons. When combination therapy is used, the agents are administered simultaneously or sequentially.

Testing

The RLK and ITK inhibitory activity, residence time of the inhibitor RLK or inhibitor ITK bound complex, and the ability of the of the compounds of the present disclosure to form irreversible covalent bond or reversible covalent bond, in particular irreversible covalent bond with Cys 442 (UniprotKB Sequence ID Q08881) of ITK and Cys351 of RLK can be tested using the in vitro and/or in vivo assays described in working Examples below.

The kinase inhibitory activity of the compounds of the present disclosure can be tested by methods well known the art. The RLK and/or ITK inhibitory activity of the compounds and/or a pharmaceutically acceptable salt thereof of the present disclosure can be tested using the in vitro and in vivo assays described in Biological Examples 1, 2, 3, 4, 5, and 9 below. A determination of kinase inhibitory activity by any of those assays is considered to be kinase inhibitory activity within the scope of this disclosure even if any or all of the other assays do not result in a determination of kinase inhibitory activity.

Without being bound to any specific mechanistic theory, in those embodiments wherein the compound of the present disclosure is a reversible covalent inhibitor, it is believed that the cysteine sulfhydryl group and a carbon atom forming part of the carbon-carbon double bond in the group —X—Y—C($R^b$)=CHR$^c$ where $R^b$ is cyano, (see Formula (I)) of the compound of the present disclosure can form a reversible, i.e., labile, covalent bond, defined herein, such as wherein Cys 442 of ITK and Cys351 of RLK attacks an electron deficient carbon atom of the carbon-carbon double bond in the group —X—Y—C($R^b$)=CHR$^c$ in the compound of present disclosure to form a labile thiol adduct (e.g., Michael reaction with cysteine). In contrast, wherein the compounds of the present disclosure is an irreversible covalent inhibitor, it is believed that the cysteine sulfhydryl group and a carbon atom forming part of the carbon-carbon double bond in the group —X—Y—C($R^b$)=CR$^c$ where $R^b$ is hydrogen, (see Formula (I)) of the compound of the present disclosure can form an irreversible, i.e., non-labile, covalent bond, defined herein, such as wherein Cys 442 of ITK and Cys351 of RLK attacks an electron deficient carbon atom of the carbon-carbon double bond in the group —X—Y—C($R^b$)=CHR$^c$ in the compound of present disclosure to form a permanent thiol adduct (e.g., Michael reaction with cysteine).

In some embodiments, wherein the compounds of the present disclosure is a reversible covalent inhibitor, the electron deficient carbon atom of the olefin is distal to the carbon attached to the $R^b$ group (where $R^b$ is not hydrogen) and to the electron withdrawing —X—Y— moiety (see Formula (I)) in the compounds of the present disclosure. Therefore, the combination of the $R^b$ group (where $R^b$ is not hydrogen) and the "—X—Y—" moieties and the olefinic moiety to which they are bonded in the compounds of the present disclosure can increase the reactivity of the olefin to form a thiol adduct with the active site cysteine residue in ITK and RLK.

Accordingly, the compounds of the present disclosure which are reversible covalent inhibitors bind with ITK and RLK in two different manner. In addition to the labile covalent binding, discussed above, they also form non-covalent binding (e.g., via van der Waals binding, hydrogen binding, hydrophobic binding, hydrophilic binding, and/or electrostatic charge binding) with RLK and ITK, the non-covalent binding being sufficient to at least partially inhibit the kinase activity of RLK and ITK.

As disclosed herein, the labile covalent binding between the reversible covalent inhibitor of the disclosure and RLK and ITK occurs between the olefin in the inhibitor and the cysteine 351 residue of RLK and cysteine 442 residue of ITK at or near the site where the inhibitor has the aforementioned non-covalent binding with RLK and ITK respectively.

As is evident, the compounds of the present disclosure which are reversible covalent inhibitors have both a cysteine-mediated covalent binding and a non-covalent binding with RLK and ITK. This is in contrast with non-covalent reversible inhibitors which inhibit the ITK only via non-covalent binding and lack the cysteine-mediated covalent binding.

The binding of the compounds of the present disclosure which are reversible covalent inhibitors with RLK and ITK in the two different manners mentioned above provides a reversible covalent inhibitor having a slow off-rate and a protracted duration of action, in some instances comparable to an irreversible covalent inhibitor without forming permanent irreversible protein adducts. The difference between irreversible and reversible covalent inhibitors, particularly the compounds disclosed herein, can be ascertained utilizing assays disclosed herein.

In general, the binding involved in an inhibitor that forms a reversible covalent bond with RLK and ITK is stable when RLK and ITK are in certain configurations and susceptible to being broken when the RLK and ITK is in different configurations (in both cases under physiologic conditions), whereas the interaction between an inhibitor that forms an irreversible covalent bond is stable under physiologic conditions even when the RLK and ITK are in different configurations.

A reversible covalent bond often imparts unique properties related to the residence time of the compound within the cysteine-containing binding site. In this context, residence time refers to the temporal duration of the compound-target complex under different conditions (see Copeland R A, Pompliano D L, Meek T D. Drug-target residence time and its implications for lead optimization. *Nat. Rev. Drug Discov.* 5(9), 730-739 (2006).

The presence of a reversible covalent bond to a reversible covalent inhibitor as disclosed herein can lead to an extended residence time when compared to a compound that does not form a covalent bond with RLK and ITK. In one embodiment disclosed herein the compounds of the present disclosure that are reversible covalent inhibitors have a residence time of at least about 1 h. Residence time may be measured using an occupancy assay in a biochemical or cellular environment (see Biological Example 2 below). Additionally, residence time may be measured using a functional assay following a defined wash-out period.

Compounds that form an irreversible covalent bond in an irreversible covalent inhibitor as disclosed herein share these extended residence time properties but may nonetheless be differentiated from reversible covalent inhibitor using a reversibility assay. The ability of the compound of the disclosure to form reversible or irreversible covalent bond with a target protein such as RLK and ITK can be determined by the assays described in Biological Examples 2, 6, 7, or 8 below. A determination of the binding reversibility of the covalent bond between the cysteine residue and the olefinic bond of the compound of the disclosure by any of Biological Examples 2, 6-8 below is considered to be binding reversibility within the scope of this disclosure even if one or both of the other methods does not result in a determination of binding reversibility. The ability of the compound of the disclosure to form an irreversible covalent bond with Cys351 of RLK and Cys442 of ITK can be determined by Biological Example 6, Method B below.

Administration and Pharmaceutical Composition

In general, the compounds of this disclosure will be administered in a therapeutically effective amount by any of the accepted modes of administration for agents that serve similar utilities. Therapeutically effective amounts of compounds disclosed herein may range from about 0.01 to about 200 mg per kg mammal body weight per day, which can be administered in single or multiple doses. Preferably, the dosage level will be about 0.1 to about 100 mg/kg per day; more preferably about 0.5 to about 50 mg/kg per day. For oral administration, the compositions can be provided in the form of tablets containing about 1 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compounds disclosed herein, i.e., the active ingredient, will depend upon numerous factors such as the severity of the disease to be treated, the age and relative health of the subject, the potency of the compound being utilized, the route and form of administration, and other factors.

In general, compounds disclosed herein will be administered as pharmaceutical compositions by any one of the following routes: oral, systemic (e.g., transdermal, intranasal, or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compounds disclosed herein in non-toxic, aid administration, and do not adversely affect the therapeutic benefit of the compounds disclosed herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

The compounds of the present disclosure can also be administered intranasally. Intranasal formulations are known in the art e.g., see U.S. Pat. Nos. 4,476,116, 5,116,817 and 6,391,452, each of which is incorporated herein by reference. The choice of excipients will depend upon the nature of the nasal dosage form e.g., solutions, suspensions, or powder. For administration by inhalation, the compounds of the present disclosure may be in the form of solutions, suspensions, and powders. These formulations are administered as an aerosol, a mist or a powder and can be delivered from pressurized packs or a nebulizer with a suitable propellant such as dichlorodifluoromethane, trichlorofluoromethane, nitrogen, carbon dioxide, etc. In the case of a pressurized aerosol, the dosage unit may be determined by providing a valve to deliver a metered amount. Capsules and cartridges for use in an inhaler may be formulated containing a powder mix of the compound disclosed herein and a suitable powder base such as lactose or starch.

Topical formulation can be liquids, suspension, emulsions, and the like, and can be prepared by methods well known in the art. The formulation will contain, on a weight percent (wt %) basis, from about 0.01-99.99 wt % of a compound disclosed herein based on the total formulation, with the balance being one or more suitable pharmaceutical excipients and can be administered in single or multiple doses. Suitable excipients include polymers, surfactants, buffering or pH adjusting agents, tonicity or osmotic adjusting agent(s), preservatives, and/or dispersing agents. Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of Formula (I) based on the total formulation, with the balance being one or more suitable pharmaceutical excipients. Preferably, the compound is present at a level of about 1-80 wt %.

The compounds of the present disclosure may be used in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of the present disclosure is used contemporaneously with one or more other drugs, a pharmaceutical composition in unit dosage form containing such other drugs and the compound of the present disclosure is preferred. However, the combination therapy may also include therapies in which the compound of the present disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound disclosed herein.

The above combinations include combinations of a compounds disclosed herein not only with one other active compound, but also with two or more other active compounds. Likewise, compounds disclosed herein may be used in combination with other drugs that are used in the prevention, treatment, control, amelioration, or reduction of risk of the diseases or conditions for which compounds disclosed herein are useful. Such other drugs may be administered, by a route and in an amount commonly used therefore, contemporaneously or sequentially with a compound disclosed herein. When a compound disclosed herein is used contemporaneously with one or more other drugs, a pharmaceutical composition containing such other drugs in addition to the compound disclosed herein is preferred. Accordingly, the pharmaceutical compositions of the present disclosure also include those that also contain one or more other active ingredients, in addition to a compound disclosed herein. The weight ratio of the compound disclosed herein to the second active ingredient may be varied and will depend upon the effective dose of each ingredient. Generally, an effective dose of each will be used.

Where the mammal is suffering from or at risk of suffering from an autoimmune disease, an inflammatory disease, or an allergy disease, a compound disclosed herein can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, anticholinergics, B cell inhibitors such as anti-CD19, 20, 22 antibodies, and BTK inhibitors such as Ibrutinib.

Where the mammal is suffering from or at risk of suffering from a proliferative disorder, the subject can be treated with a compound disclosed herein in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, PD184352, or Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound disclosed herein include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound disclosed herein include adriamycin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate;

melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound disclosed herein include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; fla-
vopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin;

sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound disclosed herein include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound disclosed herein include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound disclosed herein include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound disclosed herein include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with a compound disclosed herein include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleuterobins (such as Desmethyleleutherobin, Desaetyleleutherobin, Isoeleutherobin A, and Z-Eleutherobin), Caribaeoside, Caribaeolin, Halichondrin B, D-64131 (Asta *Medica*), D-68144 (Asta *Medica*), Diazonamide A, A-293620 (Abbott), NPI-2350 (Nereus), Taccalonolide A, TUB-245 (Aventis), A-259754 (Abbott), Diozostatin, (-)-Phenylahistin (also known as NSCL-96F037), D-68838 (Asta *Medica*), D-68836 (Asta *Medica*), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi). Yet another class of anticancer agent that can be used in combination with the compounds of the present disclosure include PD-1 inhibitors e.g, Nivolumab, MK-3475 also known as Lambrolizumab (Merck) and PDL1 inhibitors e.g., MPDL3280A (Genentech) and MEDI-4736 (Astra Zeneca).

EXAMPLES

The following preparations of compounds of Formula (I) and intermediates are given to enable those skilled in the art to more clearly understand and to practice the present disclosure. They should not be considered as limiting the scope of the disclosure, but merely as being illustrative and representative thereof. The ～ line on the alkene bond in the compounds below means that the compound is isolated as pure E, pure Z or a mixture of the E and Z isomers of said compound.

Synthetic Examples

Intermediate 1

Synthesis of tert-butyl 4-(2-imino-2,3-dihydro-1H-benzo[d]imidazol-1-yl)piperidine-1-carboxylate

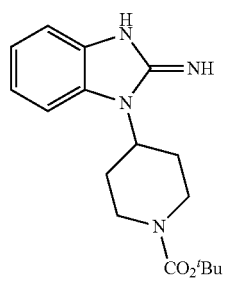 [SMILES: CC(C)(C)OC(=O)N1CCC(n2c(=N)[nH]c3ccccc32)CC1]

Step 1—In a 100 mL three necked round bottom (RB) flask, 1-fluoro-2-nitrobenzene (0.0353 g, 0.0071 mol) was taken up in acetonitrile (20 mL) and DIPEA (2.75 g, 0.0213 mole) was added dropwise at room temperature (RT). After completion of addition, the reaction mixture was stirred for 15 min at same temperature followed by slow addition of tert-butyl 4-aminopiperidine-1-carboxylate (1.71 g, 0.0085 mole) over 15 min at the same temperature. After completion of the addition, the reaction mixture was stirred for 16 h at RT. The completion of the reaction was monitored on TLC. After completion of the reaction, acetonitrile was distilled out and water was added to the residue. The aqueous phase was extracted with ethyl acetate and the combined organic layer was dried over Na$_2$SO$_4$, filtered and concentrated to afford crude product which was subjected for the column purification to yield 0.9 g of tert-butyl 4-(2-nitrophenyl-amino)piperidine-1-carboxylate.

Step 2—To a suspension of 10% dry Pd/C (0.18 g, 10% w/w) in methanol (15 mL) was added tert-butyl 4-(2-nitrophenylamino)piperidine-1-carboxylate (1.8 g, 0.0056 mole) in methanol (15 mL) under N$_2$ atmosphere. Hydrogen gas was added to the reaction mixture for 1.5 h at RT. The completion of the reaction was monitored by TLC using EtOAc:hexanes (7:3). After completion of the reaction, reaction mixture was filtered through Celite® and washed with methanol and the filtrate was concentrated to yield 1.4 g of tert-butyl 4-(2-aminophenyl-amino)piperidine-1-carboxylate.

Step 3—To a flask charged with tert-butyl 4-(2-aminophenylamino)piperidine-1-carboxylate (1.4 g, 0.0048 mole) was added ethanol (25 mL). Cyanogen bromide (0.61 g, 0.0058 mole) was then added at RT and the reaction mixture was stirred for 3 h. The completion of the reaction was monitored by TLC using CH$_2$Cl$_2$:methanol (9:1). After completion of the reaction, ethanol was distilled out and saturated NaHCO$_3$ solution was added to adjust pH basic. The reaction mixture was stirred for 1 h then filtered it and washed with water. The organic phase was dried over sodium sulfate, filtered and the solvent removed to afford 1.5 g of tert-butyl 4-(2-imino-2,3-dihydro-1H-benzo[d]imidazol-1-yl)piperidine-1-carboxylate.

Intermediate 2

Synthesis of tert-butyl 3-(2-imino-2,3-dihydro-1H-benzo[d]imidazol-1-yl)piperidine-1-carboxylate

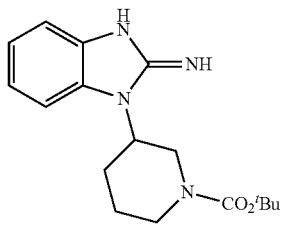 [SMILES: CC(C)(C)OC(=O)N1CCCC(n2c(=N)[nH]c3ccccc32)C1]

Step 1—A 250 mL 3 neck RB flask was charged with 1-fluoro-2-nitrobenzene (3.52 g, 0.02496 mole) and acetonitrile (50 mL) under N$_2$ atmosphere. DIPEA (13 mL, 0.075 mole) was added followed by slow addition of tert-butyl 3-aminopiperidine-1-carboxylate (5.0 g, 0.02496 mole) at RT and the reaction mixture was stirred at RT for 16 h. The reaction was monitored on TLC using EtOAc:hexanes (4:6) as a mobile phase. After 32 h, water was added to the reaction mixture and product was extracted with EtOAc. The combined organic layer was dried over Na$_2$SO$_4$ and evaporated to get the crude product which was subjected for the column purification. The crude compound was purified by column chromatography using 60-120 mesh size neutral silica by eluting the crude product with 3-5% EtOAc in hexanes to yield 1.7 g of tert-butyl 3-(2-nitrophenylamino)-piperidine-1-carboxylate.

Step 2—A 100 mL 3 neck RB flask, was charged with 10% Pd/C (0.180 g, 10% w/w) and methanol (15 mL) then a solution of tert-butyl 3-(2-nitrophenylamino)piperidine-1-carboxylate (1.7 g, 0.00528 mole) in methanol (15 mL) was added under N$_2$ atmosphere. A hydrogen was maintained over the reaction mixture for 2 h at RT. After completion of the reaction, the reaction mixture was filtered through Celite® and washed with methanol and filtrate was concentrated to yield 1.4 g of tert-butyl 3-(2-aminophenyl-amino) piperidine-1-carboxylate.

Step 3:—A 100 mL RB flask was charged with tert-butyl 3-(2-aminophenylamino)piperidine-1-carboxylate (1.4 g, 0.00481 mole) and ethanol (30 mL). Cyanogen bromide (0.61 g, 0.00577 mole) was added at RT and stirred for 2 h. After completion of the reaction, the pH of the reaction mixture was made basic by drop wise addition of saturated NaHCO$_3$ solution and product was extracted with CH$_2$Cl$_2$.

The organic layer was dried over Na₂SO₄ and evaporated. The crude product was purified by column chromatography using 60-120 mesh size neutral silica and eluting the compound with 3-4% methanol in CH₂Cl₂ to yield 1.3 g of tert-butyl 3-(2-imino-2,3-dihydro-1H-benzo[d]imidazol-1-yl)piperidine-1-carboxylate. LC-MS (ES, m/z): 317.3 [M+H].

Intermediate 3

Synthesis of tert-butyl 3-(5-(((benzyloxycarbonyl)((S)-3,3-dimethylbutan-2-yl)amino)methyl)-2-imino-2,3-dihydro-1H-benzo[d]imidazol-1-yl)piperidine-1-carboxylate

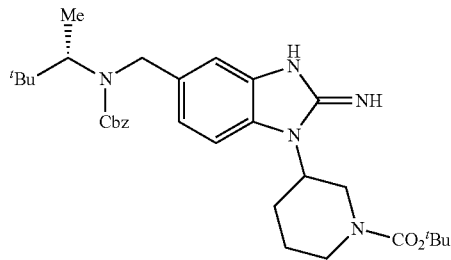 [SMILES: C[C@H](N(Cc1ccc2c(c1)[nH]c(=N)n2C1CCCN(C(=O)OC(C)(C)C)C1)C(=O)OCc1ccccc1)C(C)(C)C]

Step 1—To a single necked RB flask were added 4-fluoro-3-nitrobenzaldehyde (8.5 g, 0.0502 mole) and DIPEA (25.8 mL, 0.1507 mole) in acetonitrile (85 mL) followed by addition of tert-butyl 3-aminopiperidine-1-carboxylate (15 g, 0.0753 mole) at RT and the reaction mixture was stirred at RT for 20 h. The reaction mixture was diluted with water and extracted with ethyl acetate. The combined organic layer was dried over sodium sulfate and concentrated under vacuum to give crude product, which was purified by column chromatography eluting with 25% ethyl acetate: hexanes to yield 13.5 g of tert-butyl 3-(4-formyl-2-nitrophenylamino)piperidine-1-carboxylate.

Step 2—To a 500 mL three necked RB flask were added tert-butyl 3-(4-formyl-2-nitrophenylamino)piperidine-1-carboxylate (13.5 g, 0.0386 mole) and (S)-3,3-dimethylbutan-2-amine (3.9 g, 0.0386 mole) in ethylene dichloride (208 mL) and maintained under a nitrogen atmosphere at RT. After 10 min., the reaction mixture was stirred at RT and glacial acetic acid (0.1 ml) and NaBH(OAc)₃ (0.0579 mole) were added to reaction mixture. The reaction was stirred at RT for 6 h. After completion of the reaction, the reaction mixture was diluted with water and extracted with CH₂Cl₂. The combined organic layer was dried over sodium sulfate and concentrated under vacuum to yield 18 g of 3-(4-(((S)-3,3-dimethylbutan-2-ylamino)methyl)-2-nitrophenylamino)piperidine-1-carboxylate.

Step 3—To a 250 mL three necked RB flask were added tert-butyl 3-(4-(((S)-3,3-dimethylbutan-2-ylamino)methyl)-2-nitrophenylamino)piperidine-1-carboxylate (3.8 g, 0.0087 mole), NaOH (0.77 g, 0.0192 mole) in water (38 mL) and the mixture was cooled to 0° C.-5° C. Benzyl chloroformate (1.88 mL, 0.0131 mole) was added dropwise to reaction mixture at same temperature and then allowed to warm to RT. Dioxane (15 mL) was added and the reaction mixture was stirred at RT for 4 h. After completion of reaction, the reaction mixture was acidified with dilute HCl up to the pH between 3 and 4, then extracted with ethyl acetate. Combined organic layer was dried over sodium sulfate, concentrated to give crude product which was purified by column chromatography eluting with 5-10% ethyl acetate in hexanes to afford 4.0 g of tert-butyl 3-(4-(((benzyloxycarbonyl)((S)-3,3-dimethylbutan-2-yl)amino)methyl)-2-nitrophenylamino)-piperidine-1-carboxylate.

Step 4—To a 250 mL single necked RB flask were added tert-butyl 3-(4-(((benzyloxy-carbonyl)((S)-3,3-dimethylbutan-2-yl)amino)methyl)-2-nitrophenylamino)piperidine-1-carboxylate (4 g, 0.0070 mole) in methanol (80 mL) and saturated NH₄Cl solution (80 mL) and maintained at RT. Zn powder (4 g) was added by portionwise. The reaction mixture was heated at 60° C. for 2 h. After completion of the reaction, methanol was evaporated under vacuum and the reaction mixture was filtered to remove the Zn. The filtrate was diluted with ethyl acetate and washed with water. The organic layer was dried over sodium sulfate and concentrated to yield 2.8 g of tert-butyl 3-(2-amino-4-(((benzyloxycarbonyl) ((S)-3,3-dimethylbutan-2-yl)amino)methyl)-phenylamino)-piperidine-1-carboxylate.

Step 5—To a 250 mL three necked RB flask were added tert-butyl 3-(2-amino-4-(((benzyloxycarbonyl)((S)-3,3-dimethylbutan-2-yl)amino)methyl)phenylamino)piperidine-1-carboxylate (2.8 g, 0.0052 mole) and ethanol (56 mL) followed by portion wise addition of cyanogen bromide (0.66 g, 0.0062 mole) at RT. The reaction was stirred for 2 h. After completion of the reaction, the reaction mixture was concentrated under vacuum and diluted with saturated NaHCO₃ solution, then extracted with ethyl acetate. The combined organic layer was dried over sodium sulfate and concentrated to yield 2.5 g of tert-butyl 3-(5-(((benzyloxycarbonyl)((S)-3,3-dimethylbutan-2-yl)amino)methyl)-2-imino-2,3-dihydro-1H-benzo[d]imidazol-1-yl)piperidine-1-carboxylate. LC-MS (ES, m/z): 564.6 [M+H].

Intermediate 4

Synthesis of 2-ethoxy-2-methylpropanal

Step 1—In a 500 mL 3 neck RB flask was dissolved 2-bromo-2-methylpropanoic acid (40 g, 239.5 mmol) in ethanol (320 mL) and the solution was cooled to 0 to 5° C. followed by dropwise addition of DIPEA (87.4 mL, 502.9 mmol) at 0 to 5° C. The reaction mixture was stirred at 0° C. for 30 min. The reaction mixture was warmed to 40° C. for 16 h. After 16 h, the reaction mixture was cooled to RT, ethanol was removed in vacuo which produced a thick white slurry. Diethyl ether and water was added to the slurry and cooled to 0° C. The mixture was acidified with 10% HCl (50 mL) and the organic layer was separated and washed with brine. To the organic phase was added 10% aq NaHSO₃ and the mixture was stirred at RT for 6 h. The biphasic mixture was acidified with 10% HCl (50 mL) to the pH 1.0±0.5. The organic phase was washed with brine (100 mL), dried over sodium sulfate, filtered and concentrated to afford 30 g of 2-ethoxy-2-methylpropanoic acid which was used without further purification.

Step 2—A 500 mL three neck RB flask was charged with 2-ethoxy-2-methylpropanoic acid (30 g, 227.2 mmol) in ethanol (300 mL) and the solution cooled to 0° C. Thionyl chloride (49.7 mL, 681.8 mmol) was added dropwise at 0° C. The reaction mixture was heated at refluxed for 3 h. After completion of the reaction, thionyl chloride and ethanol were evaporated in vacuo and the residue was cooled to 0° C. and basified with saturated NaHCO₃ solution and extracted with CH$_2$Cl$_2$, dried over sodium sulfate, filtered and concentrated to give 32 g of ethyl 2-ethoxy-2-methyl-propanoate.

Step 3—A 500 mL three neck RB flask was charged with ethyl 2-ethoxy-2-methyl-propanoate (16 g, 100 mmol) in dry THF (133 mL) and cooled to 0 to −10° C. A 1M solution of LiAlH$_4$ in THF (100 mL, 100 mmol) was added dropwise at 0 to −10° C. and the reaction mixture was stirred at 0° C. for 3 h. After completion of the reaction, the reaction mixture was quenched with sat. NH$_4$Cl solution and filtered through Buchner funnel to remove colloidal precipitates. The filtrate was extracted with ethyl acetate. The combined organic phase was dried over sodium sulfate and evaporated to afford 9 g of 2-ethoxy-2-methylpropan-1-ol.

Step 4—A 100 mL single neck RB flask was charged with 2-ethoxy-2-methylpropan-1-ol (9 g, 76.2 mmol) in dry CH$_2$Cl$_2$ (20 mL) and the solution was cooled to 10° C. Pyridinium chlorochromate was added to the reaction mixture portion wise at 10° C. and the reaction mixture was stirred at RT for 16 h. The progress of the reaction was monitored by TLC using neat CH$_2$Cl$_2$ as a mobile phase. After the reaction was complete, the reaction mixture was poured directly onto a column and eluted with neat CH$_2$Cl$_2$. The solvent was distilled at 50° C. to yield 5 g of 2-ethoxy-2-methylpropanal.

Intermediate 5

Synthesis of tert-butyl 2-((5-(((benzyloxycarbonyl)-((S)-3,3-dimethylbutan-2-yl)amino)methyl)-2-imino-2,3-dihydro-1H-benzo[d]imidazol-1-yl)methyl)pyrrolidine-1-carboxylate

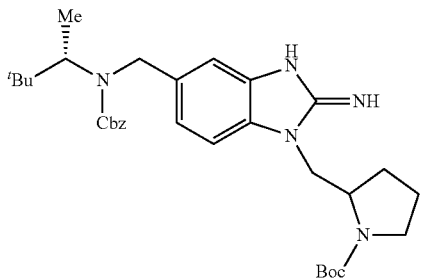 [SMILES: C[C@H](N(Cc1ccc2c(c1)[nH]c(=N)n2CC1CCCN1C(=O)OC(C)(C)C)C(=O)OCc1ccccc1)C(C)(C)C]

Step 1—To a 250 mL three necked RB flask charged with 4-fluoro-3-nitrobenzaldehyde (7.0 g, 0.0416 mole) was added in acetonitrile (100 mL) followed by addition of DIPEA (21.5 mL, 0.1248 mole) and the resulting mixture was stirred at RT for 10 min. tert-butyl 2-(aminomethyl)-pyrrolidine-1-carboxylate (12.5 g, 0.0624 mole) in acetonitrile (100 mL) was added dropwise after which the reaction was stirred at RT for 16 h. After 16 h, the reaction mixture was concentrated, diluted with water and extracted with CH$_2$Cl$_2$. The combined organic layers were dried over sodium sulphate and concentrated to afford a crude product which was purified using column purification eluting with 10% ethyl acetate in hexanes to yield 14 g of tert-butyl 2-((4-formyl-2-nitrophenylamino)methyl)pyrrolidine-1-carboxylate.

Step 2—To a 500 mL three necked RB flask maintained under a nitrogen atmosphere were added tert-butyl 2-((4-formyl-2-nitrophenylamino)methyl)pyrrolidine-1-carboxylate (14 g, 0.0400 mole) and (S)-3,3-dimethylbutan-2-amine (4.04 g, 0.0400 mole) in 1,2 dichloroethane (300 mL) and the mixture stirred at RT for 10 min. Acetic acid (1.24 mL, catalytic amount) and NaBH(OAc)$_3$ (12.7 g, 0.0601 mole) were added to the reaction mixture and the reaction mixture was stirred at RT for 6 h. After completion of the reaction, the reaction mixture was poured into saturated Na$_2$CO$_3$ solution followed by extraction with CH$_2$Cl$_2$. The combined organic layers were dried over sodium sulphate and concentrated to yield 17 g of tert-butyl 2-((4-(((S)-3,3-dimethylbutan-2-ylamino)methyl)-2-nitrophenylamino)methyl)-pyrrolidine-1-carboxylate.

Step 3—A 50 mL three necked RB flask was charged with tert-butyl 2-((4-(((S)-3,3-dimethylbutan-2-ylamino)methyl)-2-nitrophenylamino)methyl)pyrrolidine-1-carboxylate (2.0 g, 0.0046 mole), NaOH (0.40 g, 0.0101 mole), 1,4-dioxane (10 mL) and water (20 mL) and the reaction mixture was cooled it to 10° C. Benzyl chloroformate (0.98 mL, 0.0069 mole) was added dropwise to the cooled reaction mixture and the reaction mixture was allowed to warm to RT then stirred for 3 h. After the reaction was complete, the reaction mixture was washed with 1N HCl and saturated NaHCO$_3$ solution. The organic layer was dried over sodium sulphate and concentrated to yield 1.7 g of tert-butyl 2-((4-(((benzyloxycarbonyl)((S)-3,3-dimethylbutan-2-yl)amino) methyl)-2-nitrophenylamino)-methyl)pyrrolidine-1-carboxylate.

Step 4—To a 50 mL three necked RB flask containing tert-butyl 2-((4-(((benzyloxycarbonyl)((S)-3,3-dimethylbutan-2-yl)amino)methyl)-2-nitrophenylamino)methyl)pyrrolidine-1-carboxylate (1.7 g, 0.00298 mole) was added in methanol (17 mL) followed by zinc dust (0.5 g, 0.0149 mole) and saturated NH$_4$Cl solution (8.5 mL). The resultant mixture was heated at 50° C. for 2 h with stirring. After completion of the reaction, the reaction mixture was filtered through a Celite® bed, washed with methanol and the filtrate was concentrated to give the crude product. Water was added and the product was extracted with EtOAc. The combined organic layer was dried over sodium sulphate, concentrated to give the crude compound which was purified by column chromatography to yield 1.3 g of tert-butyl 2-((2-amino-4-(((benzyloxycarbonyl)((S)-3,3-dimethyl-butan-2-yl)amino) methyl)-phenylamino)methyl)pyrrolidine-1-carboxylate.

Step 5—A 50 mL three necked RB flask under nitrogen atmosphere was charged with a solution of tert-butyl 2-((2-amino-4-(((benzyloxycarbonyl)((S)-3,3-dimethylbutan-2-yl)amino)methyl)phenylamino-methyl)pyrrolidine-1-carboxylate (1.3 g, 0.00241 mole) and ethanol (13 mL) followed by addition of cyanogen bromide (0.30 g, 0.00289 mole) at RT. The mixture was stirred at RT for 16 h and progress of the reaction was monitored on TLC using CH$_2$Cl$_2$: methanol (9:1) as a mobile phase. After the reaction was complete, the reaction mixture was concentrated under vacuum, diluted with saturated NaHCO$_3$ solution and extracted with ethyl acetate. The combined organic layer was dried over sodium sulphate and concentrated to give the crude product which was purified by column chromatography eluting the compound with 1.5-2.0% methanol in chloroform to afford 1.2 g of tert-butyl 2-((5-(((benzyloxycarbonyl)-((S)-3,3-dimethyl-butan-2-yl)amino)methyl)-2-imino-2,3-dihydro-1H-benzo[d]imidazol-1-yl)methyl) pyrrolidine-1-carboxylate. LC-MS (ES, m/z): 564.7 [M+H].

Intermediate 6

Synthesis of (R)-tert-butyl 2-((2-amino-5-(((benzy-loxy)carbonyl)((S)-3,3-dimethylbutan-2-yl)amino)methyl)-1H-benzo[d]imidazol-1-yl)methyl)pyrroli-dine-1-carboxylate

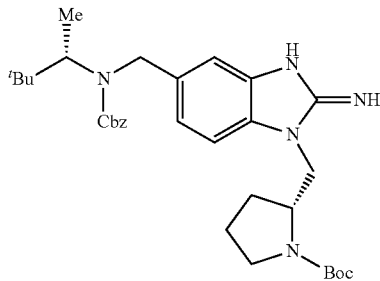 [SMILES: C[C@H](N(Cc1ccc2c(c1)[nH]c(=N)n2C[C@H]1CCCN1C(=O)OC(C)(C)C)C(=O)OCc1ccccc1)C(C)(C)C]

Step 1—A 500 mL three neck RB flask was charged with 4-fluoro-3-nitrobenzaldehyde (10.0 g, 59 mmol) and acetonitrile (100 mL) followed by DIPEA (22.8 gm, 177 mmol). After stirring 10 min. at RT, (S)-tert-butyl 2-(aminomethyl)pyrrolidine-1-carboxylate (14.2 g, 70 mmol) in acetonitrile (100 mL) was added dropwise and the reaction mixture was stirred at RT for 24 h. The reaction mixture was concentrated, diluted with water and extracted with $CH_2Cl_2$. The combined organic layer were dried over sodium sulfate and concentrated. The crude product was purified by column chromatography eluting with 10% ethyl acetate in hexanes to yield 18.2 g of (S)-tert-butyl 2-((4-formyl-2-nitrophenylamino)-methyl)pyrrolidine-1-carboxylate.

Step 2—A 1 L three neck RB flask under nitrogen atmosphere was charged with (S)-tert-butyl 2-((4-formyl-2-nitrophenylamino)methyl)pyrrolidine-1-carboxylate (18 g, 51 mmol) and (S)-3,3-dimethylbutan-2-amine (5.2 g, 51 mmol) and 1,2 dichloroethane (400 mL) then stirred at RT for 10 min. Acetic acid (1.6 mL, catalytic amount) and $NaBH(OAc)_3$ (16.37 g, 77 mmol) were added and the reaction mixture stirred at RT for 16 h. The reaction mixture was poured in to saturated $Na_2CO_3$ solution (100 mL) and extracted with $CH_2Cl_2$. The combined organic layers were dried over sodium sulfate and concentrated to afford 22.4 g of (S)-tert-butyl 2-((4-(((S)-3,3-dimethylbutan-2-ylamino)methyl)-2-nitrophenylamino)-methyl)pyrrolidine-1-carboxylate.

Step 3—A 500 mL three neck RB flask was charged with (S)-tert-butyl 2-((4-(((S)-3,3-dimethyl-butan-2-ylamino)methyl)-2-nitrophenylamino)methyl)pyrrolidine-1-carboxylate (22.3 g, 51 mmol) and NaOH (4.5 g, 112 mmol), 1,4-dioxane (200 mL) and water (200 mL) and cooled to 10° C. Benzyl chloroformate (13.1 g, 77 mmol) was added dropwise after which the reaction mixture was stirred at RT for 16 h. The reaction mixture was diluted with ethyl acetate and washed with 1N HCl solution followed by saturated $NaHCO_3$ solution. The organic layer was dried over sodium sulfate and concentrated to yield 22 g of (S)-tert-butyl 2-((4-(((benzyloxycarbonyl)((S)-3,3-dimethylbutan-2-yl)amino)methyl)-2-nitrophenyl-amino)-methyl)pyrrolidine-1-carboxylate.

Step 4—A 500 mL three neck RB flask was charged with (S)-tert-butyl 2-((4-(((benzyloxycarbonyl) ((S)-3,3-dimethylbutan-2-yl)amino)methyl)-2-nitrophenylamino)methyl) pyrrolidine-1-carboxylate (21.9 g, 38 mmol) and methanol (250 mL) followed by addition of zinc dust (12.5 g, 193 mmol) and saturated $NH_4Cl$ solution (10.3 g, 193 mmol). The mixture was heated at 50° C. for 2 h with stirring. The reaction mixture was filtered through a Celite® bed and the bed was washed with methanol. The filtrate was concentrated and partitioned between water and ethyl acetate. The combined organic layer was dried over sodium sulfate and concentrated to give the crude compound which was purified using column purification to yield 20.1 g of (S)-tert-butyl 2-((2-amino-4-(((benzyloxycarbonyl)((S)-3,3-dimethylbutan-2-yl)amino)methyl)phenylamino)-methyl)pyrrolidine-1-carboxylate.

Step 5—A 500 mL three neck RB flask under nitrogen atmosphere was charged with (S)-tert-butyl 2-((2-amino-4-(((benzyloxycarbonyl)((S)-3,3-dimethylbutan-2-yl)amino)methyl)phenylamino)-methyl)-pyrrolidine-1-carboxylate (20 g, 37 mmol) and ethanol (200 mL) then cyanogen bromide (4.7 g, 45 mmol) was added at RT and the mixture was stirred for 4 h. The reaction mixture was concentrated under vacuum and diluted with saturated $NaHCO_3$ solution and extracted with ethyl acetate. The combined organic layer was dried over sodium sulfate and concentrated to give the crude product which was purified using diethyl ether trituration to yield 13.2 g of (S)-tert-butyl 2-((5-(((benzyloxy-carbonyl)((S)-3,3-dimethylbutan-2-yl)amino)methyl)-2-imino-2,3-dihydro-1H-benzo[d]imidazol-1-yl)methyl) pyrrolidine-1-carboxylate.

Intermediate 7

Synthesis of (R)-tert-butyl 2-((2-amino-5-(((tert-butyldimethylsilyl)oxy)methyl)-1H-benzo[d]imida-zol-1-yl)methyl)pyrrolidine-1-carboxylate

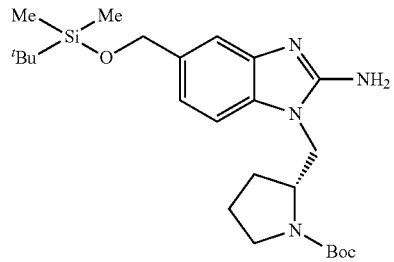 [SMILES: CC(C)(C)OC(=O)N1CCC[C@@H]1Cn1c(N)nc2cc(CO[Si](C)(C)C(C)(C)C)ccc21]

Step 1—A 5 L RB flask under nitrogen atmosphere was charged with 4-fluoro-3-nitrobenzaldehyde (82 g, 483 mmol), DIPEA (249 mL, 1455 mmol) and acetonitrile (1.5 L) at RT. To the resulting solution was added dropwise a solution of tert-butyl(R)-2-(aminomethyl)pyrrolidine-1-carboxylate (106.8 g, 533.4 mmol) in acetonitrile (500 mL) at RT and mixture stirred for 16 h. The reaction mixture was diluted with water (2 L) and extracted with ethyl acetate (3×2 L). The combined organic layer was washed with brine solution (1 L) and concentrated to yield 170 g of tert-butyl (R)-2-(((4-formyl-2-nitrophenyl)amino)methyl)pyrrolidine-1-carboxylate (88.35% yield).

Step 2—A 5 L RB flask under nitrogen atmosphere was charged with a solution of tert-butyl (R)-2-(((4-formyl-2-nitrophenyl)amino)methyl)pyrrolidine-1-carboxylate (170 g, 486 mmol) and THF (2.5 L) at RT and cooled to 0° C. using an ice bath. To the above reaction mixture maintained at 0° C. was added in two portions $NaBH_4$ (9.2 g, 243 mmol). After completion of addition, the ice bath was removed and reaction mixture was warmed to RT and stirred for an additional 5 h. Water (1 L) was added dropwise and resulting aqueous layer was extracted with ethyl acetate. The combined organic layer was washed with brine solution and concentrated to yield 165 g of tert-butyl (R)-2-(((4-(hydroxymethyl)-2-nitrophenyl)amino)-methyl)pyrrolidine-1-carboxylate.

Step 3—A 5 L RB flask was charged with tert-butyl(R)-2-(((4-(hydroxymethyl)-2-nitrophenyl)-amino)methyl)pyrrolidine-1-carboxylate (165 g, 469 mmol) and THF (2 L) at RT then 1H-imidazole (35.16 g, 516.5 mmol) and TBDMS-Cl (77.8 g, 516 mmol) were added and the resulting mixture stirred for 3 h. The reaction mixture was diluted with water and extracted with ethyl acetate. The combined organic layer was concentrated and the crude was purified using flash column chromatography eluting with 20% ethyl acetate in hexanes to yield 130 g of tert-butyl (R)-2-(((4-(((tert-butyldimethylsilyl)oxy)methyl)-2-nitrophenyl)amino)methyl)pyrrolidine-1-carboxylate.

Step 4—A 5 L RB flask was charged with tert-butyl(R)-2-(((4-(((tert-butyldimethylsilyl)oxy)methyl)-2-nitrophenyl)amino)methyl)pyrrolidine-1-carboxylate (140 g, 300 mmol) and 2 L of a 1:1 mixture of methanol: saturated aqueous $NH_4Cl$ was added solution at RT. To the resulting suspension was added portionwise zinc (dust) (97.7 g, 1503 mmol). After stirring 16 h, the reaction mixture was filtered through cotton and extracted with ethyl acetate. The combined organic layer was concentrated. The crude compound which was purified using flash chromatography using 15% ethyl acetate in hexanes to yield 80 g of tert-butyl (R)-2-(((2-amino-4-(((tert-butyldimethylsilyl)oxy)methyl)phenyl)amino)methyl)-pyrrolidine-1-carboxylate.

Step 5—A 5 L RB flask was charged with tert-butyl (R)-2-(((2-amino-4-(((tert-butyldimethyl-silyl)oxy)methyl)phenyl)amino)methyl)pyrrolidine-1-carboxylate (80 g, 183 mmol) and methanol (2 L) and the reaction mixture was cooled to 0° C. Cyanogen bromide (23.34 g, 220.3 mmol) was added to the above reaction mixture at 0° C. After completion of addition, the reaction mixture was warmed to RT and stirred for 2 h. The reaction mixture was diluted with saturated $NaHCO_3$ solution and extracted with ethyl acetate. The combined organic layer was concentrated. The crude product which was purified using flash column chromatography using 50% ethyl acetate in hexanes followed by 5% methanol in $CH_2Cl_2$ to yield 55 g of tert-butyl (R)-2-((5-(((tert-butyldimethylsilyl)oxy)methyl)-2-imino-2,3-dihydro-1H-benzo[d]imidazol-1-yl)methyl)pyrrolidine-1-carboxylate.

Intermediate 8

Synthesis of 5-(oxazol-5-yl)thiophene-2-carboxylic acid

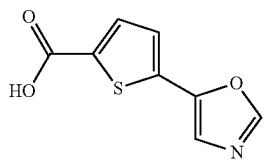 [SMILES: O=C(O)c1ccc(-c2cnco2)s1]

Step 1—A 1 L three neck RB flask was charged with thiophene-2-carboxylic acid (35 g, 273 mmol) and DMF (350 mL) at RT followed by addition of $Na_2CO_3$ (86.8 g, 819.3 mmol) and ethyl iodide (32.8 mL, 409.7 mmol). After completion of addition, the reaction mixture was heated at 70° C. for 3 h. The reaction mixture was cooled to RT and cold water was added to the reaction mixture. The aqueous layer was extracted with EtOAc. The combined organic layer was washed with cold water followed by brine, dried over $Na_2SO_4$ and evaporated to yield 35 g of ethyl thiophene-2-carboxylate which was used as such in next step without further purification.

Step 2—A 1 L three neck RB flask was charged with ethyl thiophene-2-carboxylate (35 g, 223 mmol) and TFA (300 mL) and the reaction mixture was heated at 90° C. To this solution was added portionwise hexamine (62.5 g, 446 mmol and the resulting solution stirred for 16 h. The reaction mixture was poured into solid $Na_2CO_3$ then water waster was added. The reaction mixture was stirred for 1 h and the solid was filtered off and dried to yield 30 g of ethyl 5-formylthiophene-2-carboxylate.

Step 3—A 500 mL three neck RB flask was charged with methyl 5-formylthiophene-2-carboxylate (30 g, 163 mmol) and 1-((isocyanomethyl)sulfonyl)-4-methylbenzene (31.8 g, 163 mmol) then methanol (100 mL) and $K_2CO_3$ (22.5 g, 163 mmol) were added sequentially and the reaction mixture was stirred at 80° C. for 30 min. The reaction mixture was concentrated, diluted with water and extracted with ethyl acetate. The combined organic layer was dried over sodium sulfate, filtered and concentrated. The crude product was purified using flash chromatography eluting with 25% ethyl acetate in hexanes to yield 18 g of methyl 5-(oxazol-5-yl)-thiophene-2-carboxylate.

Step 4—A 500 mL three neck RB flask was charged with methyl 5-(oxazol-5-yl)thiophene-2-carboxylate (18 g, 86 mmol) and dissolved in a mixture of THF:water (360 mL, 1:1) then $LiOH.H_2O$ (4.33 g, 103 mmol) was added and mixture stirred at RT for 2 h. The solvent was removed by distillation and the residue was acidified using 10% HCl solution during which the solid product precipitated and was filtered and dried to yield 12 g of 5-(oxazol-5-yl)thiophene-2-carboxylic acid. LC-MS (ES, m/z): 194 [M−H].

Intermediate 9

5-(2-fluoropyridin-4-yl)thiophene-2-carboxylic acid

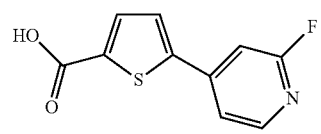 [SMILES: O=C(O)c1ccc(-c2ccnc(F)c2)s1]

5-(2-Fluoropyridin-4-yl)thiophene-2-carboxylic acid (CAS Reg No. 863409-08-09) can be prepared as described by J. M. Bentzien et al., WO2005/079791.

Intermediate 10

5-(2-methyloxazol-5-yl)thiophene-2-carboxylic acid

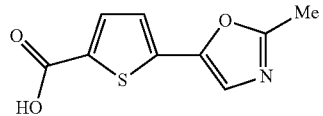 [SMILES: Cc1ncc(-c2ccc(C(=O)O)s2)o1]

5-(2-Methyloxazol-5-yl)thiophene-2-carboxylic acid (CAS Reg. No. 133380-52-6) can be prepared as described by C. J. Goddard, et al., *J. Heterocyclic Chem.* 1991 28(1): 117-28.

Intermediate 11

5-(1H-pyrazol-1-yl)thiophene-2-carboxylic acid

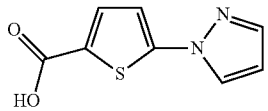 [SMILES: O=C(O)c1ccc(-n2cccn2)s1]

5-(1H-Pyrazol-1-yl)thiophene-2-carboxylic acid (CAS Reg. No. 74990-40-2) can be prepared as described by S. Gromowitz and S. Liljefors, *Chem Scripta* 1979 13(5):157-61.

Intermediate 12

5-(pyrimidin-4-yl)thiophene-2-carboxylic acid

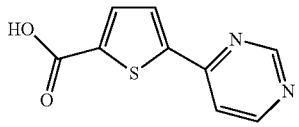 [SMILES: O=C(O)c1ccc(-c2ccncn2)s1]

5-(Pyrimidin-4-yl)thiophene-2-carboxylic acid) (CAS Reg. No. 19084-38-9 can be prepared as described by S. Granowitz and J. Boler, *Arkiv Kemi* 1967 28:157.

Intermediate 13

5-(1,2,4-oxadiazol-2-yl)thiophene-2-carboxylic acid

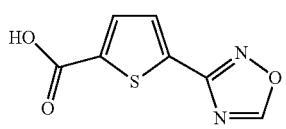 [SMILES: O=C(O)c1ccc(-c2ncon2)s1]

Cyclization of (Z)-5-(N'-hydroxycarbamimidoyl)thiophene-2-carboxylic acid with formic acid will afford methyl 5-(1,3,4-oxadiazol-2-yl)thiophene-2-carboxylate which is saponified with LiOH.H₂O to afford the title compound.

Example 1

Synthesis of (R)-N-(1-((1-(2-cyano-4,4-dimethyl-pent-2-enoyl)pyrrolidin-2-yl)methyl)-5-(hydroxymethyl)-1H-benzo[d]imidazol-2-yl)-5-(oxazol-5-yl)thiophene-2-carboxamide

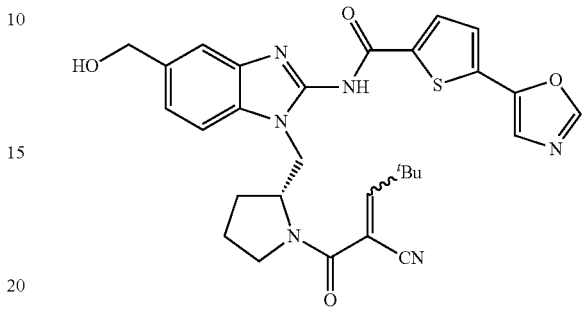

Step 1—To a 250 mL RB three necked flask under nitrogen atmosphere were added at RT tert-butyl (R)-2-((5-(((tert-butyldimethylsilyl)oxy)methyl)-2-imino-2,3-di-hydro-1H-benzo[d]imidazol-1-yl)methyl)pyrrolidine-1-carboxylate (9 g, 19.5 mmol), 5-(oxazol-5-yl)thiophene-2-carboxylic acid (3.81 g, 19.5 mmol) and DMF (90 mL). EDC.HCl (5.61 g, 29.3 mmol) and HOBt (4.49 g, 29.3 mmol) were added and the resulting solution was stirred at RT for 15 minutes. TEA (8.2 mL, 58.6 mmol) was added and the mixture stirred at RT for 16 h. The reaction mixture was poured in to water and the resultant solid was filtered under vacuum. The crude solid was purified using column chromatography eluting with 30% ethyl acetate in hexanes to yield 5.5 g of (R)-tert-butyl 2-((5-(((tert-butyl-dimethylsilyl)oxy)methyl)-2-(5-(oxazol-5-yl)thiophene-2-carboxamido)-1H-benzo[d]imidazol-1-yl)methyl)pyrrolidine-1-carboxylate.

Step 2—To a 250 mL RB three necked flask was added a solution of (R)-tert-butyl 2-((5-(((tert-butyldimethyl-silyl)oxy)methyl)-2-(5-(oxazol-5-yl)thiophene-2-carboxamido)-1H-benzo[d]imidazol-1-yl)-methyl)pyrrolidine-1-carboxylate (5.5 g, 8.6 mmol) and 1,4-dioxane (30 mL). To this reaction was added 6 N HCl in dioxane (30 mL) and the solution was stirring for 16 h. The reaction mixture was concentrated under vacuum and triturated with ethyl acetate to yield 3.9 g of (R)-N-(5-(hydroxymethyl)-1-(pyrrolidin-2-ylmethyl)-1H-benzo[d]imidazol-2-yl)-5-(oxazol-5-yl)thiophene-2-carboxamide hydrochloride.

Step 3—A 100 mL RB three necked flask under nitrogen atmosphere was charged with 2-cyano-4,4-dimethylpent-2-enoic acid (2.4 g, 5.2 mmol) and DMF (24 mL) then cooled to 0° C. HATU (2.98 g, 7.82 mmol) was added and the reaction mixture was stirred for 30 min at 0° C. (R)-N-(5-(hydroxymethyl)-1-(pyrrolidin-2-ylmethyl)-1H-benzo[d]imidazol-2-yl)-5-(oxazol-5-yl)thiophene-2-carboxamide hydrochloride (0.8 g, 5.2 mmol) and DIPEA (2.7 mL, 15.6 mmol) were added sequentially and stirring was continued at RT for 16 h. The reaction mixture was poured in to water and the resultant solid was filtered under vacuum. The crude product was purified by column chromatography eluting with 30% ethyl acetate in hexanes to yield 1.4 g of (R)-N-(1-((1-(2-cyano-4,4-dimethylpent-2-enoyl)pyrrolidin-2-yl)methyl)-5-(hydroxymethyl)-1H-benzo[d]imidazol-2-yl)-5-(oxazol-5-yl)thiophene-2-carboxamide. LC-MS (ES, m/z): 559 [M+H].

Example 2

(R)-N-(1-((1-(2-cyano-4,4-dimethylpent-2-enoyl)pyrrolidin-2-yl)methyl)-5-(((cyclopropyl-methyl)-amino)methyl)-1H-benzo[d]imidazol-2-yl)-5-(oxazol-5-yl)thiophene-2-carboxamide formate

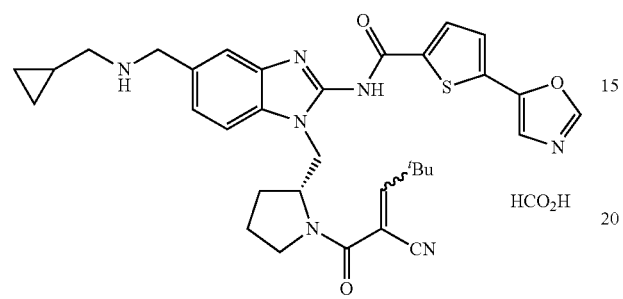

Step 1—To a 100 mL RB single necked flask under nitrogen atmosphere was added a solution of (R)-N-(1-((1-(2-cyano-4,4-dimethylpent-2-enoyl)pyrrolidin-2-yl)methyl)-5-(hydroxymethyl)-1H-benzo[d]imidazol-2-yl)-5-(oxazol-5-yl)thiophene-2-carboxamide (1.4 g, 2.5 mmol) and $CH_2Cl_2$ (28 mL). To the solution cooled to 0° C. was added Dess-Martin periodinane (1.28 g, 3 mmol) then the reaction mixture was warmed to RT and stirred for 1 h. The reaction mixture was diluted with saturated $NaHCO_3$ solution and extracted with $CH_2Cl_2$. The combined organic layer was dried using $Na_2SO_4$ and concentrated. The crude product which was purified by column chromatography eluting with 2% methanol in $CH_2Cl_2$ to yield 1.3 g of (R)-N-(1-((1-(2-cyano-4,4-dimethylpent-2-enoyl)pyrrolidin-2-yl)methyl)-5-formyl-1H-benzo[d]imidazol-2-yl)-5-(oxazol-5-yl)thiophene-2-carboxamide.

Step 2—A 25 mL vial was charged with (R)-N-(1-((1-(2-cyano-4,4-dimethylpent-2-enoyl)pyrrolidin-2-yl)-methyl)-5-formyl-1H-benzo[d]imidazol-2-yl)-5-(oxazol-5-yl)thiophene-2-carboxamide (100 mg, 0.18 mmol), cyclopropylmethanamine (14 mg, 0.2 mmol) and EDC (2 mL) at RT. To this reaction mixture was added acetic acid (1 drop) and the reaction was stirred at RT for 30 min. Sodium triacetoxyborohydride (38 mg, 0.18 mmol) was added and the mixture stirred at RT. After 3 h, an additional equivalent of sodium triacetoxyborohydride (19 mg, 0.09 mmol) was added and the mixture stirred at RT for 1 h. The reaction mixture was diluted with saturated $NaHCO_3$ solution and extracted with $CH_2Cl_2$. The combined organic layer was dried over sodium sulfate and concentrated. The crude product was purified by prep HPLC eluting with 0.1% formic acid in water and acetonitrile to yield 40 mg of (R)-N-(1-((1-(2-cyano-4,4-dimethylpent-2-enoyl)pyrrolidin-2-yl)methyl)-5-(((cyclopropylmethyl)-amino)methyl)-1H-benzo[d]imidazol-2-yl)-5-(oxazol-5-yl)thiophene-2-carboxamide formate. LC-MS (ES, m/z): 612 [M+H].

Example 3

N-(1-(((R)-1-(2-cyano-4,4-dimethylpent-2-enoyl)pyrrolidin-2-yl)methyl)-5-((((S)-1-hydroxy-3,3-dimethylbutan-2-yl)amino)methyl)-1H-benzo[d]imidazol-2-yl)-5-(oxazol-5-yl)thiophene-2-carboxamide formate

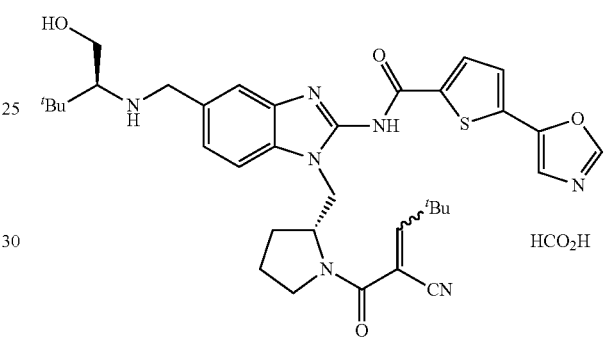

A 25 mL vial was charged with (R)-N-(1-((1-(2-cyano-4,4-dimethylpent-2-enoyl)pyrrolidin-2-yl)-methyl)-5-formyl-1H-benzo[d]imidazol-2-yl)-5-(oxazol-5-yl)thiophene-2-carboxamide (100 mg, 0.18 mmol) and (S)-2-amino-3,3-dimethylbutan-1-ol (23 mg, 0.2 mmol) were dissolved in 1-ethyl-3-(3-dimethylaminopropyl)carbodiimide (EDC, 2 mL) at RT. To this reaction mixture was added acetic acid (2 drop) and the mixture was stirred at RT for 30 min. After 30 min, sodium triacetoxyborohydride (38 mg, 0.18 mmol) was added and the mixture stirred at RT for 3 h. Additional sodium triacetoxyborohydride (19 mg, 0.09 mmol) was added and stirring continued at RT for 1 h. The reaction mixture was diluted with saturated $NaHCO_3$ solution and extracted with $CH_2Cl_2$. The combined organic layer was dried and concentrated. The crude product which was purified by prep HPLC purification eluting with 0.1% formic acid in water and acetonitrile to yield 35 mg of N-((2E)-1-(((R)-1-(2-cyano-4,4-dimethylpent-2-enoyl)pyrrolidin-2-yl)methyl)-5-((((S)-1-hydroxy-3,3-dimethylbutan-2-yl)amino)methyl)-1,3-dihydro-2H-benzo[d]imidazol-2-ylidene)-5-(oxazol-5-yl)thiophene-2-carboxamide as formic acid salt (29.7% yield). LC-MS (ES, m/z): 658 [M+H].

Example 4

N-(1-(((R)-1-(2-cyano-4,4-dimethylpent-2-enoyl)pyrrolidin-2-yl)methyl)-5-((((R)-1-hydroxy-3,3-dimethylbutan-2-yl)amino)methyl)-1H-benzo[d]imidazol-2-yl)-5-(oxazol-5-yl)-thiophene-2-carboxamide formate

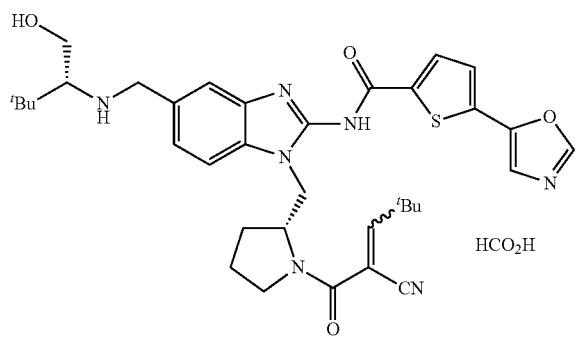 [SMILES: CC(C)(C)C=C(C#N)C(=O)N1CCC[C@@H]1Cn1c(NC(=O)c2ccc(-c3cnco3)s2)nc2cc(CN[C@@H](CO)C(C)(C)C)ccc21 ; "HCO2H"]

Following the procedure in Example 3 but substituting (R)-N-(1-((1-(2-cyano-4,4-dimethylpent-2-enoyl)pyrrolidin-2-yl)methyl)-5-formyl-1H-benzo[d]imidazol-2-yl)-5-(oxazol-5-yl)thiophene-2-carboxamide (100 mg, 0.18 mmol) and (R)-2-amino-3,3-dimethylbutan-1-ol (23 mg, 0.2 mmol) there was obtained 20 mg of N-(1-(((R)-1-(2-cyano-4,4-dimethylpent-2-enoyl)pyrrolidin-2-yl)methyl)-5-((((R)-1-hydroxy-3,3-dimethylbutan-2-yl)amino)methyl)-1H-benzo[d]imidazol-2-yl)-5-(oxazol-5-yl)thiophene-2-carboxamide formate. LC-MS (ES, m/z): 658 [M+H].

Example 5

N-(1-(((R)-1-(2-cyano-4,4-dimethylpent-2-enoyl)pyrrolidin-2-yl)methyl)-5-((((S)-1-hydroxypropan-2-yl)amino)methyl)-1H-benzo[d]imidazol-2-yl)-5-(oxazol-5-yl)-thiophene-2-carboxamide formate

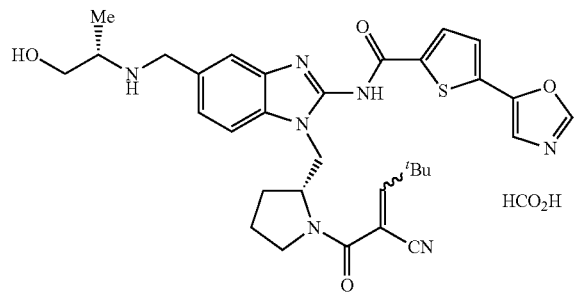

Following the procedure in Example 3 but substituting (R)-N-(1-((1-(2-cyano-4,4-dimethylpent-2-enoyl)pyrrolidin-2-yl)methyl)-5-formyl-1H-benzo[d]imidazol-2-yl)-5-(oxazol-5-yl)thiophene-2-carboxamide and (S)-2-aminopropan-1-ol there was obtained N-(1-(((R)-1-(2-cyano-4,4-dimethylpent-2-enoyl)pyrrolidin-2-yl)methyl)-5-((((S)-1-hydroxypropan-2-yl)amino)methyl)-1H-benzo[d]imidazol-2-yl)-5-(oxazol-5-yl)thiophene-2-carboxamide formate. LC-MS (ES, m/z): 616 [M+H].

Example 6

N-(1-(((R)-1-(2-cyano-4,4-dimethylpent-2-enoyl)pyrrolidin-2-yl)methyl)-5-((((R)-1-hydroxypropan-2-yl)amino)methyl)-1H-benzo[d]imidazol-2-yl)-5-(oxazol-5-yl)-thiophene-2-carboxamide formate

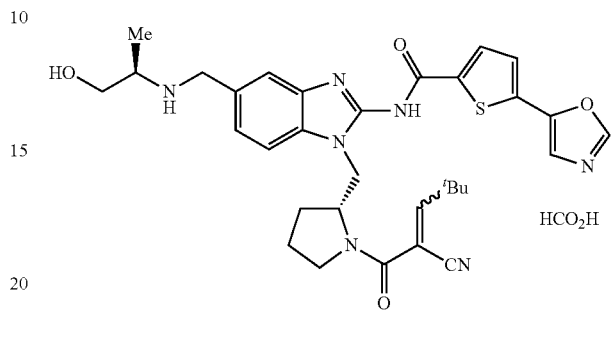

Following the procedure in Example 3 but substituting (R)-N-(1-((1-(2-cyano-4,4-dimethylpent-2-enoyl)pyrrolidin-2-yl)methyl)-5-formyl-1H-benzo[d]imidazol-2-yl)-5-(oxazol-5-yl)thiophene-2-carboxamide and (R)-2-aminopropan-1-ol there was obtained N-(1-(((R)-1-(2-cyano-4,4-dimethylpent-2-enoyl)pyrrolidin-2-yl)methyl)-5-((((R)-1-hydroxypropan-2-yl)amino)methyl)-1H-benzo[d]imidazol-2-yl)-5-(oxazol-5-yl)thiophene-2-carb oxamide formate. LC-MS (ES, m/z): 616 [M+H].

Example 7

N-1-(((R)-1-(2-cyano-4,4-dimethylpent-2-enoyl)pyrrolidin-2-yl)methyl)-5-((((R)-1-methoxypropan-2-yl)amino)methyl)-1H-benzo[d]imidazol-2-yl)-5-(oxazol-5-yl)-thiophene-2-carboxamide formate

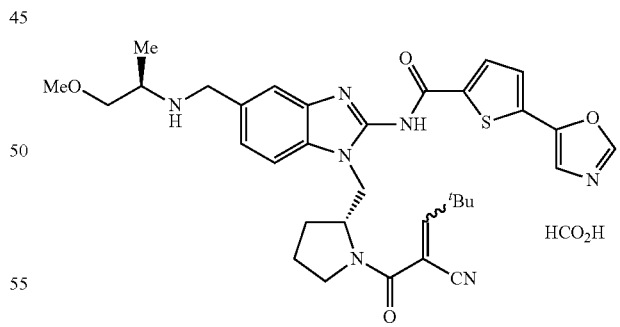

Following the procedure in Example 3 but substituting (R)-N-(1-((1-(2-cyano-4,4-dimethylpent-2-enoyl)pyrrolidin-2-yl)methyl)-5-formyl-1H-benzo[d]imidazol-2-yl)-5-(oxazol-5-yl)thiophene-2-carboxamide and (R)-1-methoxypropan-2-amine there was obtained N-(1-(((R)-1-(2-cyano-4,4-dimethylpent-2-enoyl)pyrrolidin-2-yl)methyl)-5-((((R)-1-methoxypropan-2-yl)amino)methyl)-1H-benzo[d]imidazol-2-yl)-5-(oxazol-5-yl)thiophene-2-carboxamide formate. LC-MS (ES, m/z): 630 [M+H].

Example 8

N-(1-(((R)-1-(2-cyano-4,4-dimethylpent-2-enoyl)pyrrolidin-2-yl)methyl)-5-((((S)-1-methoxypropan-2-yl)amino)methyl)-1H-benzo[d]imidazol-2-yl)-5-(oxazol-5-yl)-thiophene-2-carboxamide formate

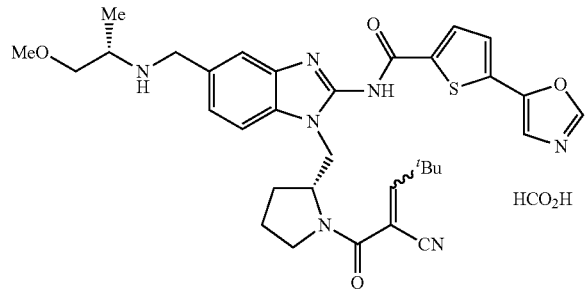 [SMILES: COC[C@H](C)NCc1ccc2c(c1)nc(NC(=O)c1ccc(-c3cnco3)s1)n2C[C@H]1CCCN1C(=O)C(C#N)=CC(C)(C)C ; "HCO2H"]

Following the procedure in Example 3 but substituting (R)-N-(1-((1-(2-cyano-4,4-dimethylpent-2-enoyl)pyrrolidin-2-yl)methyl)-5-formyl-1H-benzo[d]imidazol-2-yl)-5-(oxazol-5-yl)thiophene-2-carboxamide and (S)-1-methoxypropan-2-amine there was obtained N-(1-(((R)-1-(2-cyano-4,4-dimethylpent-2-enoyl)pyrrolidin-2-yl)methyl)-5-((((S)-1-methoxypropan-2-yl)amino)methyl)-1H-benzo[d]imidazol-2-yl)-5-(oxazol-5-yl)thiophene-2-carboxamide formate. LC-MS (ES, m/z): 630 [M+H].

Example 9

(R)-N-(1-((1-acryloylpyrrolidin-2-yl)methyl)-5-(((cyclopropylmethyl)amino)methyl)-1H-benzo[d]imidazol-2-yl)-5-(oxazol-5-yl)thiophene-2-carboxamide

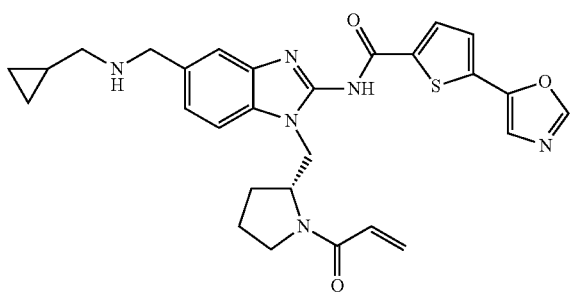 [SMILES: C=CC(=O)N1CCC[C@@H]1Cn1c(NC(=O)c2ccc(-c3cnco3)s2)nc2cc(CNCC3CC3)ccc21]

Step 1—To a 100 mL RB flask under nitrogen atmosphere was added (R)-N-(5-(hydroxy-methyl)-1-(pyrrolidin-2-ylmethyl)-1H-benzo[d]imidazol-2-yl)-5-(oxazol-5-yl)thiophene-2-carboxamide hydrochloride (3.7 g, 8.04 mmol) and THF (40 mL) and resulting suspension cooled to 0° C. To this reaction mixture, acryloyl chloride (50% in toluene) (1.45 g, 8.04 mmol) was added dropwise at 0° C. and the mixture stirred at 0° C. for 30 min. The reaction mixture was diluted with saturated NaHCO$_3$ solution and stirred for 30 min at RT and the resultant solid was filtered and dried to yield 3.5 g of (R)-N-(1-((1-acryloylpyrrolidin-2-yl)methyl)-5-(hydroxymethyl)-1H-benzo[d]imidazol-2-yl)-5-(oxazol-5-yl)thiophene-2-carboxamide.

Step 2—To a 100 mL RB flask under nitrogen atmosphere was added (R)-N-(1-((1-acryloyl-pyrrolidin-2-yl)methyl)-5-(hydroxymethyl)-1H-benzo[d]imidazol-2-yl)-5-(oxazol-5-yl)-thiophene-2-carboxamide (3.5 g, 7.3 mmol) and CH$_2$Cl$_2$ (50 mL) and the resulting suspension was cooled to 0° C. Dess-Martin periodinane (3.73 g, 8.83 mmol) was added and the reaction mixture was warmed to RT and stirred for 1 h. The reaction mixture was diluted with saturated NaHCO$_3$ solution and extracted with CH$_2$Cl$_2$. The combined organic layer was concentrated and the crude product purified using flash column chromatography eluting with 5% methanol in CH$_2$Cl$_2$ to yield 2.5 g of (R)-N-(1-(((1-acryloylpyrrolidin-2-yl)methyl)-5-formyl-1H-benzo[d]-imidazol-2-yl)-5-(oxazol-5-yl)thiophene-2-carboxamide.

Step 3—A 10 mL vial under nitrogen atmosphere was charged with (R)-N-(1-((1-acryloylpyrrolidin-2-yl)methyl)-5-formyl-1H-benzo[d]imidazol-2-yl)-5-(oxazol-5-yl)thiophene-2-carboxamide (180 mg, 0.38 mmol), cyclopropylmethanamine (53.8 mg, 0.76 mmol) and a 1:1 mixture of dichloroethane and MeOH and the mixture stirred at RT for 45 min. NaBH(OAc)$_3$ (120.8 mg, 0.57 mmol) and acetic acid (1 drop) were added and the mixture stirred at RT for 3 h. The reaction mixture was diluted with saturated NaHCO$_3$ solution and extracted using CH$_2$Cl$_2$. The combined organic layer was dried over sodium sulfate and concentrated under vacuum. The crude product was purified by chromatography using 5-10% MeOH in CH$_2$Cl$_2$ to yield 26 mg of (R)-N-(1-((1-acryloyl-pyrrolidin-2-yl)methyl)-5-(((cyclopropylmethyl)amino)methyl)-1H-benzo[d]imidazol-2-yl)-5-(oxazol-5-yl)thiophene-2-carboxamide. LC-MS (ES, m/z): 531 [M+H].

Example 10

N-(1-(((R)-1-acryloylpyrrolidin-2-yl)methyl)-5-(((((S)-1-hydroxy-3,3-dimethylbutan-2-yl)-amino)methyl)-1H-benzo[d]imidazol-2-yl)-5-(oxazol-5-yl)thiophene-2-carboxamide

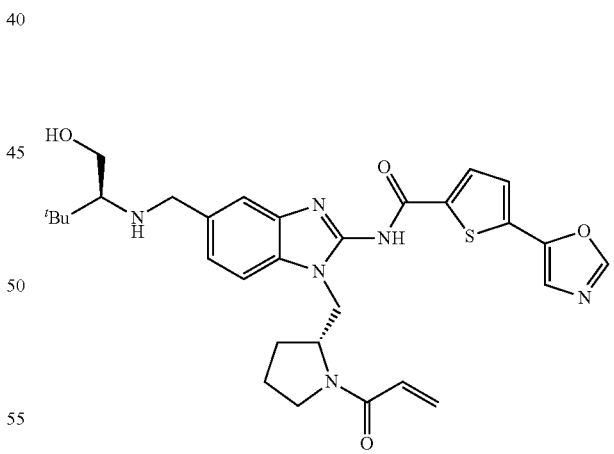

Following the procedure in step 3 of Example 9 but replacing cyclopropylmethanamine with (S)-2-amino-3,3-dimethylbutan-1-ol afforded N-(1-(((R)-1-acryloylpyrrolidin-2-yl)methyl)-5-(((((S)-1-hydroxy-3,3-dimethylbutan-2-yl)amino)methyl)-1H-benzo[d]imidazol-2-yl)-5-(oxazol-5-yl)thiophene-2-carboxamide. LC-MS (ES, m/z): 577 [M+H].

Example 11

N-(1-(((R)-1-acryloylpyrrolidin-2-yl)methyl)-5-((((R)-1-hydroxy-3,3-dimethylbutan-2-yl)-amino)-methyl)-1H-benzo[d]imidazol-2-yl)-5-(oxazol-5-yl)thiophene-2-carboxamide

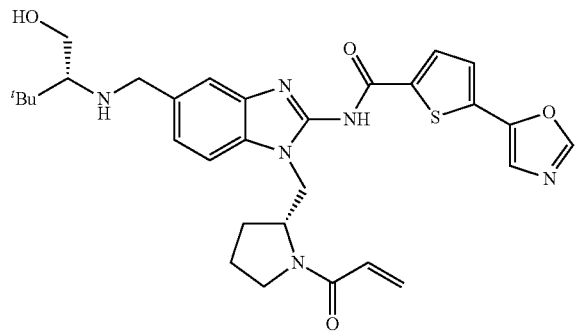 [SMILES: C=CC(=O)N1CCC[C@@H]1Cn1c(NC(=O)c2ccc(-c3cnco3)s2)nc2cc(CN[C@@H](CO)C(C)(C)C)ccc21]

Following the procedure in step 3 of Example 9 but replacing but replacing cyclopropyl-methanamine with (R)-2-amino-3,3-dimethylbutan-1-ol afforded N-(1-(((R)-1-acryloyl-pyrrolidin-2-yl)methyl)-5-((((R)-1-hydroxy-3,3-dimethylbutan-2-yl)amino)methyl)-1H-benzo[d]imidazol-2-yl)-5-(oxazol-5-yl)thiophene-2-carboxamide. LC-MS (ES, m/z): 577 [M+H].

Example 12

N-(1-(((R)-1-acryloylpyrrolidin-2-yl)methyl)-5-((((S)-1-hydroxypropan-2-yl)amino)methyl)-1H-benzo[d]imidazol-2-yl)-5-(oxazol-5-yl)thiophene-2-carboxamide

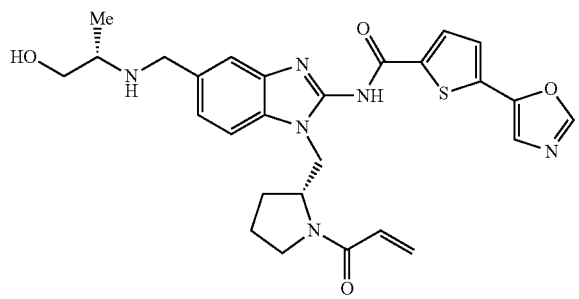 [SMILES: C=CC(=O)N1CCC[C@@H]1Cn1c(NC(=O)c2ccc(-c3cnco3)s2)nc2cc(CN[C@@H](C)CO)ccc21]

Following the procedure in Example 9, step 3, but replacing cyclopropylmethanamine with (S)-2-aminopropan-1-ol afforded N-(1-(((R)-1-acryloylpyrrolidin-2-yl)methyl)-5-((((S)-1-hydroxypropan-2-yl)amino)methyl)-1H-benzo[d]imidazol-2-yl)-5-(oxazol-5-yl)thiophene-2-carboxamide. LC-MS (ES, m/z): 535 [M+H].

Example 13

N-(1-(((R)-1-acryloylpyrrolidin-2-yl)methyl)-5-((((R)-1-hydroxypropan-2-yl)amino)methyl)-1H-benzo[d]imidazol-2-yl)-5-(oxazol-5-yl)thiophene-2-carboxamide

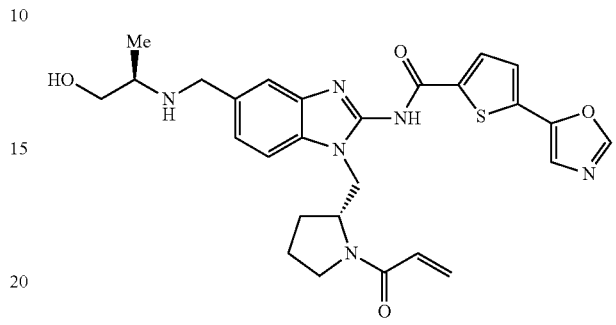

Following the procedure in Example 9, step 3, but replacing cyclopropylmethanamine with (R)-2-aminopropan-1-ol afforded N-(1-(((R)-1-acryloylpyrrolidin-2-yl)methyl)-5-((((R)-1-hydroxypropan-2-yl)amino)methyl)-1H-benzo[d]imidazol-2-yl)-5-(oxazol-5-yl)thiophene-2-carboxamide. LC-MS (ES, m/z): 535 [M+H].

Example 14

(R)-N-(1-((1-acryloylpyrrolidin-2-yl)methyl)-5-(((2-hydroxy-2-methylpropyl)amino)methyl)-1H-benzo[d]imidazol-2-yl)-5-(oxazol-5-yl)thiophene-2-carboxamide

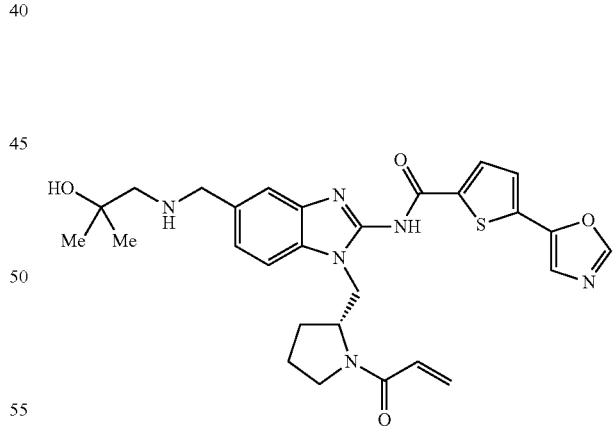

Following the procedure in Example 9, step 3, but replacing cyclopropylmethanamine with 1-amino-2-methylpropan-2-ol afforded (R)-N-(1-((1-acryloylpyrrolidin-2-yl)methyl)-5-(((2-hydroxy-2-methylpropyl)amino)methyl)-1H-benzo[d]imidazol-2-yl)-5-(oxazol-5-yl)thiophene-2-carboxamide. LC-MS (ES, m/z): 535 [M+H].

Example 15

N-(1-(((R)-1-(2-cyano-4,4-dimethylpent-2-enoyl)pyrrolidin-2-yl)methyl)-5-((((S)-3,3-dimethyl-butan-2-yl)amino)methyl)-1H-benzo[d]imidazol-2-yl)-5-(oxazol-5-yl)thiophene-2-carboxamide

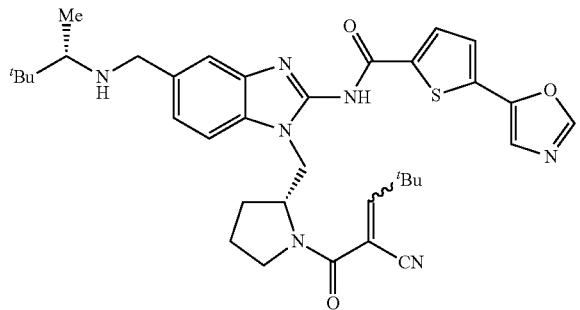 [SMILES: C[C@H](NCc1ccc2c(c1)nc(NC(=O)c1ccc(-c3cnco3)s1)n2C[C@H]1CCCN1C(=O)C(C#N)=CC(C)(C)C)C(C)(C)C]

To a 50 mL single neck RB flask was added a solution of (R)-N-(1-((1-(2-cyano-4,4-dimethylpent-2-enoyl)pyrrolidin-2-yl)methyl)-5-formyl-1H-benzo[d]imidazol-2-yl)-5-(oxazol-5-yl)thiophene-2-carboxamide (700 mg, 1.26 mmol) and (S)-3,3-dimethylbutan-2-amine (190 mg, 1.89 mmol) in dichloroethane (14 mL) at RT. To this reaction mixture at RT was added acetic acid (0.2 mL) and the mixture stirred at RT for 30 min. Sodium triacetoxyborohydride (400 mg, 1.89 mmol) was added and the mixture stirred at RT for 2 h. Additional sodium triacetoxyborohydride (266 mg, 1.26 mmol) was added and stirring continued for 2 h. The reaction mixture was then diluted with saturated NaHCO$_3$ solution and extracted with CH$_2$Cl$_2$. The combined organic layer was dried over sodium sulfate and concentrated. The crude product which was purified by column chromatography eluting with 4% methanol in CH$_2$Cl$_2$ to yield 325 mg of N-(1-(((R)-1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)-5-(oxazol-5-yl)thiophene-2-carboxamide. LC-MS (ES, m/z): 642 [M+H].

Biological Example 1

Inhibition of ITK and RLK Enzymatic Activity . . . In Vitro Assays

The ability of the compounds of the present disclosure to inhibit ITK was measured using the Caliper assay format, which is an electrophoretic separation of a phosphorylated peptide substrate from unphosphorylated peptide. The enzymatic reaction occurred in a buffer of 100 mM HEPES pH 7.5, 5 mM MgCl$_2$, 0.01% Triton-X 100, 0.1% Bovine Serum Albumin, and 1% DMSO. Three-fold dilutions of compounds were prepared in DMSO. Compounds were added to enzyme and pre-incubated for 15 minutes prior to reaction. The enzymatic reaction was initiated by addition of phospho-acceptor peptide FAM-GEEPLYWSFPAKKK-NH$_2$ (also known as SRCtide) to 1 µM and ATP to its Km value (ITK: 10 µM). The reaction proceeded for 6 hours and was terminated by addition of EDTA. The assay employed an enzyme concentration of 0.2 nM. The top compound concentration was 5 µM. The amount of phosphorylated substrate was determined by the Caliper instrumentation, and dose-response curves were fit using standard methods to determine the IC$_{50}$ values. The IC$_{50}$ for a representative compound of the present disclosure is provided in Table 1 below.

The ability of the compounds of the present disclosure to inhibit RLK was also measured using the Caliper assay format. The enzymatic reaction occurred in a buffer of 100 mM HEPES pH 7.5, 5 mM MgCl$_2$, 0.01% Triton-X 100, 0.1% Bovine Serum Albumin, and 1% DMSO. Three-fold dilutions of compounds were prepared in DMSO. Compounds were added to enzyme and pre-incubated for 15 minutes prior to reaction. The enzymatic reaction was initiated by addition of phospho-acceptor peptide FAM-EAI-YAAPFAKKK-CONH$_2$ to 1 µM and ATP to its Km value (RLK: 100 µM). The reaction proceeded for 3 hours and was terminated by addition of EDTA. The assay employed an enzyme concentration of 0.83 nM. The top compound concentration was 5 µM. The amount of phosphorylated substrate was determined by the Caliper instrumentation, and dose-response curves were fit using standard methods to determine the IC$_{50}$ values. The IC$_{50}$ for a representative compound of the present disclosure is provided in Table 1 below.

TABLE 1

| Cpd #* | ITK IC$_{50}$ nm | RLK IC$_{50}$ nm |
|---|---|---|
| 1 | 1.4 | 1.2 |
| 2 | 1.1 | 3.5 |
| 3 | 0.8 | 1.5 |
| 4 | 0.6 | 0.9 |
| 5 | 0.8 | 0.9 |
| 6 | 0.9 | 1.3 |
| 7 | 0.8 | 2.1 |
| 9 | 0.08 | 0.3 |
| 10 | 0.05 | 0.2 |
| 11 | 0.1 | 0.5 |
| 12 | 0.04 | 0.3 |
| 13 | 0.09 | 0.3 |
| 14 | 0.09 | 0.3 |
| 15 | 0.3 | 1.2 |

*see Cpd Table 1 above

Biological Example 2

Determination of Drug-Kinase Residence Time

The following are protocols to distinguish whether a compound displays a slow or non-existent dissociation rate from ITK and RLK, such as typically would occur if a covalent bond is formed between the compound and the target. The read-out for slow dissociation is the extent that the compound of interest can block binding of an excess amount of a high affinity fluorescent tracer molecule to the kinase active site, as detected using time-resolved fluorescence resonance energy transfer (TR-FRET).

The experiment is conducted in a buffer consisting of 50 mM Hepes pH 7.5, 10 mM MgCl$_2$, 0.01% Triton X-100, and 1 mM EGTA. For ITK experiments, 500 nM ITK (Invitrogen Cat. #PV3875) is incubated with 1.5 uM of test compound for 90 minutes in a volume of 10 µL. The mixture is then diluted 50-fold by addition of 4 µL sample to 196 µL of buffer. A 10 µL volume of the diluted kinase/test compound solution is then added to a well of a small volume 384 well plate (such as Greiner Cat. #784076). In order to probe for reversibility of the kinase-compound binding interaction, a competition solution containing both a high affinity fluorescent tracer and an antibody coupled to Europium is prepared. The competition solution contains 5 µM Tracer 236 (Invitrogen Cat. #PV5592), which is a proprietary high affinity ligand for ITK coupled to the fluorophore AlexaFluor 647. The competition solution also contains 12.5 nM of an Anti-His antibody coupled to Europium (Perkin Elmer Cat. AD0205) which is designed to bind the His purification tag in ITK. After addition of 10 µL of the competition solution to the Greiner plate, the mixture is incubated for various times to allow time for dissociation of non-covalent inhibitors and binding of the high affinity tracer. It is expected that slow dissociating inhibitors will block binding of the tracer while rapidly dissociating inhibitors will not. Binding of the tracer to ITK is detected using TR-FRET between the Europium moiety of the Anti-His antibody and the AlexaFluor 647 group of Tracer 236. Binding is evaluated using a Perkin Elmer Envision instrument (Model 2101) equipped with filters and mirrors compatible with LANCE-type TR-FRET experiments. The excitation wavelength is 337 nm and the emission wavelengths are 620 nm and 665 nm. Data is acquired as the ratio of emission at 665 nm to 620 nm and is plotted as the percentage of signal obtained in the absence of competitor compound. The background signal is obtained by omission of kinase from the reaction.

For RLK experiments, 500 nM RLK (Millipore Cat. 14-761) is incubated with 1.5 µM of test compound for 30 minutes in a volume of 10 µL. The mixture is then diluted 5-fold by addition of 10 µL sample to 40 µL of buffer. A 10 µL volume of the diluted kinase/test compound solution is then added to a well of a small volume 384 well plate (such as Greiner Cat. #784076). In order to probe for reversibility of the kinase-compound binding interaction, a competition solution containing both a high affinity fluorescent tracer and an antibody coupled to Europium is prepared.

The competition solution contains 5 µM Tracer 178 (Invitrogen Cat. #PV5593), which is a proprietary high affinity ligand for RLKcoupled to the fluorophore AlexaFluor 647. The competition solution also contains 12.5 nM of an Anti-His antibody coupled to Europium (Perkin Elmer Cat. AD0205) which is designed to bind the His purification tag in ITK. After addition of 10 µL of the competition solution to the Greiner plate, the mixture is incubated for various times to allow time for dissociation of non-covalent inhibitors and binding of the high affinity tracer. Binding is evaluated as described above for ITK using a Perkin Elmer Envision instrument (Model 2101) equipped with filters and mirrors compatible with LANCE-type TR-FRET experiments.

In each of the above experiment, when the compound is an irreversible covalent inhibitor, tracer is completely blocked from binding to the target throughout the entire course of the experiment. When the compound is a reversible covalent inhibitor, the tracer binds to the target as the compound dissociated from the target. The data is evaluated as occupancy of the target at 1, 6 and 24 hours after initiation of dissociation.

Biological Example 3

Cellular Potency Measured T Cell Receptor (TCR)-Induced Activation of Jurkat Cells Cellular potencies of compounds of Formula (I) were measured by blockade of activation of the transcription factor Nuclear Factor in Activated T cells (NFAT) following stimulation of the T cell receptor. Activation was measured using the Cell Sensor cell line NFAT-bla Jurkat from Invitrogen (Madison, Wis.) that utilizes a reporter construct for NFAT activation. Tripling dilutions of inhibitors were preincubated with Jurkat T cells for 1 hour followed by activation with predetermined IC80 concentrations of anti-CD3 and anti-CD28 for 5 hours. The NFAT reporter activity was then assessed by addition of the beta-lactamase substrate followed by incubation for an additional 2 hours. Substrate cleavage was then measured by monitoring the change in fluorescence resonance energy transfer using appropriate excitation and emission wavelength filters. The percent inhibition was then plotted as a function of the log of the compound concentration to calculate an IC50 using standard curve-fitting software. Data for representative compounds are shown in Table 2 below.

TABLE 2

| Compound #* | TCR-induced NFAT (µM) |
|---|---|
| 1 | 0.050 |
| 2 | 0.536 |
| 7 | 0.101 |
| 9 | 0.004 |
| 12 | 0.005 |

*see Cpd Table 1 above

Biological Example 4

Inhibition of IL-2 Production in Anti-CD3 and Anti-CD28 Stimulated Human PBMCs

Peripheral blood mononuclear cells (PBMCs) isolated from human whole blood were preincubated with or without compound of Formula (I) in RPMI 1640+10% fetal bovine serum at 37° C. for 30 min. PBMCs were stimulated with 2.5 µg/mL plate bound anti-CD3 and 1 µg/mL soluble anti-CD28 overnight and supernatant was collected for AlphaLISA IL2 assay. The IL-2 production was measured as AlphaLISA signal counts using Envision plate reader. Human Blood was obtained from healthy volunteer through Stanford Blood Center. Blood was collected by venipuncture into sodium heparin tubes. Blood was layered over Ficoll-Histopaque in 50 mL conical tube and centrifuged at 2000 rpm for 20 minutes at RT. Mononuclear cells were collected into 50 mL conical tubes, pooled and diluted with 1×PBS to make up final volume to 50 mL in each tube. Cells were pelleted at 1500 rpm for 5 minutes and cells are washed two times. The cells were counted in Vi-Cell using trypan blue to determine cell number and viability. PBMCs were then resuspended in RPMI 1640 with 10% fetal bovine serum at a concentration 1×106 cells/mL.

A 96-well polystyrene plate was coated with 2.5 µg/mL anti-CD3 in PBS overnight at 4° C. The wells in column one were coated with PBS only for unstimulated controls. Compounds of the disclosure were dissolved at 10 mM in 100% DMSO and 1:3 serial dilutions of compounds are prepared in DMSO. These compounds were further diluted in complete medium to make final DMSO 0.2% in 96-well polypropylene plate. To treat PBMC with compounds, 100 µL of 1×10$^5$ cells were cultured in 96-well polypropylene plate. Then 8 µL of each diluted compound was added in the corresponding wells in duplicate and 8 µL of medium with 2.5% DMSO was added to control wells. The plates were incubated at 37° C. incubator for 30 min. The anti-CD3 coated plates were washed with PBS twice. 92 µL of media containing 1 µg/mL anti-CD28 were added to all wells except unstimulated controls. In unstimulated wells, 92 ul medium was added. Plates were incubated overnight at 37° C., 5% $CO_2$ incubator.

The next day, 150 µL of supernatant was removed from each well for AlphaLISA IL2 assay. According to manufacturer's protocol, 1× buffer, IL2 standards (10 conc), 2.5× acceptor plus biotinylated beads mixture, 2× streptavidin donor beads were prepared. To each well, 2.5 µL standards or samples are added and then 10 µL of 2.5× mixture beads were added to each well. The plate was sealed with aluminum plate sealer and incubated at room temp on shaker for 1 hr. 12.5 µL of streptavidin donor beads are added to each well in dark room. The plate was sealed with aluminum plate sealer and incubated at room temp on shaker for 30 min. The plate was read in an Envision plate reader.

The $IC_{50}$ for each compound was determined from a ten-point dose response curve for all compounds, each dose being tested in duplicate wells. The $IC_{50}$ represents the concentration of a compound that shows 50% inhibition of IL-2 production in response to anti-CD3+anti-CD28 stimulated PBMCs with compound to 50% of that in control wells without compounds, and was calculated using curve fitting software.

Data for representative compounds are shown in Table 3 below.

TABLE 3

| Compound #* | CD3/CD28-induced IL-2 (µM) |
|---|---|
| 1 | 0.071 |
| 2 | 0.081 |
| 7 | 0.109 |
| 9 | 0.004 |
| 12 | 0.004 |

*see Cpd Table 1 above

Biological Example 5

Delayed Type Hypersensitivity in Mice

Delayed type hypersensitivity is a standard model for measuring T cell mediated skin inflammation in vivo. Previous studies suggest that an inhibitor of ITK should be efficacious in such a model (see von Bonin et al. Inhibition of the IL-2-inducible tyrosine kinase (ITK) activity: a new concept for the therapy of inflammatory skin diseases, *Exp Dermatol*, 20:41-47, 2010). Starting on study day zero (0), mice were randomized by body weight (using MS Excel) in to treatment groups, sensitized with aliquots of 150 µL of a 5% oxazolone (Sigma) solution (3 parts ethanol+1 part acetone) epicutaneously on their shaved abdomens. The right ears of the same (Isoflurane anesthetized) mice were challenged with 3% oxazolone solution 7 days later (Day 7), (i.e., 10 µL on the front and another 10 µL on the back of the right ears; whereas the left ears were painted on both ears with the ethanol/acetone mixture. One hour prior to challenge, certain groups received an ITK inhibitor at a dose and route determined to be appropriate based on previous pharmacodynamic studies. Twenty-four hours later, animals were sacrificed via cervical dislocation and then, a 7-mm disc of ear (by using a cork borer, from Fisher Scientific) was punched out and weighed since weight is proportional to edema. Compound of the disclosure was active in this model.

Biological Example 6

Mass Spectral Analysis

A protein kinase that is inhibited by compound of Formula (I) may be subjected to mass spectral analysis to assess whether the compounds of Formula (I) form permanent, irreversible covalent adducts or reversible covalent bond. Suitable analytical methods to examine intact full protein or peptide fragments generated upon tryptic cleavage of the protein kinase are generally known in the art (see Lipton, Mary S., Ljiljana, Pasa-Tolic, Eds. Mass Spectrometry of Proteins and Peptides, Methods and Protocols, Second Edition. Humana Press. 2009). Such methods identify permanent, irreversible covalent protein adducts by observing a mass peak that corresponds to the mass of a control sample plus the mass of an irreversible adduct. Two such methods are described below.

Method A: Mass Spectral Analysis of Intact Full Kinase

A protein kinase (5 µM) is incubated with a compound of Formula (I) (25-100 µM, 5-20 equiv) for 1 h at RT in buffer (20 mM Hepes [pH 8.0], 100 mM NaCl, 10 mM $MgCl_2$). A control sample is also prepared which does not have a compound of Formula (I). The reaction is stopped by adding an equal volume of 0.4% formic acid, and the samples are analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of the protein kinase and any adducts may be determined with MassLynx deconvolution software (see patent application WO2014 011900, and PCT/US2010/048916).

Results: High-resolution intact mass spectrometry analysis of a kinase that is inhibited by a compound of Formula (I) where $R^b$ is cyano will reveal a spectrum similar to the kinase in the absence of inhibitor (e.g. control sample). There will be no formation of a new peak in the mass spectrum corresponding to the molecular mass of the kinase plus the molecular mass of the compound of Formula (I). On the basis of this experiment no permanent, irreversible protein adduct will be apparent to one skilled in the art. Compounds of Formula (I) where $R^b$ is hydrogen will show a new peak in the mass spectrum corresponding to the molecular mass of the kinase plus the molecular mass of the compound of Formula (I) respectively, indicating a permanent, irreversible covalent bond formation between the protein and the compound of Formula (I) respectively.

Method B: Mass Spectral Analysis of Kinase Tryptic Digest

A protein (10-100 pmols) is incubated with the compound (I) (100-1000 pmols, 10 equiv) for 3 h prior to tryptic digestion. Iodoacetamide may be used as the alkylating agent after compound incubation. A control sample is also prepared which does not have the addition of the compound (I). For tryptic digests a 1 µL aliquot (3.3 pmols) is diluted with 10 µL of 0.1% TFA prior to micro C18 Zip Tipping directly onto the MALDI target using alpha cyano-4-hydroxycinnamic acid as the desorption matrix (5 mg/mol in 0.1% TFA:Acetonitrile 50:50) or sinapinic acid as the desorption matrix (10 mg/mol in 0.1% TFA:Acetonitrile 50:50). (see PCT/US2010/048916)

Results: High-resolution mass spectrometry analysis of the tryptic fragments of a kinase that is inhibited by an irreversible kinase inhibitor will reveal a spectrum that contains modified peptides that are not present in the control sample. On the basis of this experiment, irreversible protein adducts will be apparent to one skilled in the art. Furthermore, on the basis of the exact mass and MS-MS fragmentation pattern, the sequence of the modified peptide may be ascertained, there by unambiguously defining the exact cysteine residue that is the site of covalent modification.

Biological Example 7

Recovery of Kinase Activity Upon Dialysis

Standard experimental methods to establish reversibility are known in the art. Protein dialysis is one such method. A solution containing a protein kinase that is inhibited by a compound of Formula (I) may be subjected to extensive dialysis to establish if the kinase inhibitor is reversible. Partial or complete recovery of protein kinase activity over time during dialysis is indicative of reversibility.
Method:
A compound of Formula (I) and/or pharmaceutically acceptable salt described herein (1 µM) is added to a solution of protein kinase (50 nM, pre-activated if necessary) in a buffer containing 20 mM Hepes [pH 8.0], 10 mM $MgCl_2$, 2.5 mM tris(2-carboxyethyl)phosphine (TCEP), 0.25 mg/mL BSA, and 100 µM ATP. After 60 min at RT, the reactions is transferred to a dialysis cassette (0.1-0.5 mL Slide-A-Lyzer, MWCO 10 kDa, Pierce) and dialyzed against 2 L of buffer (20 mM Hepes [pH 8.0], 10 mM $MgCl_2$, 1 mM DTT) at 4° C. The dialysis buffer is exchanged after 2 h, and then is exchanged every 24 h until the end of the experiment. Aliquots are removed from the dialysis cassettes every 24 h, flash frozen in liquid nitrogen, and subsequently analyzed for protein kinase activity in triplicate. Kinase activity for each sample is normalized to the DMSO control for that time point and expressed as the mean±SD.

Results: Kinase activity recovers from inhibition by reversible kinase inhibitors upon dialysis. Upon extensive dialysis at 4° C. or at RT, kinase activity partially or completely recovers in a time-dependent manner from inhibition by an excess (20 equiv, 1.0 µM) of reversible kinase inhibitor. Kinase activity does not recover from inhibition by irreversible covalent kinase inhibitors upon dialysis.

Biological Example 8

Reversibility of Binding

The following approach can be used to differentiate compounds that form irreversible bonds with their targets, such as acrylamide compounds, from compound that bind reversibly such as a reversible covalent inhibitor. Reactions are prepared with the protein target at a higher concentration than the compounds of interest. Both irreversible and reversible compounds bind the target and became depleted from solution. The reactions are then treated with perturbations including both denaturation with 5 M guanidine hydrochloride and digestion with trypsin, disrupting proper folding of the target. It will be found that the perturbation returns reversible compounds to solution due to dissociation from the target while irreversible compounds remain bound to the target. The concentration of compound in solution is assessed both preceding and following perturbation using high performance liquid chromatography (HPLC) coupled to tandem mass spectrometry. Using this technique, it can be demonstrated that an acrylamide-containing compound i.e. compounds of Formula (I) where $R^b$ is hydrogen is depleted from solution in both the native and perturbed state, while reversible compounds of Formula (I) where $R^b$ is cyano depletes in the folded state but returns to solution following perturbation of the target.

Biological Example 9

Effects on Differentiation of Th17 Cells and IL-17 Expression

A series of experiments were done with N-(1-(((R)-1-(2-cyano-4,4-dimethylpent-2-enoyl)pyrrolidin-2-yl)methyl)-5-(((((S)-3,3-dimethylbutan-2-yl)amino)methyl)-1H-benzo[d]imidazol-2-yl)-5-(difluoromethyl)thiophene-2-carboxamide, Tool Compound A, to explore the effects of simultaneous inhibition of both ITK and RLK on the Th17/IL-17 T cell mechanism.
Differentiation of Th17 cells.:
CD4+ cells from TCR transgenic mice (B10.A 5C.C7 TCR Tg (Rag-2$^{-/-}$)) were grown for three days in the presence of culture conditions that support the differentiation of the T cell population to Th17 cells (optimized concentrations of IL-6, TGF-β, IL-1β, IL-23, anti-mouse IL-2, anti-mouse IFN-γ, and anti-mouse IL-4 mAb). This was done in the presence of varying concentrations of Tool Compound A in the cell culture medium during the differentiation procedure. The cells were then activated with a combination of phorbol 12-myristate 13-acetate and ionomycin and the expression of the Th17 specific transcription factor RORγt and intracellular IL-17A was measured by flow cytometry. Tool Compound A was potent at inhibiting Th17 differentiation and IL-17 expression with an $IC_{50}$ of approximately 25 nM (see Table 4).

TABLE 4

Inhibition of murine Th17 cell differentiation

| Readout | Midpoint of dose response - Th17 |
|---|---|
| Proliferation | <25 nM |
| Transcription factor expression (RORγt) | ~25 nM |
| Intracellular cytokine expression (IL-17) | <25 nM |

Figure 2:
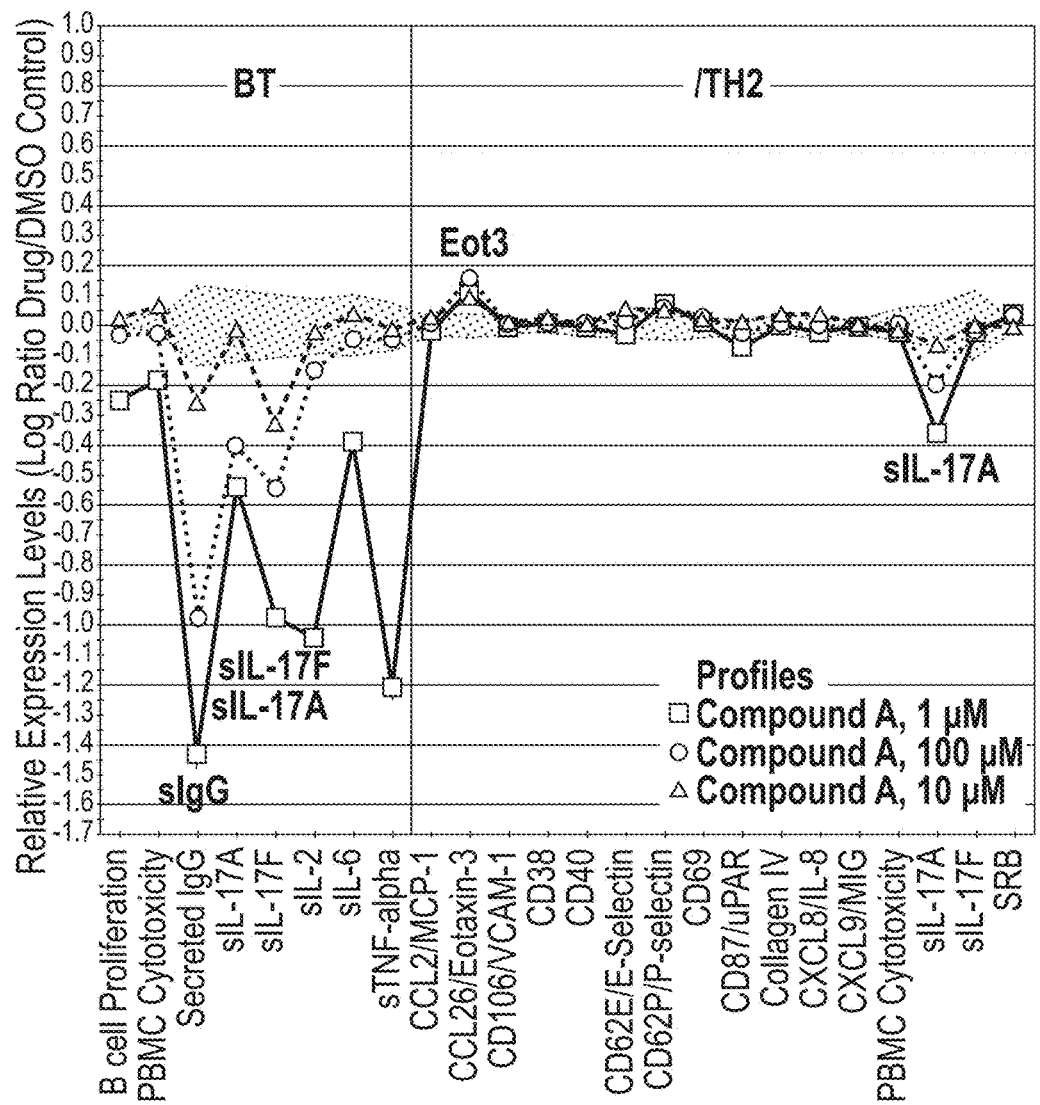
FIG. 2 depicts results from a BioMap® cell screening panel (performed by BioSeek, Inc., South San Francisco, Calif.) is a set of cell-based assays used to probe the cellular potency and selectivity of inhibitory compounds. A variety of cell culture and co-culture systems are stimulated with a range of molecules. Biomarker readouts are pathway activities in the culture systems. The biomarker readouts measured in each system are indicated along the x-axis. The y-axis shows the log 10 expression ratios of the readout level measurements relative to solvent (DMSO buffer) controls. Three concentrations of Compound A were tested for the ability to modulate the various readouts. The BT system and the TH2 system exhibit dose-dependent modulation of biomarkers in response to Compound A. The BT system consists of B cells co-cultured with peripheral blood mononuclear cells stimulated with anti-IgM and mild T-cell receptor stimulation and is designed to model T cell dependent B cell activation. The TH2 system consists of primary human umbilical vein endothelial cells co-cultured with 14-day TH2 polarized CD4 T-cell blasts stimulated with TCR and IL-2. PRN694 had essentially no inhibitory activity in cell types that were tested that do not express ITK and RLK (data not shown).

Inhibition of Murine Th17 Cell Differentiation
Expression of IL-17 by Human Th17 Cells Purified from a Human Leukocyte Population:
A population of T cells enhanced in Th17 cells was produced using the EasySep™ human Th17 enrichment kit from StemCell Technologies. These cells were exposed to 500 nM Tool Compound A for 1 h and then activated with anti-CD3/anti-CD28 (TCR stimulation) for 12 h followed by analysis of intracellular IL-17 expression by FACS. The single dose of 50 nM Tool Compound A completely blocked TCR-induced intracellular expression of IL-17 by purified Th17 cells (see FIG. 1).
Secretion of IL-17a in Cellular Co-Cultures of T Cells:
Tool Compound A was tested in T cell co-cultures consisting of either a mixture of human primary peripheral blood mononuclear cells (PBMC) and B cells or human primary differentiated Th2 cells and human umbilical vein endothelial cells. The PBMC-B cell co-cultures were stimulated with TCR activators anti-CD3 and anti-CD28 and anti-IgM antibodies for 84 h to simulate B cell activation driven by T cell activation. Tool Compound A was tested at 10 µM, 1 µM, 100 nM and 10 nM. IL-17A secretion into the culture supernatant was inhibited in a dose dependent manner. The primary Th2 cell-HUVEC co-cultures were stimulated by TCR activation and interleulin-2. In this co-culture system Tool Compound A also inhibited IL-17A secretion in a dose dependent manner (see FIG. 2).

Based on these three lines of evidence, it was concluded that simultaneous inhibition of ITK and RLK using Tool Compound A blocked Th17 differentiation, intracellular expression of IL-17 by Th17 cells, as well as secretion of IL-17. Therefore compounds of this selectivity pattern would have utility in diseases that are driven by an IL-17 mechanism.

PHARMACEUTICAL COMPOSITIONS

Parenteral Composition

To prepare a parenteral pharmaceutical composition suitable for administration by injection, 100 mg of a water-soluble salt of a compound of Formula I is dissolved in 2% HPMC, 1% Tween 80 in DI water, pH 2.2 with MSA, q.s. to at least 20 mg/mL. The mixture is incorporated into a dosage unit form suitable for administration by injection.

Oral Composition

To prepare a pharmaceutical composition for oral delivery, 400 mg of a compound of Formula I and the following ingredients are mixed intimately and pressed into single scored tablets.

Tablet Formulation

| Ingredient | Quantity per tablet mg |
|---|---|
| compound (I) | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule

| Ingredient | Quantity per capsule mg |
|---|---|
| compound (I) | 200 |
| lactose spray dried | 148 |
| magnesium stearate | 2 |

Sublingual (Hard Lozenge) Composition

To prepare a pharmaceutical composition for buccal delivery, such as a hard lozenge, mix 100 mg of a compound of Formula I with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Fast-Disintegrating Sublingual Tablet

A fast-disintegrating sublingual tablet is prepared by mixing 48.5% by weigh of a compound of Formula I, 44.5% by weight of microcrystalline cellulose (KG-802), 5% by weight of low-substituted hydroxypropyl cellulose (50 µm), and 2% by weight of magnesium stearate. Tablets are prepared by direct compression (AAPS PharmSciTech. 2006; 7(2):E41). The total weight of the compressed tablets is maintained at 150 mg. The formulation is prepared by mixing the amount of a compound of Formula I with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Inhalation Composition

To prepare a pharmaceutical composition for inhalation delivery, 20 mg of a compound of Formula I is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound of Formula I is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical opthalmic solution composition, 100 mg of a compound of Formula I is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound of Formula I is mixed with 30 mL of a 0.05M phosphate buffer solution (pH 4.4). The solution is placed in a nasal administrator designed to deliver 100 µL of spray for each application.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound of Formula (I):

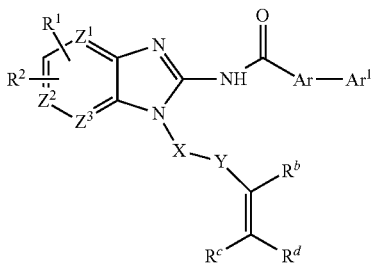

(I)

or a pharmaceutically acceptable salt thereof;

wherein:

$Z^1$, $Z^2$, and $Z^3$ are independently CH, or $CR^2$;

$R^1$ is hydrogen, or -(alkylene)-$NR^3R^5$, where $R^3$ is hydrogen, alkyl, or cycloalkyl, and $R^5$ is hydrogen, alkyl, haloalkyl, hydroxyalkyl, alkoxyalkyl, acyl, cycloalkyl, cycloalkylalkyl, optionally substituted heteroaryl, optionally substituted heteroaralkyl, heterocyclyl, or heterocyclylalkyl wherein the heterocyclyl ring in heterocyclyl and heterocyclylalkyl is optionally substituted with one, two, or three substituents independently selected from alkyl, halo, hydroxy, alkoxy, hydroxyalkyl, or alkoxyalkyl; or $R^3$ and $R^5$ together with the nitrogen atom to which they are attached form heterocycloamino or spiroheterocycloamino wherein the heterocycloamino ring is optionally substituted with one, two, or three substituents independently selected from alkyl, halo, hydroxyl, alkoxy, hydroxyalkyl, or alkoxyalkyl;

$R^2$ is hydrogen, or alkyl;

—Ar—$Ar^1$ is:

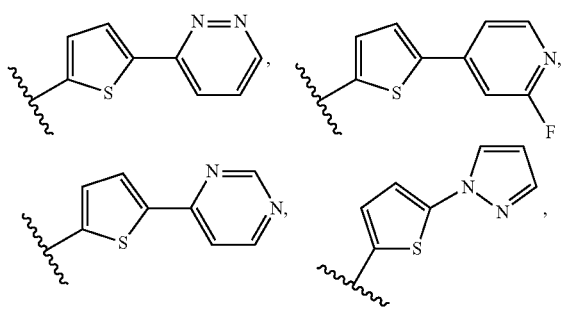

X is a moiety of formula II, where Z is alkylene, and ring A is heterocycloamino optionally substituted with one or two substituents independently selected from alkyl, hydroxy, or fluoro or -(alkylene)-$NR^a$— where $R^a$ is hydrogen;

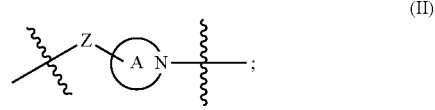

(II)

Y is —CO—;

$R^b$ is hydrogen, or cyano;

$R^c$ is hydrogen, or alkyl; and $R^d$ is hydrogen, or alkyl;

provided, however, when $R^b$ is cyano, then $R^d$ is hydrogen but $R^c$ is not hydrogen.

2. The compound of claim 1 or a pharmaceutically acceptable salt thereof wherein the compound of Formula (I) has the structure (Ia):

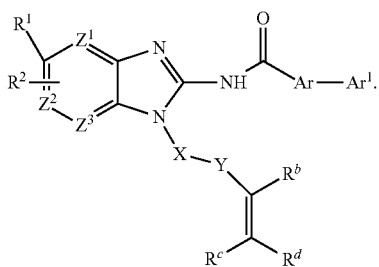

(Ia)

3. The compound of claim 1 or a pharmaceutically acceptable a salt thereof wherein $R^b$ is cyano and $R^c$ is alkyl.

4. The compound of claim 3 or a pharmaceutically acceptable salt thereof wherein $R^c$ is isopropyl or tert-butyl.

5. The compound of claim 1 or a pharmaceutically acceptable salt thereof wherein X is a moiety of formula II

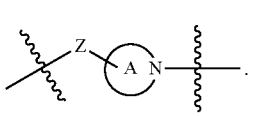

(II)

6. The compound of claim 1 or a pharmaceutically acceptable salt thereof wherein X is

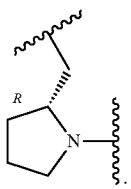

7. The compound of claim 1 or a pharmaceutically acceptable salt thereof wherein $R^1$ is —(CH$_2$)—NHR$^5$ where $R^5$ is 2,2-dimethylpropyl, 2-methylpropyl, cyclopropylmethyl, —CH$_2$C(CH$_3$)$_2$OH, (R)-CH(CH$_2$OH)C(CH$_3$)$_3$, (S)-CH(CH$_2$OH)C(CH$_3$)$_3$, (R)-CH(CH$_2$OH)CH$_3$, (S)-CH(CH$_2$OH)CH$_3$, (R)-CH(CH$_2$OCH$_3$)CH$_3$, (S)-CH(CH$_2$OCH$_3$)CH$_3$, (S)-CH(CH$_3$)C(CH$_3$)$_3$, (R)-CH(CH$_3$)C(CH$_3$)$_3$, tetrahydrofuran-4-yl, 2,2-difluoroethyl, tetrahydropyran-3-yl, oxazol-2-ylmethyl, thiazol-2-ylmethyl, tetrahydrofuran-2-ylmethyl, morpholin-4-ylmethyl.

8. The compound of claim 1 or a pharmaceutically acceptable salt thereof wherein $R^1$ is:

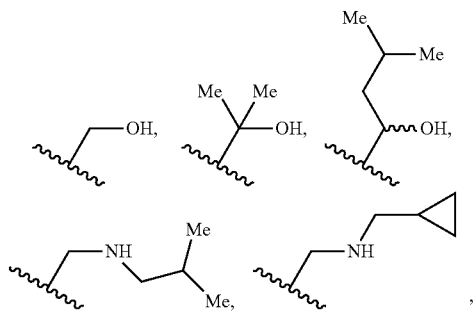

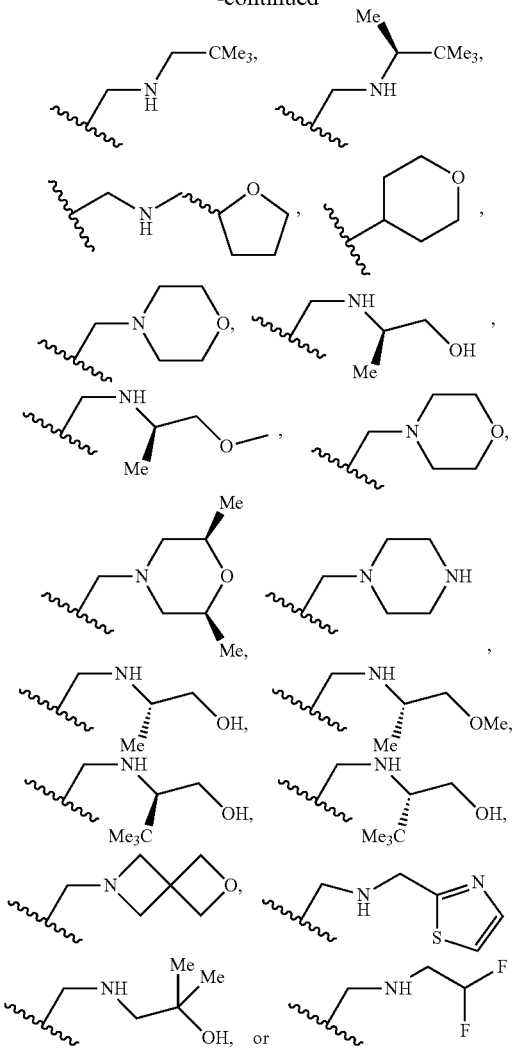

9. A compound selected from the group consisting of:
(R)-N-(1-((1-(2-cyano-4,4-dimethylpent-2-enoyl)pyrrolidin-2-yl)methyl)-5-(hydroxymethyl)-1H-benzo[d]imidazol-2-yl)-5-(oxazol-5-yl)thiophene-2-carboxamide;
(R)-N-(1-((1-(2-cyano-4,4-dimethylpent-2-enoyl)pyrrolidin-2-yl)methyl)-5-(((cyclopropyl-methyl)amino)methyl)-1H-benzo[d]imidazol-2-yl)-5-(oxazol-5-yl)thiophene-2-carboxamide;
N-(1-(((R)-1-(2-cyano-4,4-dimethylpent-2-enoyl)pyrrolidin-2-yl)methyl)-5-((((S)-1-hydroxy-3,3-dimethylbutan-2-yl)amino)methyl)-1H-benzo[d]imidazol-2-yl)-5-(oxazol-5-yl)thiophene-2-carboxamide;
N-(1-(((R)-1-(2-cyano-4,4-dimethylpent-2-enoyl)pyrrolidin-2-yl)methyl)-5-((((R)-1-hydroxy-3,3-dimethylbutan-2-yl)amino)methyl)-1H-benzo[d]imidazol-2-yl)-5-(oxazol-5-yl)thiophene-2-carboxamide;
N-(1-(((R)-1-(2-cyano-4,4-dimethylpent-2-enoyl)pyrrolidin-2-yl)methyl)-5-((((S)-1-hydroxypropan-2-yl)amino)methyl)-1H-benzo[d]imidazol-2-yl)-5-(oxazol-5-yl)thiophene-2-carboxamide;
N-(1-(((R)-1-(2-cyano-4,4-dimethylpent-2-enoyl)pyrrolidin-2-yl)methyl)-5-((((R)-1-hydroxypropan-2-yl)amino)methyl)-1H-benzo[d]imidazol-2-yl)-5-(oxazol-5-yl)thiophene-2-carboxamide;

N-(1-(((R)-1-(2-cyano-4,4-dimethylpent-2-enoyl)pyrrolidin-2-yl)methyl)-5-((((R)-1-methoxypropan-2-yl)amino)methyl)-1H-benzo[d]imidazol-2-yl)-5-(oxazol-5-yl)thiophene-2-carboxamide;

N-(1-(((R)-1-(2-cyano-4,4-dimethylpent-2-enoyl)pyrrolidin-2-yl)methyl)-5-((((S)-1-methoxypropan-2-yl)amino)methyl)-1H-benzo[d]imidazol-2-yl)-5-(oxazol-5-yl)thiophene-2-carboxamide;

(R)-N-(1-((1-acryloylpyrrolidin-2-yl)methyl)-5-(((cyclopropylmethyl)amino)methyl)-1H-benzo[d]imidazol-2-yl)-5-(oxazol-5-yl)thiophene-2-carboxamide;

N-(1-(((R)-1-acryloylpyrrolidin-2-yl)methyl)-5-((((S)-1-hydroxy-3,3-dimethylbutan-2-yl)amino)methyl)-1H-benzo[d]imidazol-2-yl)-5-(oxazol-5-yl)thiophene-2-carboxamide;

N-(1-(((R)-1-acryloylpyrrolidin-2-yl)methyl)-5-((((R)-1-hydroxy-3,3-dimethylbutan-2-yl)amino)methyl)-1H-benzo[d]imidazol-2-yl)-5-(oxazol-5-yl)thiophene-2-carboxamide;

N-(1-(((R)-1-acryloylpyrrolidin-2-yl)methyl)-5-((((S)-1-hydroxypropan-2-yl)amino)methyl)-1H-benzo[d]imidazol-2-yl)-5-(oxazol-5-yl)thiophene-2-carboxamide;

N-(1-(((R)-1-acryloylpyrrolidin-2-yl)methyl)-5-((((R)-1-hydroxypropan-2-yl)amino)methyl)-1H-benzo[d]imidazol-2-yl)-5-(oxazol-5-yl)thiophene-2-carboxamide;

(R)-N-(1-((1-acryloylpyrrolidin-2-yl)methyl)-5-(((2-hydroxy-2-methylpropyl)amino)methyl)-1H-benzo[d]imidazol-2-yl)-5-(oxazol-5-yl)thiophene-2-carboxamide;

N-(1-(((R)-1-(2-cyano-4,4-dimethylpent-2-enoyl)pyrrolidin-2-yl)methyl)-5-((((S)-3,3-dimethylbutan-2-yl)amino)methyl)-1H-benzo[d]imidazol-2-yl)-5-(oxazol-5-yl)thiophene-2-carboxamide;

(R)-N-(1-((1-(2-cyano-4,4-dimethylpent-2-enoyl)pyrrolidin-2-yl)methyl)-5-(((2-hydroxy-2-methylpropyl)amino)methyl)-1H-benzo[d]imidazol-2-yl)-5-(oxazol-5-yl)thiophene-2-carboxamide;

(R)-N-(1-((1-(2-cyano-4,4-dimethylpent-2-enoyl)pyrrolidin-2-yl)methyl)-5-(((tetrahydro-2H-pyran-4-yl)amino)methyl)-1H-benzo[d]imidazol-2-yl)-5-(oxazol-5-yl)thiophene-2-carboxamide;

(R)-N-(1-((1-(2-cyano-4,4-dimethylpent-2-enoyl)pyrrolidin-2-yl)methyl)-5-(((2,2-difluoroethyl)amino)methyl)-1H-benzo[d]imidazol-2-yl)-5-(oxazol-5-yl)thiophene-2-carboxamide;

N-(1-(((R)-1-(2-cyano-4,4-dimethylpent-2-enoyl)pyrrolidin-2-yl)methyl)-5-(((S)-2-(methoxymethyl)pyrrolidin-1-yl)methyl)-1H-benzo[d]imidazol-2-yl)-5-(oxazol-5-yl)thiophene-2-carboxamide;

N-(1-(((R)-1-(2-cyano-4,4-dimethylpent-2-enoyl)pyrrolidin-2-yl)methyl)-5-(((tetrahydrofuran-3-yl)amino)methyl)-1H-benzo[d]imidazol-2-yl)-5-(oxazol-5-yl)thiophene-2-carboxamide;

(R)-N-(1-((1-(2-cyano-4,4-dimethylpent-2-enoyl)pyrrolidin-2-yl)methyl)-5-(morpholinomethyl)-1H-benzo[d]imidazol-2-yl)-5-(oxazol-5-yl)thiophene-2-carboxamide;

N-(1-(((R)-1-(2-cyano-4,4-dimethylpent-2-enoyl)pyrrolidin-2-yl)methyl)-5-(((R)-2-(methoxymethyl)pyrrolidin-1-yl)methyl)-1H-benzo[d]imidazol-2-yl)-5-(oxazol-5-yl)thiophene-2-carboxamide;

N-(1-(((R)-1-(2-cyano-4,4-dimethylpent-2-enoyl)pyrrolidin-2-yl)methyl)-5-(1-hydroxy-3-methylbutyl)-1H-benzo[d]imidazol-2-yl)-5-(oxazol-5-yl)thiophene-2-carboxamide;

(R)-N-(1-((1-(2-cyano-4,4-dimethylpent-2-enoyl)pyrrolidin-2-yl)methyl)-5-((isobutyl-amino)methyl)-1H-benzo[d]imidazol-2-yl)-5-(oxazol-5-yl)thiophene-2-carboxamide;

(R)-N-(1-((1-(2-cyano-3-cyclopropylacryloyl)pyrrolidin-2-yl)methyl)-5-(((cyclopropyl-methyl)amino)methyl)-1H-benzo[d]imidazol-2-yl)-5-(oxazol-5-yl)thiophene-2-carboxamide;

(R)-N-(1-((1-(2-cyano-4-methylpent-2-enoyl)pyrrolidin-2-yl)methyl)-5-(((cyclopropyl-methyl)amino)methyl)-1H-benzo[d]imidazol-2-yl)-5-(oxazol-5-yl)thiophene-2-carboxamide;

(R)-N-(1-((1-(2-cyano-4,4-dimethylpent-2-enoyl)pyrrolidin-2-yl)methyl)-5-((neopentylamino)methyl)-1H-benzo[d]imidazol-2-yl)-5-(oxazol-5-yl)thiophene-2-carboxamide;

N-(1-(((R)-1-acryloylpyrrolidin-2-yl)methyl)-5-((((S)-3,3-dimethylbutan-2-yl)amino)methyl)-1H-benzo[d]imidazol-2-yl)-5-(oxazol-5-yl)thiophene-2-carboxamide;

N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(2-fluoropyridin-4-yl)thiophene-2-carboxamide;

N-((E)-1-(((R)-1-((E)-2-cyano-3-cyclopropylacryloyl)pyrrolidin-2-yl)methyl)-5-(hydroxymethyl)-1,3-dihydro-2H-benzo[d]imidazol-2-ylidene)-5-(oxazol-5-yl)thiophene-2-carboxamide;

N-((E)-1-(((R)-1-((E)-2-cyano-4,4-dimethylpent-2-enoyl)pyrrolidin-2-yl)methyl)-5-(((cyclopropylmethyl)amino)methyl)-1,3-dihydro-2H-benzo[d]imidazol-2-ylidene)-5-(2-fluoropyridin-4-yl)thiophene-2-carboxamide;

N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(2-methyl-oxazol-5-yl)thiophene-2-carboxamide;

N-((E)-1-(((R)-1-((E)-2-cyano-4-methylpent-2-enoyl)pyrrolidin-2-yl)methyl)-5-(hydroxymethyl)-1,3-dihydro-2H-benzo[d]imidazol-2-ylidene)-5-(oxazol-5-yl)thiophene-2-carboxamide;

N-((E)-1-(((R)-1-((E)-2-cyano-4-methylpent-2-enoyl)pyrrolidin-2-yl)methyl)-5-((((S)-1-methoxypropan-2-yl)amino)methyl)-1,3-dihydro-2H-benzo[d]imidazol-2-ylidene)-5-(oxazol-5-yl)thiophene-2-carboxamide;

N-((E)-1-(((R)-1-((E)-2-cyano-4,4-dimethylpent-2-enoyl)pyrrolidin-2-yl)methyl)-5-(((cyclopropylmethyl)amino)methyl)-1,3-dihydro-2H-benzo[d]imidazo 2-ylidene)-5-(2-methyloxazol-5-yl)thiophene-2-carboxamide;

N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(1H-pyrazol-1-yl)thiophene-2-carboxamide;

N-((E)-1-(((R)-1-((E)-2-cyano-3-(1-methylcyclopropyl)acryloyl)pyrrolidin-2-yl)methyl)-5-(hydroxymethyl)-1,3-dihydro-2H-benzo[d]imidazol-2-ylidene)-5-(oxazol-5-yl)thiophene-2-carboxamide;

N-((E)-1-(((R)-1-((E)-2-cyano-3-cyclopropylacryloyl)pyrrolidin-2-yl)methyl)-5-(((2-hydroxy-2-methylpropyl)amino)methyl)-1,3-dihydro-2H-benzo[d]imidazol-2-ylidene)-5-(oxazol-5-yl)thiophene-2-carboxamide;

N-((E)-1-(((R)-1-((E)-2-cyano-4,4-dimethylpent-2-enoyl)pyrrolidin-2-yl)methyl)-5-(((cyclopropylmethyl)amino)methyl)-1,3-dihydro-2H-benzo[d]imidazol-2-ylidene)-5-(1H-pyrazol-1-yl)thiophene-2-carboxamide;

N-((E)-1-(((R)-1-((E)-2-cyano-4,4-dimethylpent-2-enoyl)pyrrolidin-2-yl)methyl)-5-(((cyclopropylmethyl)amino)methyl)-1,3-dihydro-2H-benzo[d]imidazol-2-ylidene)-5-(1H-1,2,4-triazol-1-yl)thiophene-2-carboxamide;

N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(1H-1,2,4-triazol-1-yl)thiophene-2-carboxamide;

N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(pyrimidin-4-yl)thiophene-2-carboxamide;

N-((E)-1-(((R)-1-((E)-2-cyano-3-cyclopropylacryloyl)pyrrolidin-2-yl)methyl)-5-((((S)-1-methoxypropan-2-yl)amino)methyl)-1,3-dihydro-2H-benzo[d]imidazol-2-ylidene)-5-(oxazol-5-yl)thiophene-2-carboxamide;

N-((E)-1-(((R)-1-((E)-2-cyano-3-(1-methylcyclopropyl)acryloyl)pyrrolidin-2-yl)methyl)-5-((((S)-1-methoxypropan-2-yl)amino)methyl)-1,3-dihydro-2H-benzo[d]imidazol-2-ylidene)-5-(oxazol-5-yl)thiophene-2-carboxamide;

N-((E)-1-(((R)-1-((E)-2-cyano-4,4-dimethylpent-2-enoyl)pyrrolidin-2-yl)methyl)-5-(((cyclopropylmethyl)amino)methyl)-1,3-dihydro-2H-benzo[d]imidazol-2-ylidene)-5-(pyrimidin-4-yl)thiophene-2-carboxamide;

N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(1,2,4-oxadiazol-3-yl)thiophene-2-carboxamide;

N-((E)-1-(((R)-1-((E)-2-cyano-4,4-dimethylpent-2-enoyl)pyrrolidin-2-yl)methyl)-5-((((S)-3,3-dimethylbutan-2-yl)amino)methyl)-,3-dihydro-2H-benzo[d]imidazol-2-ylidene)-5-(1H-1,2,4-triazol-1-yl)thiophene-2-carboxamide;

N-((E)-1-(((R)-1-((E)-2-cyano-4,4-dimethylpent-2-enoyl)pyrrolidin-2-yl)methyl)-5-((((S)-3,3-dimethylbutan-2-yl)amino)methyl)-1,3-dihydro-2H-benzo[d]imidazol-2-ylidene)-5-(1,2,4-oxadiazol-3-yl)thiophene-2-carboxamide;

N-((E)-1-(((R)-1-((E)-2-cyano-3-(1-methylcyclopropyl)acryloyl)pyrrolidin-2-yl)methyl)-5-(((2-hydroxy-2-methylpropyl)amino)methyl)-1,3-dihydro-2H-benzo[d]imidazol-2-ylidene)-5-(oxazol-5-yl)thiophene-2-carboxamide;

N-((E)-1-(((R)-1-((E)-2-cyano-4,4-dimethylpent-2-enoyl)pyrrolidin-2-yl)methyl)-5-(hydroxymethyl)-1,3-dihydro-2H-benzo[d]imidazol-2-ylidene)-5-(4H-1,2,4-triazazol-3-yl)thiophene-2-carboxamide;

N-((E)-1-(((R)-1-((E)-2-cyano-4,4-dimethylpent-2-enoyl)pyrrolidin-2-yl)methyl)-5-(((3,3-dimethylbutan-2-yl)amino)methyl)-1,3-dihydro-2H-benzo[d]imidazol-2-ylidene)-5-(pyrimidin-4-yl)thiophene-2-carboxamide;

N-((E)-1-(((R)-1-((E)-2-cyano-4,4-dimethylpent-2-enoyl)pyrrolidin-2-yl)methyl)-5-((((S)-3,3-dimethylbutan-2-yl)amino)methyl)-1,3-dihydro-2H-benzo[d]imidazol-2-ylidene)-5-(2-fluoropyridin-4-yl)thiophene-2-carboxamide;

N-((E)-1-(((R)-1-((E)-2-cyano-4,4-dimethylpent-2-enoyl)pyrrolidin-2-yl)methyl)-5-((((S)-3,3-dimethylbutan-2-yl)amino)methyl)-1,3-dihydro-2H-benzo[d]imidazol-2-ylidene)-5-(pyrazin-2-yl)thiophene-2-carboxamide;

N-((E)-1-(2-((E)-2-cyano-N,4,4-trimethylpent-2-enamido)-2-methylpropyl)-5-((((S)-3,3-dimethylbutan-2-yl)amino)methyl)-1,3-dihydro-2H-benzo[d]imidazol-2-ylidene)-5-(oxazol-5-yl)thiophene-2-carboxamide;

(S,E)-N-(1-(2-(2-cyano-N-methylacrylamido)-2-methylpropyl)-5-(((3,3-dimethylbutan-2-yl)amino)methyl)-1,3-dihydro-2H-benzo[d]imidazol-2-ylidene)-5-(oxazol-5-yl)thiophene-2-carboxamide;

N-((E)-1-(2-((E)-2-cyano-N,4-dimethylpent-2-enamido)-2-methylpropyl)-5-(((2-hydroxy-2-methylpropyl)amino)methyl)-1,3-dihydro-2H-benzo[d]imidazol-2-ylidene)-5-(oxazol-5-yl)thiophene-2-carboxamide;

N-((E)-1-(2-((E)-2-cyano-4,4-dimethylpent-2-enamido)-2-methylpropyl)-5-(((((S)-3,3-dimethylbutan-2-yl)amino)methyl)-1,3-dihydro-2H-benzo[d]imidazol-2-ylidene)-5-(oxazol-5-yl)thiophene-2-carboxamide;

(S,E)-N-(1-(2-acrylamido-2-methylpropyl)-5-(((3,3-dimethylbutan-2-yl)amino)methyl)-1,3-dihydro-2H-benzo[d]imidazol-2-ylidene)-5-(oxazol-5-yl)thiophene-2-carboxamide; and, N-((E)-1-(((R)-1-((Z)-2-cyano-4,4-dimethylpent-2-enoyl)piperidin-3-yl)methyl)-5-((((S)-3,3-dimethylbutan-2-yl)amino)methyl)-1,3-dihydro-2H-benzo[d]imidazol-2-ylidene)-5-(oxazol-5-yl)thiophene-2-carboxamide;

or a pharmaceutically acceptable salt thereof.

10. A pharmaceutical composition comprising a compound of claim 1, or a pharmaceutically acceptable salt thereof; and a pharmaceutically acceptable excipient.

11. A method of treating a disease treatable by inhibition of IL17 production in a mammal, where the disease is an autoimmune disease, an inflammatory disease or cancer, comprising administering to the mammal suffering from the disease, a pharmaceutical composition comprising a compound of claim 1 or a pharmaceutically acceptable salt thereof in a therapeutically effective amount and a pharmaceutically acceptable excipient.

12. The method of claim 11 wherein the mammal is a human.

13. The method of claim 12 wherein the disease is psoriasis, psoriatic arthritis, rheumatoid arthritis, multiple sclerosis, inflammatory bowel disease, Crohn's disease, ulcerative colitis, Behcet's disease, uveitis, keratitis, asthma, testitis, systemic lupus erythematosus, lupus nephritis, nephritis, chronic active hepatitis, Graft-versus-host disease, primary biliary cirrhosis, scleroderma, atopic dermatitis, nephrotic syndrome, pediatric autoimmune enteropathy, primary sclerosing cholangitis, pyoderma gangrenosum, alopecia universalis, or large granular lymphocyte leukemia.

14. A pharmaceutical composition comprising a compound of claim 9, or a pharmaceutically acceptable salt thereof; and a pharmaceutically acceptable excipient.

15. A method of treating a disease treatable by inhibition of IL17 production in a mammal, where the disease in an autoimmune disease, an inflammatory disease or cancer, comprising administering to the mammal suffering from the disease, a pharmaceutical composition comprising a compound of claim 9 or a pharmaceutically acceptable salt thereof in a therapeutically effective amount and a pharmaceutically acceptable excipient.

16. The method of claim 15 wherein the mammal is a human.

17. The method of claim 16 wherein the disease is psoriasis, psoriatic arthritis, rheumatoid arthritis, multiple sclerosis, inflammatory bowel disease, Crohn's disease, ulcerative colitis, Behcet's disease, uveitis, keratitis, asthma, testitis, systemic lupus erythematosus, lupus nephritis, nephritis, chronic active hepatitis, Graft-versus-host disease, primary biliary cirrhosis, scleroderma, atopic dermatitis, nephrotic syndrome, pediatric autoimmune enteropathy, primary sclerosing cholangitis, pyoderma gangrenosum, alopecia universalis, or large granular lymphocyte leukemia.

\* \* \* \* \*